(12) United States Patent
Livingston

(10) Patent No.: US 8,264,684 B2
(45) Date of Patent: *Sep. 11, 2012

(54) SCANNING ANALYZER FOR SINGLE MOLECULE DETECTION AND METHODS OF USE

(75) Inventor: Richard Livingston, Webster Groves, MO (US)

(73) Assignee: Singulex, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/031,784

(22) Filed: Feb. 22, 2011

(65) Prior Publication Data

US 2011/0263043 A1    Oct. 27, 2011

Related U.S. Application Data

(62) Division of application No. 12/338,955, filed on Dec. 18, 2008, now Pat. No. 7,914,734.

(60) Provisional application No. 61/015,142, filed on Dec. 19, 2007.

(51) Int. Cl.
*G01N 21/00* (2006.01)

(52) U.S. Cl. .......... 356/337; 73/863; 73/81; 250/472.1; 250/428; 356/36; 422/50; 422/63; 422/82.05

(58) Field of Classification Search .......... 250/472.1, 250/473.1, 428; 356/36, 337; 422/50, 63, 422/82.05; 73/863, 864.81

See application file for complete search history.

(56) References Cited

U.S. PATENT DOCUMENTS

| | | | |
|---|---|---|---|
| 4,071,298 A | 1/1978 | Falconer | |
| 4,168,146 A | 9/1979 | Grubb et al. | |
| 4,172,227 A | 10/1979 | Tyrer et al. | |
| 4,235,601 A | 11/1980 | Deutsch et al. | |
| 4,243,318 A | 1/1981 | Stohr | |
| 4,251,733 A | 2/1981 | Hirleman | |
| 4,366,241 A | 12/1982 | Tom et al. | |
| 4,442,204 A | 4/1984 | Greenquist et al. | |
| 4,452,773 A | 6/1984 | Molday | |
| 4,768,879 A | 9/1988 | McLachlan et al. | |
| 4,770,183 A | 9/1988 | Groaman et al. | |
| 4,793,705 A | 12/1988 | Shera | |

(Continued)

FOREIGN PATENT DOCUMENTS

DE    3720844 A1    1/1989

(Continued)

OTHER PUBLICATIONS

Alexa Fluor Dyes Handbook. Simply the Best and Brightest: Fluorescent Dyes and Conjugates. Invitrogen. Copyright 2005. Molecular Probes. 1-33.

(Continued)

*Primary Examiner* — Gregory J Toatley
*Assistant Examiner* — Iyabo S Alli
(74) *Attorney, Agent, or Firm* — McDonnell Boehnen Hulbert & Berghoff LLP

(57) ABSTRACT

The invention encompasses analyzers and analyzer systems that include a single molecule analyzer, methods of using the analyzer and analyzer systems to analyze samples, either for single molecules or for molecular complexes. The single molecule uses electromagnetic radiation that is translated through the sample to detect the presence or absence of a single molecule. The single molecule analyzer provided herein is useful for diagnostics because the analyzer detects single molecules with zero carryover between samples.

27 Claims, 5 Drawing Sheets

U.S. PATENT DOCUMENTS

| | | | |
|---|---|---|---|
| 4,927,265 A | 5/1990 | Brownlee |
| 4,979,824 A | 12/1990 | Mathies et al. |
| 5,002,389 A | 3/1991 | Benser |
| 5,041,733 A | 8/1991 | Noguchi et al. |
| 5,094,594 A | 3/1992 | Brennan |
| 5,108,179 A | 4/1992 | Myers |
| 5,138,170 A | 8/1992 | Noguchi et al. |
| 5,208,535 A | 5/1993 | Nakayama et al. |
| 5,209,834 A | 5/1993 | Shera |
| 5,230,997 A | 7/1993 | Frenkel |
| 5,269,937 A | 12/1993 | Dollinger et al. |
| 5,274,240 A | 12/1993 | Mathies et al. |
| 5,385,707 A | 1/1995 | Miltenyi et al. |
| 5,480,614 A | 1/1996 | Kamahori |
| 5,540,494 A | 7/1996 | Purvis, Jr. et al. |
| 5,543,838 A | 8/1996 | Hosier et al. |
| 5,547,849 A | 8/1996 | Baer et al. |
| 5,571,410 A | 11/1996 | Swedberg et al. |
| 5,603,351 A | 2/1997 | Cherukuri et al. |
| 5,605,662 A | 2/1997 | Heller et al. |
| 5,633,503 A | 5/1997 | Kosaka |
| 5,645,702 A | 7/1997 | Witt et al. |
| 5,653,859 A | 8/1997 | Parton et al. |
| 5,653,939 A | 8/1997 | Hollis et al. |
| 5,658,413 A | 8/1997 | Kaltenbach et al. |
| 5,681,751 A | 10/1997 | Begg et al. |
| 5,682,038 A | 10/1997 | Hoffman |
| 5,716,825 A | 2/1998 | Hancock et al. |
| 5,730,187 A | 3/1998 | Howitz et al. |
| 5,746,901 A | 5/1998 | Balch et al. |
| 5,755,942 A | 5/1998 | Zanzucchi et al. |
| 5,770,029 A | 6/1998 | Nelson et al. |
| 5,793,485 A | 8/1998 | Gourley |
| 5,795,158 A | 8/1998 | Warinner |
| 5,798,222 A | 8/1998 | Goix |
| 5,807,677 A | 9/1998 | Eigen et al. |
| 5,858,195 A | 1/1999 | Ramsey |
| 5,863,801 A | 1/1999 | Southgate et al. |
| 5,949,532 A | 9/1999 | Schrof et al. |
| 5,955,028 A | 9/1999 | Chow |
| 5,989,402 A | 11/1999 | Chow et al. |
| 5,999,250 A | 12/1999 | Hairston et al. |
| 6,033,628 A | 3/2000 | Kaltenbach et al. |
| 6,041,515 A | 3/2000 | Ally et al. |
| 6,049,380 A | 4/2000 | Goodwin et al. |
| 6,071,478 A | 6/2000 | Chow |
| 6,114,180 A | 9/2000 | Doth et al. |
| 6,130,101 A | 10/2000 | Mao et al. |
| 6,131,101 A | 10/2000 | Maitino et al. |
| 6,132,580 A | 10/2000 | Mathies et al. |
| 6,140,048 A | 10/2000 | Muller et al. |
| 6,143,152 A | 11/2000 | Simpson et al. |
| 6,177,277 B1 | 1/2001 | Soini |
| 6,208,815 B1 | 3/2001 | Seidel et al. |
| 6,211,955 B1 | 4/2001 | Basiji et al. |
| 6,242,266 B1 | 6/2001 | Schleifer et al. |
| 6,249,341 B1 | 6/2001 | Basiji et al. |
| 6,280,960 B1 | 8/2001 | Carr |
| 6,309,886 B1 | 10/2001 | Ambrose et al. |
| 6,355,420 B1 | 3/2002 | Chan |
| 6,361,671 B1 | 3/2002 | Mathies et al. |
| 6,386,219 B1 | 5/2002 | Barth et al. |
| 6,388,746 B1 | 5/2002 | Eriksson et al. |
| 6,403,338 B1 | 6/2002 | Knapp et al. |
| 6,403,947 B1 | 6/2002 | Hoyt et al. |
| 6,473,176 B2 | 10/2002 | Basiji et al. |
| 6,495,104 B1 | 12/2002 | Unno et al. |
| 6,506,609 B1 | 1/2003 | Wada et al. |
| 6,532,067 B1 | 3/2003 | Chang et al. |
| 6,533,553 B2 | 3/2003 | Caren |
| 6,537,437 B1 | 3/2003 | Galambos et al. |
| 6,554,744 B2 | 4/2003 | Schmidt |
| 6,582,903 B1 | 6/2003 | Rigler et al. |
| 6,599,436 B1 | 7/2003 | Matzke et al. |
| 6,608,680 B2 | 8/2003 | Basiji et al. |
| 6,623,613 B1 | 9/2003 | Mathies et al. |
| 6,689,323 B2 | 2/2004 | Fisher et al. |
| 6,710,871 B1 | 3/2004 | Goix |
| 6,749,734 B1 | 6/2004 | Simpson et al. |
| 6,766,817 B2 | 7/2004 | Da Silva |
| 6,783,992 B2 | 8/2004 | Robotti et al. |
| 6,802,342 B2 | 10/2004 | Fernandes et al. |
| 6,811,668 B1 | 11/2004 | Berndt et al. |
| 6,816,257 B2 | 11/2004 | Goix |
| 6,918,404 B2 | 7/2005 | Dias Da Silva |
| 6,974,305 B2 | 12/2005 | Garrett, III |
| 6,974,874 B2 | 12/2005 | Venham et al. |
| 6,977,305 B2 | 12/2005 | Leung et al. |
| 7,066,586 B2 | 6/2006 | Da Silva |
| 7,572,640 B2 * | 8/2009 | Goix et al. ............ 436/164 |
| 7,914,734 B2 * | 3/2011 | Livingston ............ 250/472.1 |
| 2002/0030812 A1 | 3/2002 | Ortyn et al. |
| 2002/0167665 A1 | 11/2002 | Yeung et al. |
| 2003/0029995 A1 | 2/2003 | Mullins et al. |
| 2003/0078737 A1 | 4/2003 | Keys et al. |
| 2003/0124592 A1 | 7/2003 | Puskas |
| 2003/0222007 A1 | 12/2003 | Gu et al. |
| 2004/0022684 A1 | 2/2004 | Heinze et al. |
| 2004/0166514 A1 | 8/2004 | Puskas |
| 2004/0214211 A1 | 10/2004 | Gilmanshin et al. |
| 2005/0164205 A1 | 7/2005 | Puskas |
| 2005/0221408 A1 | 10/2005 | Nalefski et al. |
| 2006/0003333 A1 | 1/2006 | Puskas |
| 2006/0004188 A1 | 1/2006 | Leung et al. |
| 2006/0078915 A1 | 4/2006 | Fuchs et al. |
| 2006/0078998 A1 | 4/2006 | Puskas et al. |
| 2006/0099638 A1 | 5/2006 | Leung et al. |
| 2006/0160209 A1 | 7/2006 | Larson et al. |
| 2006/0228747 A1 | 10/2006 | Fuchs et al. |
| 2008/0003685 A1 | 1/2008 | Goix et al. |
| 2008/0064113 A1 | 3/2008 | Goix et al. |
| 2008/0158543 A1 | 7/2008 | Puskas et al. |
| 2008/0171352 A1 | 7/2008 | Goix et al. |
| 2009/0171590 A1 | 7/2009 | Puskas et al. |
| 2010/0112727 A1 | 5/2010 | Todd et al. |
| 2010/0329929 A1 | 12/2010 | Goix et al. |

FOREIGN PATENT DOCUMENTS

| | | |
|---|---|---|
| WO | 9010876 A1 | 9/1990 |
| WO | 9940416 A1 | 8/1999 |
| WO | 9954497 A1 | 10/1999 |
| WO | 9955461 A1 | 11/1999 |
| WO | 2005089524 A2 | 9/2005 |
| WO | 2005119265 A1 | 12/2005 |
| WO | 2006036182 A2 | 4/2006 |
| WO | WO 2005/089524 A3 | 4/2006 |
| WO | 2007114947 A2 | 10/2007 |
| WO | 2007124384 A1 | 11/2007 |

OTHER PUBLICATIONS

Alexa Fluor Succinimidyl Esters. Invitrogen. Revised Jan. 4, 2006; 1-5.

Ambrose, et al. Single molecule fluorescence spectroscopy at ambient temperature. Chemical Reviews, 99:2929-56 (1999).

Anazawa, et al. Electrophoretic quantitation of nucleic acids without amplification by single molecule imaging, Anal. Chem, 74:5033-38 (2002).

Becker, et al., Three-dimensional photogrammetric particle-tracking velocimetry, Preparing for the Future, 5(3)(1995); available at http://esapub.esrin.esa.it/pff/pffv5n3/beckv5nc.htm(7 pages).

Biesche, et al., Ultrasensitive detection of pathological prion protein aggregates by dual-color scanning for intensely fluorescent targets, Pro. Natl. Acad. Sci., 97:5468-5473 (2000).

Bouchon, et al. Cutting edge: inflammatory responses can be triggered by TREM-1, a novel receptor expressed on neutrophils and monocytes, The Journal of Immunology, 164:4991-4995 (2000).

Borrebaeck, C., Antibody Engineering. Second Edition, Oxford University Press, Oxford (1995).

Brinkmeier, et al., Two-beam cross-correlation: a method to characterize transport phenomena in micrometer-sized structures, Anal. Chem., 71:609-616 (1999).

Castro, et al. Fluorescence detection and size measurement of single DNA molecules, Anal. Chem., 65:849-852 (1993).

Castro, et al., Single molecule detection: applications to ultrasensitive biochemical analysis, Applied Optics, 34:3218-3222 (1995).

Castro, et al. Single-molecule detection of specific nucleic acid sequences in unamplified genomic DNA, Anal. Chem., 69:3915-3920 (1997).

Castro, et al., Ultrasensitive, direct detection of a specific DNA sequence of *Bacillus antracis* in solution, The Analyst 125:9-11 (2000).

Chan, et al,. DNA mapping using microfluidic stretching and single-molecule detection of fluorescent site-specific tags, Genome Res. 14:1137-46 (2004).

Cohen, et al., Rapid separation and purification of oligonucleotides by high performance capillary gel electrophoresis, Proc. Natl. Acad. Sci., 85:9660-9663 (1988).

Colonna, M., TREMS in the immune system and beyond, Nature Reviews: Immunology 3:445-453 (2003).

CSIRO Australia, Image motion, tracking and registration. Available at http://www.cmis.csiro.au/IAP/Motion. Accessed Jan. 24, 2005.

D'Antoni, et al., Rapid quantitative analysis using a single molecule counting, Anal. Biochem., 352:97-109 (2006).

Dovichi, et al., Laser-induced fluorescence of flowing samples as an approach to single-molecule detection in liquids. Anal. Chem., 56:348-354 (1984).

Dunbar, et al., Quantitative, multiplexed detection of bacterial pathogens: DNA and protein applications of Luminex LabMap system, J. Microbiol Methods, 53:245-252 (2003).

Effenhauser, et al, Integrated capillary electrophoresis on flexible silicone microdevices: analysis of DNA restriction fragments and detection of single DNA molecules on microchips, Anal. Chem., 69:3451-3457 (1997).

Etzioni, et al., The case for early detection, Nature Reviews: Cancer 3:243-252 (2003).

Fister, et al. Counting single chromphore molecules for ultrasensitive analysis and separations on microchip devices, Anal. Chem., 70:431-437 (1998).

Gibot, et al., Plasma level of a triggering receptor expressed on myeloid cells-1: its diagnostic accuracy in patients with suspected sepsis, Annals of Internal Medicine, 141:9-15 (2004).

Gibot, et al., Soluble triggering receptor expressed on muyeloid cells and the diagnosis of pneumonia, The New england Journal of Medicine, 350:451-458 (2004).

Glenn Research Center, NASA, Particle Imaging Velocimetry. Available at http://www.grc.nasa.gov/www/Optlinstr/piv/background.htm and associated web pages. Accessed Jan. 26, 2005.

Goix, P., Fulfilling the Promise of Biomarkers in Drug Discovery and Development, Drug Discovery + International, 6-7, Apr./May 2007.

Goix, P., Slides from presentation at clinical biomarkers summit, Coronado, CA, Mar. 29-31, 2006.

Golde, T., Alzheimer disease therapy: can the amyloid cascade be halted?, The Journal of Clinical Investigation, 11:11-18 (2003).

Guenard, et al., Two-channel sequential single-molecule measurement, Anal. Chem., 69:2426-2433 (1997).

Guide to Labeling Antibodies with Alexa Fluor Dyes, 24-28 (2004).

Haab, et al., Single molecule florescence burst detection of DNA fragments separated by capillary electrophoresis., Anal Chem., 67:3523-3260 (1995).

Haab, et al., Single-molecule detection of DNA separations in microfabricated capillary electrophoresis chips employing focused molecular stream, Anal Chem., 71:5137-5145 (1999).

Huse, et al. Application of a filamentous phage pVIII fusion protein system suitable for efficient production, screening and mutagenesis of F(ab)antibody fragments, J. Immunol. 149:3914-20 (1992).

Haugland, Molelcular Probes Handbook of Fluorescent Probes and Research Product, Ninth Edition, Molecular Probes, Inc. (Table of Contents only) 2002.

Keller, et al., Analytical applications of single-molecule detection, Analytical Chemistry 74:317A-324A (2002).

Klee, Human anti-mouse antibodies, Arch Pathol Lab Med. 124:921-3 (2000).

Koerbin, et al., The Comparative analytical performance of four troponin I assays at low concentration, Ann Clin. Biochem., 42:19-23 (2005).

LeCaptain, et al., Two-beam fluorescence cross-correlation spectroscopy in an electrophoretic mobility shift assay, Anal. Chem., 74:1171-1176 (2002).

Li, et al. Ultrasensitive coincidence fluorescence detection of single DNA molecules, Anal. Chem., 75:1664-1670 (2003).

Loscher, et al., Counting of single protein molecules at interfaces and application of this technique in early-stage diagnosis, Anal. Chem, 70:3202-5 (1998).

Lucey, et al., Type 1 and type 2 cytokine dysregulation in human infectious, neoplastic and inflammatory diseases, Clinical Biology Reviews 9:532-562 (1996).

Ma, et al., Single-molecule immunoassay and DNA diagnosis, Electrophoresis 22:421-426 (2001).

Nalefski, et al., Single-molecule counting of macromolecular complexes in real time: a novel approach to quantify transcription factor-DNA and antibody-antigen interaction, Faseb Journal 18:C176 (2004).

Nguyen, et al., Detection of single molecules of phycoerythrin in hydrodynamically focused flows by laser-induced fluorescence, Anal. Chem., 59:2158-2161 (1987).

Panchuk-Voloshina, et al., Alexa dyes, a series of new fluorescent dyes that yield exceptionally bright, photostable conjugates, J. Histochem Cytochem, 47:1179-88 (1999).

Park, Addressing Unmet Needs in Assay Development. Medical Device Link 1-4, Mar. 2007.

Phillips, et al., Application of single molecule technology to rapidly map long DNA and study the conformation of stretched DNA., Nucleic Acids Res. 33:5829-37 (2005).

Bigler, Fluorescence correlations, single molecule detection and large number screening, Applications in biotechnology, J Biotechnol. 41:177-86 (1995).

Sauer, et al., Detection and identification of individual antigen molecules in human serum with pulsed semiconductor lasers, Appl. Phys. B., 65:427-431 (1997).

Shera, et al., Detection of single fluorescent molecules, Chemical Physics Letters, 174:553-557 (1990).

Shortreed, et al., High-throughput single-molecule DNA screening based on electrophoresis, Anal. Chem., 72:2879-2885 (2000).

Sidransky, Emerging molecular markers of cancer, Nature Reviews: Cancer. 2:210-219 (2002).

Soper, et al., Photon burst detection of single near-infrared fluorescent molecules, Anal. Chem., 65:740-747 (1993).

Soper, et al., Single-molecule detection in the near-IR using continuous wave diode laser excitation with an avalanche photon detector, Applied Spectroscopy 52:1-6 (1998).

Tanaka, et al., Protein and polymer analyses up to m/z 100 000 by laser ionization time-of-flight mass spectrometry, Rapid Commun. Mass. Spect. 2:151-153 (1988).

Upatnieks, et al., A kilohertz frame rate cinemagraphic PIV system for laboratory-scale turbulent and unsteady flows, Experiments in Fluids 32:87-98 (2002).

Van Orden, et al., Single-molecule identification in flowing sample streams by fluorescence burst size in intraburst fluorescence decay rate, Anal. Chem., 70:1444-1451 (1998).

Wabuyele, et al., Single molecule detection of double-stranded DNA in poly(methylmethacrylate) and polycarbonate microfluidic devices, Electrophoresis, 22:3939-3948 (2001).

Willneff, J., A spatio-temporal matching algorithm for 3D particle tracking velocimetry: a dissertation submitted to the Swwiss Federal Institute of Technology Zurich for the degree of Doctroal of Technical sciences (abstract), Sep. 2003, Diss. Eth No. 15276. Available at http://e-collection.ethbib.ethz.ch/ecol-pool/dissiabstracts/p15276.pdf.

Wu, et al., Development and preliminary clinical validation of a high sensitivity assay for cardiac troponin using a capillary flow (single molecule) fluorescence detector. Poster presented at Oak Ridge Conference. Apr. 21-22, 2006, San Jose, CA.

Wu, et al., Development and Preliminary clinical validation of a high Sensitivity Assay for Cardiac Tropoin using a Capillary Flow (Single Molecule) Fluorescence detector, Clinical Chemistry 52:2157-2159 (2006).

Young, Singles Developing Troponin Test for earlier detection of AMI, Medical Device Daily, Dec. 13, 2006.

Zhu, et al., Fluorescence multiplexing with time-resolved and spectral discrimination using a near-IR detector, Anal. Chem, 75:2280-2291 (2003).

Castro, et al., Single-molecule electrophoresis, Anal. Chem., 67:3181-3186 (1995).

Chen, et al., Single-molecule detection in capillary electrophoresis: molecular shot noise as a fundamental limit to chemical analysis, Anal. Chem., 68:690-696 (1996).

Guide to Amine-Reactive Probes. Revised Oct. 13, 2005; 1-9.

Peck, et al., Single-molecule fluorescence detection: autocorrelation criterion and experimental realization with phycoerythrim, Proc. Natl. Acad. Sci, 86:4087-4091 (1989).

U.S. Appl. No. 60/613,881, entitled "Continuous wave single particle detector," filed Sep. 28, 2004, Puskas.

U.S. Appl. No. 60/624,785, entitled "Sandwich assay for detection of individual molecules," filed Oct. 29, 2004, Puskas.

U.S. Appl. No. 11/784,186, entitled "Methods and Compositions for Highly Sensitive Analysis of Markers," filed Apr. 4, 2007, Goix, Philippe J.

U.S. Appl. No. 12/060,997, entitled: "Methods and Compositions for Highly Sensitive Analysis of Markers," filed on Apr. 2, 2008, Goix, Philippe J. et al.

Cohen et al.: "The renal TGF-beta system in the db/db mouse model of diabetic nephropathy" Exp. Nephrol. (1998) vol. 6 pp. 226-233.

Eder et al.: "Transforming growth factor-beta1 and beta2 in serum and urine from patients with bladder carcinoma" The J. of Urology (1996) Vol. 156 pp. 953-957.

Eskelinen et al.: "A new tumor marker MCA in breast cancer diagnosis" Anticancer Res. (1988) vol. 8 pp. 665-668.

Kaiser et al.: "Capillary electrophoresis coupled to mass spectrometer for automated and robust polypeptide determination in body fluids for clinical use" Electrophoresis (2004) V. 25 pp. 2044-2055.

Lecaptain et al.: "Characterization of DNA-protein complex by capillary electrophoresis-single molecule fluorescence correlation spectroscopy," Analyst (2001) vol. 126, pp. 1279-1284.

Schiffer et al.: "High resolution proteome/peptidome analysis of body fluids by capillary electrophoresis coupled with MS" Proteomics (2006) V. 6 pp. 5615-5627.

Von Zur Muhlen et al.: "Evaluation of Urine Proteome Pattern Analysis for Its Potential to Reflect Coronary Artery Atherosclerosis in Symptomatic Patients" J. Proteom. Res. (2009) V. 8 pp. 335-345.

Zimmerli et al.: "Urinary Proteomic Biomakers in Coronary Artery Disease" Mol. Cell Proteomics (Feb. 2008) vol. 7, No. 2 pp. 290-298. First Published on Oct. 19, 2007.

* cited by examiner

SCANNING ANALYZER FOR SINGLE MOLECULE DETECTION AND METHODS OF USE

CROSS-REFERENCE

This application is a divisional of U.S. application Ser. No. 12/338,955, filed Dec. 18, 2008, now U.S. Pat. No. 7,914,734, which claims the benefit of U.S. Provisional Application No. 61/015,142, filed Dec. 19, 2007, which application is incorporated herein by reference.

BACKGROUND

Advances in biomedical research, medical diagnosis, prognosis, monitoring and treatment selection, bioterrorism detection, and other fields involving the analysis of multiple samples of low volume and concentration of analytes have led to development of sample analysis systems capable of sensitively detecting particles in a sample at ever-decreasing concentrations. U.S. Pat. Nos. 4,793,705 and 5,209,834 describe previous systems that achieved extremely sensitive detection. The present invention provides further development in this field.

SUMMARY OF THE INVENTION

Provided herein is a single molecule analyzer comprising: (a) an electromagnetic radiation source for providing electromagnetic radiation to a sample container that comprises a sample; (b) a system for directing the electromagnetic radiation from the electromagnetic radiation source to an interrogation space in the sample; (c) a translating system for translating the interrogation space through at least a portion of the sample, thereby forming a moveable interrogation space; and (d) a detector operably connected to the interrogation space to detect electromagnetic radiation emitted from a single molecule in the interrogation space if the molecule is present. In some embodiments, the single molecule analyzer has a translating system wherein the translating system is capable of translating the interrogation space in one or more of a linear and a non-linear path. In some embodiments, the non-linear path is substantially a circular path. In some embodiments, the non-linear path is substantially a helical pattern. In some embodiments, the non-linear path is substantially a raster pattern. In some embodiments, the single molecule analyzer described herein further comprises a container with a surface adapted and configured for containing and confining at least one sample on the surface. In some embodiments, the container is a plate. In further embodiments, the plate is a microliter plate.

In some embodiments of the single molecule analyzer, the interrogation space has an effective volume of more than about 1 $\mu m^3$, more than about 2 $\mu m^3$, more than about 3 $\mu m^3$, more than about 4 $\mu m^3$, more than about 5 $\mu m^3$, more than about 10 $\mu m^3$, more than about 15 $\mu m^3$, more than about 30 $\mu m^3$, more than about 50 $\mu m^3$, more than about 75 $\mu m^3$, more than about 100 $\mu m^3$, more than about 150 $\mu m^3$, more than about 200 $\mu m^3$, more than about 250 $\mu m^3$, more than about 300 $\mu m^3$, more than about 400 $\mu m^3$, more than about 450 $\mu m^3$, more than about 500 $\mu m^3$, more than about 550 $\mu m^3$, more than about 600 $\mu m^3$, more than about 750 $\mu m^3$, more than about 1000 $\mu m^3$, more than about 2000 $\mu m^3$, more than about 4000 $\mu m^3$, more than about 6000 $\mu m^3$, more than about 8000 $\mu m^3$, more than about 10000 $\mu m^3$, more than about 12000 $\mu m^3$, more than about 13000 $\mu m^3$, more than about 14000 $\mu m^3$, more than about 15000 $\mu m^3$, more than about 20000 $m^3$, more than about 30000 $\mu m^3$, more than about 40000 $\mu m^3$, or more than about 50000 $\mu m^3$. In some embodiments, the interrogation space is of a volume less than about 50000 $\mu m^3$, less than about 40000 $\mu m^3$, less than about 30000 $\mu m^3$, less than about 20000 $\mu m^3$, less than about 15000 $\mu m^3$, less than about 14000 $\mu m^3$, less than about 13000 $\mu m^3$, less than about 12000 $\mu m^3$, less than about 11000 $\mu m^3$, less than about 9500 $\mu m^3$, less than about 8000 $\mu m^3$, less than about 6500 $\mu m^3$, less than about 6000 $\mu m^3$, less than about 5000 $\mu m^3$, less than about 4000 $\mu m^3$, less than about 3000 $\mu m^3$, less than about 2500 $\mu m^3$, less than about 2000 $\mu m^3$, less than about 1500 $\mu m^3$, less than about 1000 $\mu m^3$, less than about 800 $\mu m^3$, less than about 600 $\mu m^3$, less than about 400 $\mu m^3$, less than about 200 $\mu m^3$, less than about 100 $\mu m^3$, less than about 75 $\mu m^3$, less than about 50 $\mu m^3$, less than about 25 $\mu m^3$, less than about 20 $\mu m^3$, less than about 15 $\mu m^3$, less than about 14 $\mu m^3$, less than about 13 $\mu m^3$, less than about 12 $\mu m^3$, less than about 11 $\mu m^3$, less than about 10 $\mu m^3$, less than about 5 $\mu m^3$, less than about 4 $\mu m^3$, less than about 3 $\mu m^3$, less than about 2 $\mu m^3$, or less than about 1 $\mu m^3$. In some embodiments, the volume of the interrogation space is between about 1 $\mu m^3$ and about 10000 $\mu m^3$. In some embodiments, the interrogation space is between about 1 $\mu m^3$ and about 1000 $\mu m^3$. In some embodiments, the interrogation space is between about 1 $\mu m^3$ and about 100 $\mu m^3$. In some embodiments, the interrogation space is between about 1 $\mu m^3$ and about 50 $\mu m^3$. In some embodiments the interrogation space is between about 1 $\mu m^3$ and about 10 $\mu m^3$. In some embodiments, the interrogation space is between about 2 $\mu m^3$ and about 10 $\mu m^3$. In some embodiments, the interrogation space is between about 3 $\mu m^3$ and about 7 $\mu m^3$. In some embodiments, the interrogation space is between about 15 $\mu m^3$ and about 11000 $\mu m^3$. In some embodiments, the interrogation space is between about 200 $\mu m^3$ and about 3000 $\mu m^3$. In some embodiments, the interrogation space is between about 500 $\mu m^3$ and about 600 $\mu m^3$.

In some embodiments of the single molecule analyzer, the single molecules are attached to the surface of the container. In some embodiments, the single molecules are attached to the surface of the container by a noncovalent bond. In a further embodiment, the noncovalent bonds are formed between the molecules and antibodies that are covalently or non-covalently bound to the surface of the container. In a further embodiment, the noncovalent bonds are formed between the molecules and antibodies located on the surface of the container. In some embodiments, the single molecule analyzer further comprises a microscope objective wherein a depth of field of the microscope objective and a lateral extent of the laser beam together define the interrogation space. In some embodiments, the depth of field and a diameter of the aperture imaged to the microscope objective together define the interrogation space. In some embodiments, the microscope objective is adapted and configured to collect the electromagnetic radiation emitted from a single molecule located within the interrogation space. In some embodiments, the interrogation space is capable of being translated through a portion of a sample. In some embodiments, the translating system is constructed and arranged to translate through the portion of sample more than one time. In some embodiments, the translating system is constructed and arranged to translate through a same portion of sample a first time and a second time at a sufficiently slow speed as to allow a molecule of interest that is detected the first time the interrogation space is translated through the portion of sample to substantially diffuse out of the portion of sample after the first time the portion of sample is interrogated by the interrogation space, and to further allow a subsequent molecule of interest, if present, to substantially diffuse into the portion of sample the second time the portion of sample is interrogated by the interrogation space. In some embodiments, the translating system is constructed and arranged to translate the interrogation space such that the detection spot returns to the portion of sample after sufficient time has passed so that molecules detected in the first pass can diffuse out of the portion, and other molecules can diffuse into the portion. In some embodiments, the single molecule analyzer further comprises a system capable of translating the interrogation space in a substantially circular pattern. In such an embodiment, the system is capable of translating the interrogation space at a speed of between about 100 and about 1000 RPM. In some embodiments, the scan speed of the interrogation space is more than 100 RPM. In some embodiments, the scan speed of the interrogation space is more than 300 RPM. In some embodiments, the scan speed of the interrogation space is more than 500 RPM. In some embodiments, the scan speed of the interrogation space is more than 700 RPM. In some embodiments, the scan speed of the interrogation space is more than 900 RPM. In some embodiments, the scan speed of the interrogation space is less than 1000 RPM. In some embodiments, the scan speed of the interrogation space is less than 800 RPM. In some embodiments, the scan speed of the interrogation space is less than 600 RPM. In some embodiments, the scan speed of the interrogation space is less than 400 RPM. In some embodiments, the scan speed of the interrogation space is less than 200 RPM. In some embodiments, the scan speed of the interrogation space is between about 100 RPM and about 1000 RPM. In some embodiments, the scan speed of the interrogation space is between about 200 RPM and about 900 RPM. In some embodiments, the scan speed of the interrogation space is between about 300 RPM and about 800 RPM. In some embodiments, the scan speed of the interrogation space is between about 400 RPM and about 700 RPM. In some embodiments, the scan speed of the interrogation space is between about 450 RPM and about 600 RPM. In some embodiments, the scan speed of the interrogation space is between about 450 RPM and about 550 RPM.

In some embodiments, the single molecule analyzer is adapted and configured to sequentially detect the presence or absence of a single molecule of a particular type in a first sample, and detect the presence or absence of a single molecule of the type in a second sample, wherein there is no carryover between the first and the second sample.

Further provided herein is a microtiter plate comprising: (a) a base comprising a material substantially transparent to light of wavelengths between 550 nm and 800 nm and comprising one or more portions that are of thickness such that an image can be formed on a first side of the portion by a high numerical aperture lens positioned on a second side of the portion and wherein no part of the image is formed within the base; and (b) a surface adapted and configured for containing and confining at least one fluid sample on the surface. In some embodiments, the base is transparent to light of wavelengths between 600 nm and 750 nm. In some embodiments, the base is transparent to light of wavelengths between 630 nm and 740 nm. In some embodiments, the base is transparent to light of wavelengths between 630 nm and 640 nm. In some embodiments, the plate surface comprises a series of microwells. In some embodiments, the plate comprises a material that emits less fluorescence than polystyrene.

Further provided herein is an instrument capable of sequentially detecting the presence or absence of a single molecule of a particular type in a first sample, and detecting the presence or absence of a single molecule of the type in a second sample, wherein the instrument is adapted and configured so that there is no carryover between the first and the second sample.

Further provided herein is a method of sequentially detecting the presence or absence of a single molecule of a particular type in a first sample, and detecting the presence or absence of a single molecule of the type in a second sample, wherein there is no carryover between the first and the second sample. In some embodiments a single molecule of interest is detected in the first sample and the second sample wherein the first sample and the second sample are contained and confined in a non-disposable apparatus.

Provided herein is a method for detecting the presence or absence of a single molecule in a sample comprising: (a) directing electromagnetic radiation from an electromagnetic radiation source to an interrogation space in the sample; (b) detecting the presence or absence of a first single molecule in the interrogation space located at a first position in the sample; (c) translating the interrogation space through the sample to a subsequent position in the sample; (d) detecting the presence or absence of a subsequent single molecule in the subsequent position in the sample; and (e) repeating steps (c) and (d) as required to detect the presence or absence of a single molecule in more than one position of the sample. In some embodiments of this invention, the interrogation space has an effective volume of more than about 1 $\mu m^3$, more than about 2 $\mu m^3$, more than about 3 $\mu m^3$, more than about 4 $\mu m^3$, more than about 5 $\mu m^3$, more than about 10 $\mu m^3$, more than about 15 $\mu m^3$, more than about 30 $\mu m^3$, more than about 50 $\mu m^3$, more than about 75 $\mu m^3$, more than about 100 $\mu m^3$, more than about 150 $\mu m^3$, more than about 200 $\mu m^3$, more than about 250 $\mu m^3$, more than about 300 $\mu m^3$, more than about 400 $\mu m^3$, more than about 450 $\mu m^3$, more than about 500 $\mu m^3$, more than about 550 $\mu m^3$, more than about 600 $\mu m^3$, more than about 750 $\mu m^3$, more than about 1000 $\mu m^3$, more than about 2000 $\mu m^3$, more than about 4000 $\mu m^3$, more than about 6000 $\mu m^3$, more than about 8000 $\mu m^3$, more than about 10000 $\mu m^3$, more than about 12000 $\mu m^3$, more than about 13000 $\mu m^3$, more than about 14000 $\mu m^3$, more than about 15000 $\mu m^3$, more than about 20000 $\mu m^3$, more than about 30000 $\mu m^3$, more than about 40000 $\mu m^3$, or more than about 50000 $\mu m^3$. In some embodiments, the volume of the interrogation space is less than about 50000 $\mu m^3$, less than about 40000 $\mu m^3$, less than about 30000 $\mu m^3$, less than about 20000 $\mu m^3$, less than about 15000 $\mu m^3$, less than about 14000 $\mu m^3$, less than about 13000 $\mu m^3$, less than about 12000 $\mu m^3$, less than about 11000 $\mu m^3$, less than about 9500 $\mu m^3$, less than about 8000 $\mu m^3$, less than about 6500 $\mu m^3$, less than about 6000 $\mu m^3$, less than about 5000 $\mu m^3$, less than about 4000 $\mu m^3$, less than about 3000 $\mu m^3$, less than about 2500 $\mu m^3$, less than about 2000 $\mu m^3$, less than about 1500 $\mu m^3$, less than about 1000 $\mu m^3$, less than about 800 $\mu m^3$, less than about 600 $\mu m^3$, less than about 400 $\mu m^3$, less than about 200 $\mu m^3$, less than about 100 $\mu m^3$, less than about 75 $\mu m^3$, less than about 50 $\mu m^3$, less than about 25 $\mu m^3$, less than about 20 $\mu m^3$, less than about 15 $\mu m^3$, less than about 14 $\mu m^3$, less than about 13 $\mu m^3$, less than about 12 $\mu m^3$, less than about 11 $\mu m^3$, less than about 10 $\mu m^3$, less than about 5 $\mu m^3$, less than about 4 $\mu m^3$, less than about 3 $\mu m^3$, less than about 2 $\mu m^3$, or less than about 1 $\mu m^3$. In some embodiments, the volume of the interrogation space is between about 1 $\mu m^3$ and about 10000 $\mu m^3$. In some embodiments, the interrogation space is between about 1 $\mu m^3$ and about 1000 $\mu m^3$. In some embodiments, the interrogation space is between about 1 $\mu m^3$ and about 100 $\mu m^3$. In some embodiments the interrogation space is between about 1 $\mu m^3$ and about 50 $\mu m^3$. In some embodiments the interrogation space is between about 1 $\mu m^3$ and about 10 $\mu m^3$. In some embodiments, the interrogation space is between about 2 μm³ and about 10 μm³. In some embodiments, the interrogation space is between about 3 μm³ and about 7 μm³. In some embodiments, the interrogation space is between about 15 μm³ and about 11000 μm³. In some embodiments, the interrogation space is between about 200 μm³ and about 3000 μm³. In some embodiments, the interrogation space is between about 500 μm³ and about 600 μm³.

In some embodiments of the method, the interrogation space is translated in a non-linear path. In a further embodiment, the non-linear path comprises a substantially circular path. In a further embodiment, the non-linear path comprises a substantially helical path. In a further embodiment, the sample remains substantially stationary relative to the electromagnetic radiation directed at the interrogation space located within the sample. In some embodiments, the sample is translated in the x-y axis and the electromagnetic radiation source is kept substantially static. In some embodiments, both the electromagnetic radiation and the sample are translated relative to each other. In some embodiments, the interrogation space is translated through the first position of sample more than one time. In some embodiments, the interrogation space is translated through the first position of sample a subsequent time at a sufficiently slow speed as to allow a molecule of interest, if present, detected the first time the interrogation space is translated through the position of sample to substantially diffuse out of the position of sample after the first time the position of sample is interrogated by the interrogation space and to further allow a subsequent molecule of interest, if present, to substantially diffuse into the position of sample the second time the position of sample is interrogated by the interrogation space. In some embodiments, the interrogation space is translated such that the detection spot returns to the first position of sample after sufficient time has passed so that molecules detected in the first pass can diffuse out of the position, and other molecules can diffuse into the position. some embodiments, the method further comprising the steps of sequentially detecting the presence or absence of a single molecule of a particular type in the sample, then detecting the presence or absence of a single molecule of the same type in a second sample, wherein there is no carryover between the first and the second sample. In some embodiments of the method, the first sample and the second sample are contained and confined in a non-disposable apparatus.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

I. Introduction

Figure 1A:
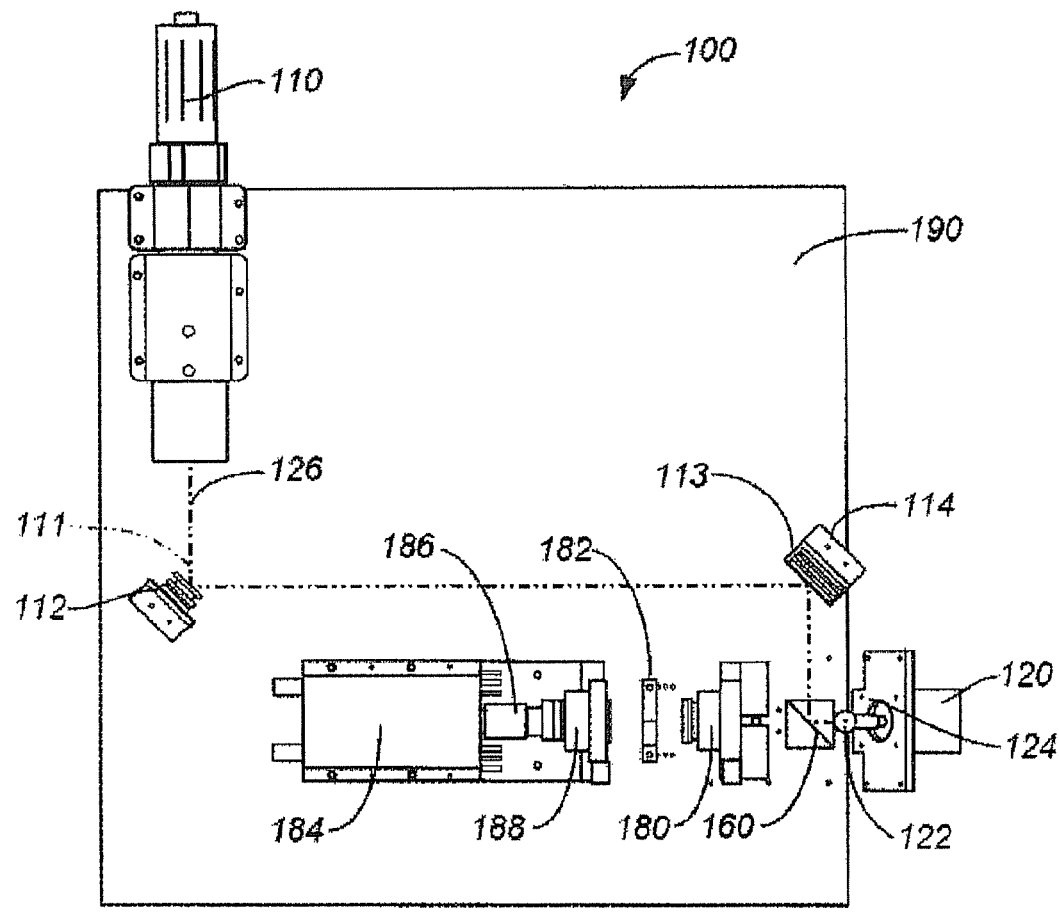
FIG. 1A illustrates the scanning single molecule analyzer as viewed from the top.

The invention provides instruments, kits, compositions, and methods for the highly sensitive detection of single molecules, and for the determination of the concentration of the molecules in a sample. In some embodiments, the sensitivity and precision of the instruments, compositions, methods, and kits of the invention can be achieved by a combination of factors selected from, but not limited to, electromagnetic sources of appropriate wavelength and power output, appropriate interrogation space size, high numerical aperture lenses, detectors capable of detecting single photons, and data analysis systems for counting single molecules. The instruments of the invention are referred to as "single molecule detectors" or "single particle detectors," and are also encompassed by the terms "single molecule analyzers" and "single particle analyzers." The sensitivity and precision of the kits and methods of the invention are achieved in some embodiments by the use of the instruments of the invention together with a combination of factors selected from, but not limited to, labels for molecules that exhibit characteristics that allow the molecules to be detected at the level of the single molecule, and methods assaying the label in the instruments described herein.

The instruments, kits, and methods of the invention are especially useful in the sensitive and precise detection of single molecules or small molecules, and for the determination of the concentration of the molecules in a sample.

The invention provides, in some embodiments, instruments and kits for the sensitive detection and determination of concentration of molecules by detection of single molecules, labels for such detection and determination, and methods using such instruments and labels in the analysis of samples. In particular, the sensitivity and precision of the instruments, kits, and methods of the invention make possible the detection and determination of concentration of molecules, e.g., markers for biological states, at extremely low concentrations, e.g., concentrations below about 100, 10, 1, 0.1, 0.01, or 0.001 femtomolar. In further embodiments, the instruments and kits of the invention are capable of determining a concentration of a species in a sample, e.g., the concentration of a molecule, over a large dynamic range of concentrations without the need for dilution or other treatment of samples, e.g., over a concentration range of more than $10^5$-fold, $10^6$-fold, or $10^7$-fold.

The high sensitivity of the instruments, kits, and methods of the invention allows the use of markers, e.g., biological markers, which were not previously useful because of a lack of sensitivity of detection. The high sensitivity of the instruments, kits, and methods of the invention also facilitate the establishment of new markers. There are numerous markers currently available which could be useful in determining biological states, but are not currently of practical use because of current limitations in measuring their lower concentration ranges. In some cases, abnormally high levels of the marker are detectable by current methods, but normal ranges are unknown. In some cases, abnormally high levels of the marker are detectable by current methods, but normal ranges have not been established. In some cases, upper normal ranges of the marker are detectable, but not lower normal ranges, or levels below normal. In some cases, e.g., markers of cancer or infection, any level of the marker can indicate the presence of a biological state, and enhancing sensitivity of detection is an advantage for early diagnosis. In some cases, the rate of change, or lack of change, in the concentration of a marker over multiple time points provides the most useful information, but present methods of analysis do not permit time point sampling in the early stages of a condition when it is typically most treatable. In some cases, the marker can be detected at clinically useful levels only through the use of cumbersome methods that are not practical or useful in a clinical setting, such as methods that require complex sample treatment and time-consuming analysis. In addition, there are potential markers of biological states with sufficiently low concentration that their presence remains extremely difficult or impossible to detect by current methods.

The analytical methods and compositions of the present invention provide levels of sensitivity, precision, and robustness that allow the detection of markers for biological states at concentrations at which the markers have been previously undetectable, thus allowing the "repurposing" of such markers from confirmatory markers, or markers useful only in limited research settings, to diagnostic, prognostic, treatment-directing, or other types of markers useful in clinical settings and/or in large scale clinical settings, including clinical trials. Such methods allow the determination of normal and abnormal ranges for such markers.

The markers thus repurposed can be used for, e.g., detection of normal state (normal ranges), detection of responder/non-responder (e.g., to a treatment, such as administration of a drug); detection of early disease or pathological occurrence (e.g., early detection of cancer, early detection of cardiac ischemia); disease staging (e.g., cancer); disease monitoring (e.g., diabetes monitoring, monitoring for cancer recurrence after treatment); study of disease mechanism; and study of treatment toxicity, such as toxicity of drug treatments.

The invention thus provides methods and compositions for the sensitive detection of markers, and further methods of establishing values for normal and abnormal levels of markers. In further embodiments, the invention provides methods of diagnosis, prognosis, and/or treatment selection based on values established for the markers. The invention also provides compositions for use in such methods, e.g., detection reagents for the ultrasensitive detection of markers.

II. Instruments and System for Scanning Analyzer System

The methods of the invention utilize scanning analyzers, e.g., single molecule detectors. Such single molecule detectors include embodiments as hereinafter described.

A. Apparatus/System

In one aspect, the system and methods described herein utilize a scanning analyzer system capable of detecting a single molecule in a sample. In one embodiment, the scanning analyzer system is capable of providing electromagnetic radiation from an electromagnetic radiation source to a sample located within a sample container. The single molecule analyzer includes a system for directing the electromagnetic radiation from the electromagnetic radiation source to an interrogation space in the sample. The single molecule analyzer also includes a translating system for translating the interrogation space through at least a portion of the sample, thereby forming a moveable interrogation space. In some embodiments, the detector of the single molecule analyzer is operably connected to the interrogation space of the single molecule analyzer such that it detects radiation emitted from a single molecule in the interrogation space if the molecule is present.

In one aspect, the scanning analyzer system includes an electromagnetic radiation source for exciting a single molecule labeled with a fluorescent label. In one embodiment, the electromagnetic radiation source of the analyzer system is a laser. In a further embodiment, the electromagnetic radiation source is a continuous wave laser.

In a typical embodiment, the electromagnetic radiation source excites a fluorescent moiety attached to a label as the interrogation space encounters the label. In some embodiments, the fluorescent label moiety includes one or more fluorescent dye molecules. In some embodiments, the fluorescent label moiety is a quantum dot. Any suitable fluorescent moiety as described herein can be used as a label.

In a typical embodiment, the scanning analyzer system includes a system for directing the electromagnetic radiation to an interrogation space in the sample. In some embodiments, the concentration of the sample is such that the interrogation space is unlikely to contain more than one single molecule of interest; e.g., the interrogation space contains zero or one single molecule of interest in most cases. The interrogation space can then be moved through the sample to detect single molecules located throughout the sample. In a typical embodiment, electromagnetic radiation from the electromagnetic radiation source excites a fluorescent moiety attached to a label as the electromagnetic radiation, and the interrogation space into which the electromagnetic radiation is directed, is moved through the sample.

Typically, the scanning analyzer system further includes a translating system for translating the interrogation space through at least a portion of the sample, thereby forming a moveable interrogation space. The moveable interrogation space can detect multiple single molecules of interest located in different portions of the sample.

The interrogation space passes over the label and subsequently the label emits a detectable amount of energy when excited by the electromagnetic radiation source. In a typical embodiment, the single molecule analyzer contains a detector operably connected to the interrogation space to detect electromagnetic radiation emitted from a single molecule in the interrogation space. The electromagnetic radiation detector is capable of detecting the energy emitted by the label, e.g., by the fluorescent moiety of the label.

B. Scanning Single Molecule Analyzer

Figure 1B:
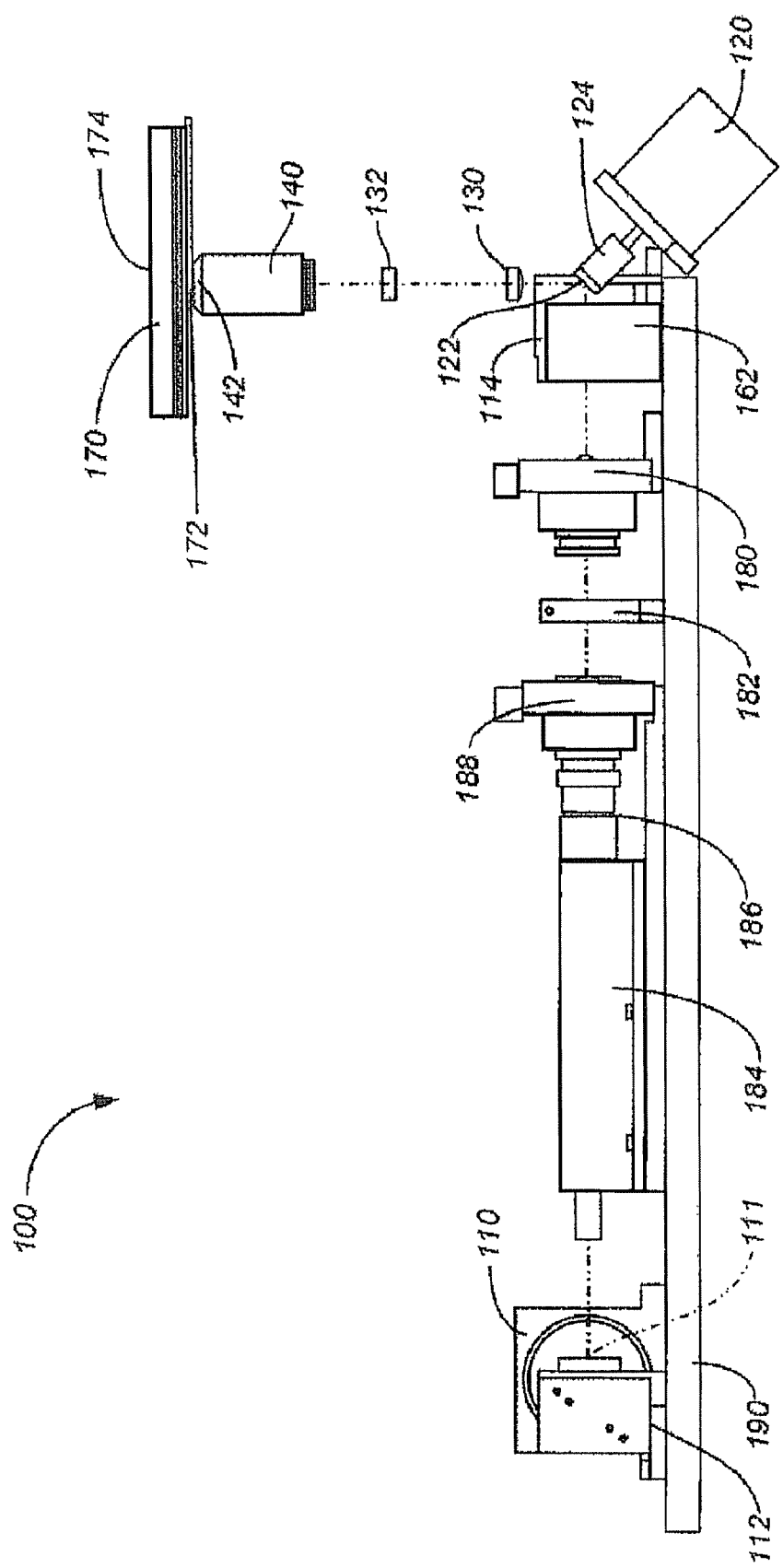
FIG. 1B illustrates the scanning single molecule analyzer as viewed from the side.

As shown in FIGS. 1A and 1B, described herein is one embodiment of a scanning analyzer system 100. The analyzer system 100 includes electromagnetic radiation source 110, a first alignment mirror 112, a second alignment mirror 114, a dichroic mirror 160, a rotating scan mirror 122 mounted to the shaft 124 of a scan motor 120. As shown in FIG. 1B, the rotating scan mirror 122 deflects the electromagnetic radiation source through a first scan lens 130, through a second scan lens 132, and through a microscope objective lens 140, to a sample plate 170. The fluorescence associated with the single molecules located on the sample plate 170 is detected using a tube lens 180, an aperture 182, a detector filter 188, a detector lens 186, and a detector 184. The signal is then processed by a processor (not shown) operatively coupled to the detector 184. In some embodiments, the entire scanning analyzer system 100 is mounted to a baseboard 190.

In operation the electromagnetic radiation source 110 is aligned so that its output 126, e.g., a beam, is reflected off the front surface 111 of a first alignment mirror 112 to the front surface 113 of a second alignment mirror 114 to the dichroic mirror 160 mounted to a dichroic mirror mount 162. The dichroic mirror 160 then reflects the electromagnetic radiation 126 to the front surface of a scan mirror 122 located at the tip of the shaft 124 of the scan motor 120. The electromagnetic radiation 126 then passes through a first scan lens 130 and a second scan lens 132 to the microscope objective lens 140. The objective lens 140 focuses the beam 126 through the base 174 of the sample plate 170 and directs the beam 126 to an interrogation space located on the opposite side of the sample plate 170 from which the beam 126 entered. Passing the electromagnetic radiation beam 126 through a first scan lens 130 and a second scan lens 132 ensures all light to the objective lens 140 is coupled efficiently. The beam 126 excites the label attached to the single molecule of interest located on the sample plate 170. The label emits radiation that is collected by the objective 140. The electromagnetic radiation is then passed back through the scan lenses 130,132 which then ensure coupling efficiency of the radiation from the objective 140. The detected radiation is reflected off of the front surface of the scan mirror 122 to the dichroic mirror 160. Because the fluorescent light detected is different than the color of the electromagnetic radiation source 110, the fluorescent light passing the dichroic mirror 160 passes through a tube lens 180, an aperture 182, a detector filter 188 and detector lens 186 to a detector 184. The detector filter 188 minimizes aberrant noise signals due to light scatter or ambient light while maximizing the signal emitted by the excited fluorescent moiety bound to the particle. A processor processes the light signal from the particle according to the methods described herein.

In a preferred embodiment, the microscope objective 140 has a numerical aperture. As used herein, "high numerical aperture lens" includes a lens with a numerical aperture of equal to or greater than 0.6. The numerical aperture is a measure of the number of highly diffracted image-forming light rays captured by the objective. A higher numerical aperture allows increasingly oblique rays to enter the objective lens and thereby produce a more highly resolved image. The brightness of an image also increases with higher numerical aperture. High numerical aperture lenses are commercially available from a variety of vendors, and any one lens having a numerical aperture of equal to or greater than approximately 0.6 can be used in the analyzer system. In some embodiments, the lens has a numerical aperture of about 0.6 to about 1.3. In some embodiments, the lens has a numerical aperture of about 0.6 to about 1.0. In some embodiments, the lens has a numerical aperture of about 0.7 to about 1.2. In some embodiments, the lens has a numerical aperture of about 0.7 to about 1.0. In some embodiments, the lens has a numerical aperture of about 0.7 to about 0.9. In some embodiments, the lens has a numerical aperture of about 0.8 to about 1.3. In some embodiments, the lens has a numerical aperture of about 0.8 to about 1.2. In some embodiments, the lens has a numerical aperture of about 0.8 to about 1.0. In some embodiments, the lens has a numerical aperture of at least about 0.6. In some embodiments, the lens has a numerical aperture of at least about 0.7. In some embodiments, the lens has a numerical aperture of at least about 0.8. In some embodiments, the lens has a numerical aperture of at least about 0.9. In some embodiments, the lens has a numerical aperture of at least about 1.0. In some embodiments, the aperture of the microscope objective lens 140 is approximately 1.25.

The high numerical aperture (NA) microscope objective that is required typically when performing single molecule detection through the walls or the base of the sample plate 170 has short working distances. The working distance is the distance from the front of the lens to the object in focus. The objective in some embodiments must be within 350 microns of the object. In some embodiments, where a microscope objective lens 140 with NA of 0.8 is used, an Olympus 40×/0.8 NA water immersion objective (Olympus America, Inc., USA) can be used. This objective has a 3.3 mm working distance. In some embodiments, an Olympus 60×/0.9 NA water immersion objective with a 2 mm working distance can be used. Because the later lens is a water immersion lens, the space 142 between the objective and the sample must be filled with water. This can be accomplished using a water bubbler (not shown) or some other suitable plumbing for depositing water between the objective and the base of the sample plate.

In all embodiments, the electromagnetic radiation source is set so that the wavelength of the laser is sufficient to excite the fluorescent label attached to the particle. In some embodiments, the electromagnetic radiation source 110 is a laser that emits light in the visible spectrum. In some embodiments, the laser is a continuous wave laser with a wavelength of 639 nm. In other embodiments, the laser is a continuous wave laser with wavelength of 532 nm. In other embodiments, the laser is a continuous wave laser with a wavelength of 422 nm. In other embodiments, the laser is a continuous wave laser with a wavelength of 405 nm. Any continuous wave laser with a wavelength suitable for exciting a fluorescent moiety as used in the methods and compositions of the invention can be used without departing from the scope of the invention.

In a single molecule analyzer system 100, as the interrogation space passes over the labeled single molecule, the beam 126 of the electromagnetic radiation source directed into the interrogation space causes the label to enter an excited state. When the particle relaxes from its excited state, a detectable burst of light is emitted. In the length of time it takes for the interrogation space to pass over the particle, the excitation-emission cycle is repeated many times by each particle. This allows the analyzer system 100 to detect tens to thousands of photons for each particle as the interrogation space passes over the particle. Photons emitted by the fluorescent particles are registered by the detector 184 with a time delay indicative of the time for the interrogation space to pass over the labeled particle. The photon intensity is recorded by the detector 184 and the sampling time is divided into bins, wherein the bins are uniform, arbitrary time segments with freely selectable time channel widths. The number of signals contained in each bin is evaluated. One or more of several statistical analytical methods are used to determine when a particle is present. These methods include determining the baseline noise of the analyzer system and determining signal strength for the fluorescent label at a statistical level above baseline noise to mitigate false positive signals from the detector.

1. Electromagnetic Radiation Source

Some embodiments of the analyzer system use a chemiluminescent label. These embodiments may not require an EM source for particle detection. In other embodiments, the extrinsic label or intrinsic characteristic of the particle is light-interacting, such as a fluorescent label or light-scattering label. In such an embodiment, a source of EM radiation is used to illuminate the label and/or the particle. EM radiation sources for excitation of fluorescent labels are preferred.

In some embodiments, the analyzer system consists of an electromagnetic radiation source 110. Any number of radiation sources can be used in a scanning analyzer system 100 without departing from the scope of the invention. Multiple sources of electromagnetic radiation have been previously disclosed and are incorporated by reference from previous U.S. patent application Ser. No. 11/048,660. In some embodiments, different continuous wave electromagnetic (EM) radiation sources emit electromagnetic radiation at the same wavelengths. In other embodiments, different sources emit different wavelengths of EM radiation.

In one embodiment, the EM source 110 is a continuous wave laser producing wavelengths of between 200 nm and 1000 nm. Continuous wave lasers provide continuous illumination without accessory electronic or mechanical devices, such as shutters, to interrupt their illumination. Such EM sources have the advantage of being small, durable and relatively inexpensive. In addition, they generally have the capacity to generate larger fluorescent signals than other light sources. Specific examples of suitable continuous wave EM sources include, but are not limited to: lasers of the argon, krypton, helium-neon, helium-cadmium types, as well as, tunable diode lasers (red to infrared regions), each with the possibility of frequency doubling. In an embodiment where a continuous wave laser is used, an electromagnetic radiation source of 3 mW may have sufficient energy to excite a fluorescent label. A beam of such energy output can be between 2 to 5 µm in diameter. When exposed at 3 mW, a labeled particle can be exposed to the laser beam for about 1 msec. In alternate embodiments, the particle can be exposed to the laser beam at equal to or less than about 500 µsec. In an alternate embodiment, the time of exposure can be equal to or less than about 100 µsec. In an alternate embodiment, the time of exposure can be equal to or less than about 50 µsec. In an alternate embodiment, the time of exposure can be equal to or less than about 10 µsec.

Light-emitting diodes (LEDs) are another low-cost, highly reliable illumination source. Advances in ultra-bright LEDs and dyes with high absorption cross-section and quantum yield have made LEDs applicable for single molecule detection. Such LED light can be used for particle detection alone or in combination with other light sources such as mercury arc lamps, elemental arc lamps, halogen lamps, arc discharges, plasma discharges, and any combination of these.

In one embodiment, the EM source comprises a pulse wave laser. In such an embodiment, the pulse size, size, focus spot, and total energy emitted by the laser must be sufficient to excite the fluorescent label. In some embodiments, a laser pulse of less than 1 nanosecond can be used. A pulse of this duration can be preferable in some pulsed laser applications. In other embodiments, a laser pulse of 1 nanosecond can be used. In other embodiments, a laser pulse of 2 nanoseconds can be used. In other embodiments, a laser pulse of 3 nanoseconds can be used. In other embodiments, a laser pulse of 4 nanoseconds can be used. In other embodiments, a laser pulse of 5 nanoseconds can be used. In still other embodiments, a pulse of between 2 to 5 nanoseconds can be used. In other embodiments, a pulse of longer duration can be used.

The optimal laser intensity depends on the photo bleaching characteristics of the single dyes and the length of time required to traverse the interrogation space (including the speed of the particle, the distance between interrogation spaces if more than one is used and the size of the interrogation space(s)). To obtain a maximal signal, the sample can be illuminated at the highest intensity that will not photo bleach a high percentage of the dyes. The preferred intensity is such that no more that 5% of the dyes are bleached by the time the particle has traversed the interrogation space.

The power of the laser is set depending on the type of dye molecules and the length of time the dye molecules are stimulated. The power can also depend on the speed that the interrogation space passes through the sample. Laser power is defined as the rate at which energy is delivered by the beam and is measured in units of Joules/second, or Watts. To provide a constant amount of energy to the interrogation space as the particle passes through, the less time the laser can illuminate the particle as the power output of the laser is increased. In some embodiments, the combination of laser power and illumination time is such that the total energy received by the interrogation space during the time of illumination is more than about 0.1, 0.5, 1, 2, 3, 4, 5, 6, 7, 8, 9, 10, 12, 15, 20, 25, 30, 35, 40, 45, 50, 60, 70, 80, 90, or 100 microJoule. In some embodiments, the combination of laser power and illumination time is such that the total energy received by the interrogation space during the time of illumination is less than about 0.5, 1, 2, 3, 4, 5, 6, 7, 8, 9, 10, 12, 15, 20, 25, 30, 35, 40, 45, 50, 60, 70, 80, 90, 100, or 110 microJoule. In some embodiments, the combination of laser power and illumination time is such that the total energy received by the interrogation space during the time of illumination is between about 0.1 and 100 microJoule. In some embodiments, the combination of laser power and illumination time is such that the total energy received by the interrogation space during the time of illumination is between about 1 and 100 microJoule. In some embodiments, the combination of laser power and illumination time is such that the total energy received by the interrogation space during the illumination time is between about 1 and 50 microJoule. In some embodiments, the combination of laser power and illumination time is such that the total energy received by the interrogation space during the time of illumination is between about 2 and 50 microJoule. In some embodiments, the combination of laser power and illumination time is such that the total energy received by the interrogation space during the time of illumination is between about 3 and 60 microJoule. In some embodiments, the combination of laser power and illumination time is such that the total energy received by the interrogation space during the time of illumination is between about 3 and 50 microJoule. In some embodiments, the combination of laser power and illumination time is such that the total energy received by the interrogation space during the time of illumination is between about 3 and 40 microJoule. In some embodiments, the combination of laser power and illumination time is such that the total energy received by the interrogation space during the time of illumination is between about 3 and 30 microJoule. In some embodiments, the combination of laser power and illumination time is such that the total energy received by the interrogation space during the time of illumination is about 1 microJoule. In some embodiments, the combination of laser power and illumination time is such that the total energy received by the interrogation space during the time of illumination is about 3 microJoule. In some embodiments, the combination of laser power and illumination time is such that the total energy received by the interrogation space during the time of illumination is about 5 microJoule. In some embodiments, the combination of laser power and illumination time is such that the total energy received by the interrogation space during the time of illumination is about 10 microJoule. In some embodiments, the combination of laser power and illumination time is such that the total energy received by the interrogation space during the time of illumination is about 15 microJoule. In some embodiments, the combination of laser power and illumination time is such that the total energy received by the interrogation space during the time of illumination is about 20 microJoule. In some embodiments, the combination of laser power and illumination time is such that the total energy received by the interrogation space during the time of illumination is about 30 microJoule. In some embodiments, the combination of laser power and illumination time is such that the total energy received by the interrogation space during the time of illumination is about 40 microJoule. In some embodiments, the combination of laser power and illumination time is such that the total energy received by the interrogation space during the time of illumination is about 50 microJoule. In some embodiments, the combination of laser power and illumination time is such that the total energy received by the interrogation space during the time of illumination is about 60 microJoule. In some embodiments, the combination of laser power and illumination time is such that the total energy received by the interrogation space during the time of illumination is about 70 microJoule. In some embodiments, the combination of laser power and illumination time is such that the total energy received by the interrogation space during the time of illumination is about 80 microJoule. In some embodiments, the combination of laser power and illumination time is such that the total energy received by the interrogation space during the time of illumination is about 90 microJoule. In some embodiments, the combination of laser power and time of illumination is such that the total energy received by the interrogation space during the time of illumination is about 100 microJoule.

In some embodiments, the laser power output is set to at least about 1 mW, 2 mW, 3 mW, 4 mW, 5 mW, 6 mW, 7 mW, 8 mW, 9 mW, 10 mW, 13 mW, 15 mW, 20 mW, 25 mW, 30 mW, 40 mW, 50 mW, 60 mW, 70 mW, 80 mW, 90 mW, 100 mW, or more than 100 mW. In some embodiments, the laser power output is set to at least about 1 mW. In some embodiments, the laser power output is set to at least about 3 mW. In some embodiments, the laser power output is set to at least about 5 mW. In some embodiments, the laser power output is set to at least about 10 mW. In some embodiments, the laser power output is set to at least about 15 mW. In some embodiments, the laser power output is set to at least about 20 mW. In some embodiments, the laser power output is set to at least about 30 mW. In some embodiments, the laser power output is set to at least about 40 mW. In some embodiments, the laser power output is set to at least about 50 mW. In some embodiments, the laser power output is set to at least about 60 mW. In some embodiments, the laser power output is set to at least about 90 mW.

The time that the laser illuminates the interrogation space can be set to no less than about 1, 2, 3, 4, 5, 10, 15, 20, 30, 40, 50, 60, 70, 80, 90, 100, 150, 200, 250, 300, 350, 400, 450, 500, 600, 700, 800, 900, or 1000 microseconds. The time that the laser illuminates the interrogation space can be set to no more than about 2, 3, 4, 5, 10, 15, 20, 30, 40, 50, 60, 70, 80, 90, 100, 150, 200, 250, 300, 350, 400, 450, 500, 600, 700, 800, 900, 1000, 1500, or 2000 microseconds. The time that the laser illuminates the interrogation space can be set between about 1 and 1000 microseconds. The time that the laser illuminates the interrogation space can be set between about 5 and 500 microseconds. The time that the laser illuminates the interrogation space can be set between about 5 and 100 microseconds. The time that the laser illuminates the interrogation space can be set between about 10 and 100 microseconds. The time that the laser illuminates the interrogation space can be set between about 10 and 50 microseconds. The time that the laser illuminates the interrogation space can be set between about 10 and 20 microseconds. The time that the laser illuminates the interrogation space can be set between about 5 and 50 microseconds. The time that the laser illuminates the interrogation space can be set between about 1 and 100 microseconds. In some embodiments, the time that the laser illuminates the interrogation space is about 1 microsecond. In some embodiments, the time that the laser illuminates the interrogation space is about 5 microseconds. In some embodiments, the time that the laser illuminates the interrogation space is about 10 microseconds. In some embodiments, the time that the laser illuminates the interrogation space is about 25 microseconds. In some embodiments, the time that the laser illuminates the interrogation space is about 50 microseconds. In some embodiments, the time that the laser illuminates the interrogation space is about 100 microseconds. In some embodiments, the time that the laser illuminates the interrogation space is about 250 microseconds. In some embodiments, the time that the laser illuminates the interrogation space is about 500 microseconds. In some embodiments, the time that the laser illuminates the interrogation space is about 1000 microseconds.

In some embodiments, the laser illuminates the interrogation space for 1 millisecond, 250 microseconds, 100 microseconds, 50 microseconds, 25 microseconds or 10 microseconds with a laser that provides a power output of 3 mW, 4 mW, 5 mW, or more than 5 mW. In some embodiments, a label is illuminated with a laser that provides a power output of 3 mW and illuminates the label for about 1000 microseconds. In other embodiments, a label is illuminated for less than 1000 milliseconds with a laser providing a power output of not more than about 20 mW. In other embodiments, the label is illuminated with a laser power output of 20 mW for less than or equal to about 250 microseconds. In some embodiments, the label is illuminated with a laser power output of about 5 mW for less than or equal to about 1000 microseconds.

2. Optical Scanning System

The scanning analyzer system described herein is different than traditional single molecule analyzers previously described elsewhere. In flow cytometry and other methods of fluorescence spectroscopy, a sample flows through an interrogation space. In contrast, the interrogation space in the analyzer provided herein is moved relative to the sample. This can be done by fixing the sample container relative to the instrument and moving the electromagnetic radiation beam. Alternatively, the electromagnetic radiation beam can be fixed and the sample plate moved relative to the beam. In some embodiments, a combination of both can be used. In an embodiment wherein the sample plate is translated to create the moveable interrogation space, the limiting factor is the ability to move the plate smoothly enough so that the sample located on the sample plate is not jarred and the interrogation space is in the desired location.

In one embodiment, the electromagnetic radiation source 110 is focused onto a sample plate 170 of the analyzer system 100. The beam 126 from the continuous wave electromagnetic radiation source 110 is optically focused through the base of the sample plate to a specified depth plane within the sample located on the sample plate 170. Optical scanning of the sample can be accomplished using mirrors or lenses. In some embodiments, a mirror 122 is mounted on the end of a scan motor shaft 124 of the scan motor 120 but is tilted at a slight angle relative to the shaft 124. In some embodiments, as the mirror 122 turns, it can deflect the electromagnetic radiation beam 126 thereby creating a small circle. By placing the mirror 122 between the objective 140 and the dichroic mirror 160, the spot at the focus of the objective can move around the sample. In some embodiments, the sample is scanned in a circular pattern. In such an embodiment, a scan circle with a diameter of between about 500 µm and about 750 µm can be formed. In some embodiments, a scan circle with a diameter of between about 550 µm and 700 µm can be formed. In some embodiments, a scan circle with a diameter of between about 600 µm and 650 µm can be formed. In some embodiments a scan circle with a diameter of about 630 µm can be formed. In some embodiments, when a scan circle with a diameter of 630 µm is used, the scan circle can be traversed at about 8 revolutions per second (or about 500 RPM), equivalent to pumping the sample through a flow source at a rate of about 5 µl/min. In some embodiments, the scan speed of the interrogation space is more than 100 RPM. In some embodiments, the scan speed of the interrogation space is more than 300 RPM. In some embodiments, the scan speed of the interrogation space is more than 500 RPM. In some embodiments, the scan speed of the interrogation space is more than 700 RPM. In some embodiments, the scan speed of the interrogation space is more than 900 RPM. In some embodiments, the scan speed of the interrogation space is less than 1000 RPM. In some embodiments, the scan speed of the interrogation space is less than 800 RPM. In some embodiments, the scan speed of the interrogation space is less than 600 RPM. In some embodiments, the scan speed of the interrogation space is less than 400 RPM. In some embodiments, the scan speed of the interrogation space is less than 200 RPM. In some embodiments, the scan speed of the interrogation space is between about 100 RPM and about 1000 RPM. In some embodiments, the scan speed of the interrogation space is between about 200 RPM and about 900 RPM. In some embodiments, the scan speed of the interrogation space is between about 300 RPM and about 800 RPM. In some embodiments, the scan speed of the interrogation space is between about 400 RPM and about 700 RPM. In some embodiments, the scan speed of the interrogation space is between about 450 RPM and about 600 RPM. In some embodiments, the scan speed of the interrogation space is between about 450 RPM and about 550 RPM. With the development of improved electronics and optics, scanning in the z-axis may be required in addition to scanning in a two-dimensional pattern to avoid duplicate scanning of the same molecule. In some of the embodiments previously mentioned, the optical scanning pattern allows the scanning of a substantially different volume each time a portion of the sample is scanned.

Figure 2:
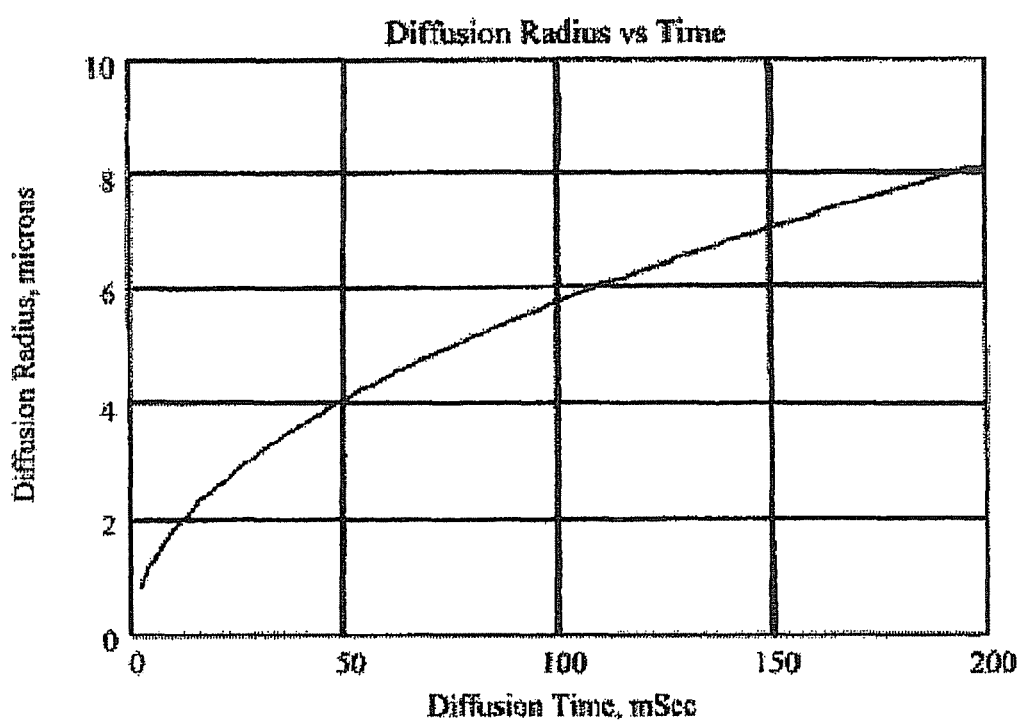
FIG. 2 depicts a graph showing the diffusion time for a 155 KDa molecular weight molecule as a function of the diffusion radius of the molecule.

In some embodiments, the sample is scanned by an electromagnetic radiation source wherein the electromagnetic radiation interrogates a portion of the sample. A single molecule of interest may or may not be present in the interrogation space. In some embodiments, a portion of the sample is scanned a first time and then subsequently scanned a second time. In some embodiments the same portion of sample is scanned multiple times. In some embodiments, the sample is scanned such that the detection spot returns to a portion of sample a second time after sufficient time has passed so that the molecules detected in the first pass have drifted or diffused out of the portion, and other molecules have drifted or diffused into the portion. When the same portion of sample is scanned at least one or more times, the scanning speed can be slow enough to allow molecules to diffuse into, and out of, the space being interrogated. In some embodiments, the interrogation space is translated through a same portion of sample a first time and a second time at a sufficiently slow speed as to allow a molecule of interest that is detected the first time the interrogation space is translated through the portion of sample to substantially diffuse out of the portion of sample after the first time the portion of sample is interrogated by the interrogation space, and to further allow a subsequent molecule of interest, if present, to substantially diffuse into the portion of sample the second time the portion of sample is interrogated by the interrogation space. FIG. 2 shows a graph of the diffusion time versus corresponding diffusion radius for molecules with a 155 KDa molecular weight. As used herein, "diffusion radius" refers to the standard deviation of the distance from the starting point that the molecule will most likely diffuse in the time indicated on the X-axis.

In some embodiments an alternative scan pattern is used. In some embodiments, the scan pattern can approximate an arc. In some embodiments, the scan pattern comprises at least one 90 degree angle. In some embodiments, the scan pattern comprises at least one angle less than 90 degrees. In some embodiments, the scan pattern comprises at least one angle that is more than 90 degrees. In some embodiments, the scan pattern is substantially sinusoidal. In some embodiments, the optical scanning can be done with one mirror as previously described. In an alternative embodiment, the optical scanning can be done with at least two mirrors. Multiple mirrors allow scanning in a straight line, as well as allowing the system to scan back and forth, so that a serpentine pattern is created. Alternatively, a multiple mirror optical scanning configuration allows for scanning in a raster pattern.

In an alternative embodiment, optical scanning can be done using an optical wedge. A wedge scanner provides a circular scan pattern and shortens the optical path because scan lenses are not required. An optical wedge approximates a prism with a very small angle. The optical wedge can be mounted to the shaft of the electromagnetic radiation source. The optical wedge rotates to create an optical scan pattern. In an alternative embodiment, the scan mirror can be mounted using an electro-mechanical mount. In such an embodiment, the electro-mechanical mount would have two voice coils. One voice coil would cause displacement of the mirror in a vertical direction. The other voice coil would cause displacement of the mirror in a horizontal direction. Using this embodiment, any scan pattern desired can be created.

In some embodiments, the scanning particle analyzer scans the sample located in the sample plate in a two-dimensional orientation, e.g., following the x-y plane of the sample. In some embodiments, the sample can be scanned in a three-dimensional orientation consisting of scanning in an x-y plane and z direction. In some embodiments, the sample can be scanned along the x-y and z directions simultaneously. For example, the sample can be scanned in a helical pattern. In some embodiments, the sample can be scanned in the z direction only.

In some embodiments, a scan lens (130 as shown in FIGS. 1A & 1B) can re-direct the scanning optical path to the pupil of the objective. The scan lens focuses the image of the optical axis on the scan mirror to the exit pupil of the objective. The scan lens ensures that the scanning beam remains centered on the objective, despite the distance between the scan mirror and the microscope objective, thus improving the image and light collection efficiency of the scanning beam.

3. Interrogation Space

The invention described herein encompasses the use of an interrogation space, which can be thought of as an effective volume of sample in which a single molecule of interest can be detected when present. Although there are various ways to calculate the interrogation space of the sample, the simplest method for determining the effective volume (V) of the interrogation space is to calculate the effective cross section of the detection volume. Because the detection volume is typically swept through the sample by translating the detection volume through the stationary sample, the volume is typically the result of the cross sectional area of the detection volume being swept through some distance during the time of measurement. If the sample concentration (C) is known and the number of molecules detected (N) during a period of time is known, then the sample volume consists of the number of molecules detected divided by the concentration of the sample, or V=N/C (where the sample concentration has units of molecules per unit volume).

For example, in some embodiments of the system described herein, all photons detected are counted and added up in 1 msec segments (photon counting bins). If a molecule of interest is present in the 1 msec segment, the count of photons detected is typically significantly higher than background. Therefore, the distance the detection volume has moved with respect to the sample is the appropriate distance to use to calculate the volume sampled in a single segment, i.e., the interrogation space. In this example, if the sample is analyzed for 60 seconds, then effectively 60,000 segments are scanned. If the effective volume is divided by the number of segments, the resulting volume is in essence the volume of a single segment, i.e., the interrogation space. Mathematically, the volume of the single segment, i.e., the interrogation space volume (Vs), equals the number of molecules detected (N) divided by the concentration of the sample multiplied by the number of segment bins (C·n—where n represents the number of segment bins during the time the N number of molecules were counted). For exemplary purposes only, consider that a known standard of one femtomolar concentration is run through 60,000 segments, and 20 molecules of the standard are detected. Accordingly, the interrogation space volume, Vs, equals N/(C·n) or 20/(602.214·6E4), or 553.513 $\mu m^3$. Thus, in this example, the interrogation space volume, which is the effective volume for one sample corresponding to one photon counting bin, is 553.513 $\mu m^3$.

In addition, from the interrogation volume described previously, the cross sectional area of the sample segment can be approximated using a capillary flow system with similar optics to the invention described herein. The cross section area (A) is approximated by dividing the interrogation volume (Vs) by the distance (t) the detection segment moves. The distance (t) the detection segment moves is given by i·r·s/x, where t a function of the flow rate (r), the viscosity of the sample (i), the segment bin time (s), and the cross section of the capillary (x). For exemplary purposes only, consider a bin time (s) of 1 msec, a flow rate (r) of 5 $\mu L/min$, a viscosity factor (i) of 2, and a capillary cross sectional area (x) of 10,000 $\mu m^2$. Accordingly, the distance the interrogation space moves (t) is given by i·r·s/x, or (2·5 $\mu L/min$·1E-3 sec)/(10,000 $\mu m^2$), or 16.7 $\mu m$. The effective cross sectional area (A) of the detector spot can further be calculated as Vs/t, or (553.513 $\mu m^3$)/(16.7 $\mu m$), or 33 $\mu m^2$. Note that both the value of the interrogation volume, Vs, and the cross sectional area of the interrogation volume depend on the binning time.

The lower limit on the size of the interrogation space is bounded by the wavelengths of excitation energy currently available. The upper limit of the interrogation space size is determined by the desired signal-to-noise ratios—the larger the interrogation space, the greater the noise from, e.g., Raman scattering. In some embodiments, the volume of the interrogation space is more than about 1 $\mu m^3$, more than about 2 $\mu m^3$, more than about 3 $\mu m^3$, more than about 4 $\mu m^3$, more than about 5 $\mu m^3$, more than about 10 $\mu m^3$, more than about 15 $\mu m^3$, more than about 30 $\mu m^3$, more than about 50 $\mu m^3$, more than about 75 $\mu m^3$, more than about 100 $\mu m^3$, more than about 150 $\mu m^3$, more than about 200 $\mu m^3$, more than about 250 $\mu m^3$, more than about 300 $\mu m^3$, more than about 400 $\mu m^3$, more than about 500 $\mu m^3$, more than about 550 $\mu m^3$, more than about 600 $\mu m^3$, more than about 750 $\mu m^3$, more than about 1000 $\mu m^3$, more than about 2000 $\mu m^3$, more than about 4000 $\mu m^3$, more than about 6000 $\mu m^3$, more than about 8000 $\mu m^3$, more than about 10000 $\mu m^3$, more than about 12000 $\mu m^3$, more than about 13000 $\mu m^3$, more than about 14000 $\mu m^3$, more than about 15000 $\mu m^3$, more than about 20000 $\mu m^3$, more than about 30000 $\mu m^3$, more than about 40000 $\mu m^3$, or more than about 50000 $\mu m^3$. In some embodiments, the interrogation space is of a volume less than about 50000 $\mu m^3$, less than about 40000 $\mu m^3$, less than about 30000 $\mu m^3$, less than about 20000 $\mu m^3$, less than about 15000 $\mu m^3$, less than about 14000 $\mu m^3$, less than about 13000 $\mu m^3$, less than about 12000 $\mu m^3$, less than about 11000 $\mu m^3$, less than about 9500 $\mu m^3$, less than about 8000 $\mu m^3$, less than about 6500 $\mu m^3$, less than about 6000 $\mu m^3$, less than about 5000 $\mu m^3$, less than about 4000 $\mu m^3$, less than about 3000 $\mu m^3$, less than about 2500 $\mu m^3$, less than about 2000 $\mu m^3$, less than about 1500 $\mu m^3$, less than about 1000 $\mu m^3$, less than about 800 $\mu m^3$, less than about 600 $\mu m^3$, less than about 400 $\mu m^3$, less than about 200 $\mu m^3$, less than about 100 $\mu m^3$, less than about 75 $\mu m^3$, less than about 50 $\mu m^3$, less than about 25 $\mu m^3$, less than about 20 $\mu m^3$, less than about 15 $\mu m^3$, less than about 14 $\mu m^3$, less than about 13 $\mu m^3$, less than about 12 $\mu m^3$, less than about 11 $\mu m^3$, less than about 10 $\mu m^3$, less than about 5 $\mu m^3$, less than about 4 $\mu m^3$, less than about 3 $\mu m^3$, less than about 2 $\mu m^3$, or less than about 1 $\mu m^3$. In some embodiments, the volume of the interrogation space is between about 1 $\mu m^3$ and about 10000 $\mu m^3$. In some embodiments, the interrogation space is between about 1 $\mu m^3$ and about 1000 $\mu m^3$. In some embodiments, the interrogation space is between about 1 $\mu m^3$ and about 100 $\mu m^3$. In some embodiments, the interrogation space is between about 1 $\mu m^3$ and about 50 $\mu m^3$. In some embodiments, the interrogation space is between about 1 $\mu m^3$ and about 10 $\mu m^3$. In some embodiments, the interrogation space is between about 2 $\mu m^3$ and about 10 $\mu m^3$. In some embodiments, the interrogation space is between about 3 $\mu m^3$ and about 7 $\mu m^3$.

4. Sample Plate

Some embodiments of the invention described herein use a sample plate 170 to hold the sample being detected for a single molecule of interest. The sample plate in some embodiments is a microtiter plate. The microtiter plate consists of a base 172 and a top surface 174. The top surface 174 of the microtiter plate in some embodiments consists of at least one well for containing a sample of interest. In some embodiments, the microtiter plate consists of a plurality of wells to contain a plurality of samples. The system described herein is sensitive enough so that only a small sample size is needed. In some embodiments the sample size can be less than approximately 100 $\mu l$. In some embodiments, the sample size can be less than approximately 10 $\mu l$. In some embodiments, the sample size can be less than approximately 1 $\mu l$. In some embodiments, the sample is less than approximately 0.1 $\mu l$. In some embodiments, the sample size is less than approximately 0.001 $\mu l$. The microtiter plate in some embodiments can be one constructed using microfabrication techniques. In some embodiments, the top surface of the plate can be smooth. The sample can be sized so that the sample is self-contained by the surface tension of the sample itself. In such an embodiment, the sample forms a droplet on the surface of the plate. In some embodiments, the sample can then be scanned for a molecule of interest.

Typically, the sample is scanned through the sample plate material, e.g., through the walls of the microwells. In some embodiments, the sample is scanned through the base of the sample plate. In some embodiments, the base of the sample plate is made of a material that is transparent to light. In some embodiments, the base of the sample plate is made of a material that is transparent to electromagnetic radiation. The sample plate is transparent to an excitation wavelength of interest. Using a transparent material allows the wavelength of the excitation beam to pass through the sample plate and excite the molecule of interest or the fluorescent label conjugated to the molecule of interest. The transparency of the plate further allows the detector to detect the emissions from the excited molecules of interest. In some embodiments, the base material is substantially transparent to light of wavelengths between 550 nm and 800 nm. In some embodiments, the base material is substantially transparent to light of wavelengths between 600 nm and 700 nm. In some embodiments, the material of the plate is transparent to light of wavelength between 620 nm and 680 nm. In some embodiments, the material of the plate is transparent to light of wavelengths between 630 nm and 660 nm. In some embodiment, the material of the plate is transparent to light of wavelength between 630 nm and 640 nm.

The thickness of the sample plate is also considered. The sample is scanned by an electromagnetic radiation source that passes through a portion of the material of the plate. The thickness of the plate allows an image to be formed on a first side of the portion of the plate that is scanned by a high numerical aperture lens that is positioned on a second side of the portion of the plate that is scanned. Such an embodiment facilitates the formation of an image within the sample and not within the base. The image formed corresponds to the interrogation space of the system. The image should be formed at the depth of the single molecule of interest. As previously mentioned, the thickness of the plate depends on the working distance and depth of field of the lens that is used. Commercial plates available are typically 650 microns thick.

The plate can be made out of any suitable material that allows the excitation energy to pass through the plate. In some embodiments the plate is made of polystyrene. In some embodiments, the plate is made of polycarbonate. In some embodiments, the plate is made of polyethylene. In some embodiments, a commercially available plate can be used, such as a NUNC™ brand plate. Any plate made of a suitable material and of a suitable thickness can be used. In preferred embodiments, the plate is made out of a material with low fluorescence, thereby reducing background fluorescence. For example, a preferred material may emit less fluorescence than a plate made from polystyrene. Background fluorescence resulting from the plate material can be further avoided by minimizing the thickness of the plate.

In some embodiments, the sample consists of a small volume of fluid that can contain a particular type of molecule. In such an embodiment, the single molecule of interest, if present, can be detected and counted in a location anywhere in the fluid volume. In some embodiments, scanning the sample comprises scanning a smaller concentrated sample. In such an embodiment, the optical scanning can occur at the surface of the sample plate, for example, if the highest concentration of molecules is located at the surface of the sample plate. This can occur if the single molecules are adsorbed to the surface of the plate or if they are bound to antibodies or other binding molecules adhered to the surface of the plate. When antibodies are used to capture a single molecule of interest, the antibodies can be applied to the surface of the sample plate, e.g., to the bottom of a microwell(s). The single molecule of interest then binds to the antibodies located within the microwell. In some embodiments, an elution step is done to remove the bound single molecule of interest. The presence or absence of the unbound molecules can then be detected in a smaller sample volume. In some embodiments wherein the elution step is done, the single molecules may or may not be attached to paramagnetic beads. If no beads are used, the elution buffer can be added to the sample well and the presence or absence of the single molecule of interest can be detected. In some embodiments, a paramagnetic bead is used as a capture bead to capture the single molecule of interest.

In some embodiments of the scanning single molecule analyzer described herein, the electromagnetic (EM) radiation source is directed to the sample interrogation space without passing through the material of the sample plate. Image formation occurs in the sample on the same side as the beam directed to the sample. In such an embodiment, a water immersion lens can be used but is not required to image the sample through the air-liquid interface. In zero carryover systems wherein the objective does not come in contact with the sample, sample carryover between samples does not occur.

5. Detectors

In one embodiment, light emitted by a fluorescent label after exposure to electromagnetic radiation is detected. The emitted light can be, e.g., ultra-violet, visible or infrared. Referring to FIGS. 1A & 1B, the detector 184 (or other embodiments) can capture the amplitude and duration of photon bursts from a fluorescent moiety, and convert the amplitude and duration of the photon bursts to electrical signals. Detection devices such as CCD cameras, video input module cameras, and Streak cameras can be used to produce images with contiguous signals. Other embodiments use devices such as a bolometer, a photodiode, a photodiode array, avalanche photodiodes, and photomultipliers which produce sequential signals. Any combination of the aforementioned detectors can be used.

Several distinct characteristics of the emitted electromagnetic radiation between an interrogation space and its corresponding detector 180, can be detected including: emission wavelength, emission intensity, burst size, burst duration, and fluorescence polarization. In some embodiments, the detector 180 is a photodiode used in reverse bias. Such a photodiode set usually has an extremely high resistance. This resistance is reduced when light of an appropriate frequency shines on the P/N junction. Hence, a reverse biased diode can be used as a detector by monitoring the current running through it. Circuits based on this effect are more sensitive to light than circuits based on zero bias.

In one embodiment of the analyzer system, the photodiode can be an avalanche photodiode. These photodiodes can be operated with much higher reverse bias than conventional photodiodes, thus allowing each photo-generated carrier to be multiplied by avalanche breakdown. This results in internal gain within the photodiode, thereby increasing the effective responsiveness and sensitivity of the device. The choice of photodiode is determined by the energy or emission wavelength emitted by the fluorescently labeled particle. In some embodiments, the detector is an avalanche photodiode detector that detects energy between 300 nm and 1700 nm. In another embodiment, silicon avalanche photodiodes can be used to detect wavelengths between 300 nm and 1100 nm. In another embodiment, the photodiode is an indium gallium arsenide photodiode that detects energy in the range of 800-2600 nm. In another embodiment, indium gallium arsenic photodiodes can be used to detect wavelengths between 900 nm and 1700 nm. In some embodiments, the photodiode is a silicon photodiode that detects energy in the range of 190-1100 nm. In another embodiment, the photodiode is a germanium photodiode that detects energy in the range of 800-1700 nm. In yet other embodiments, the photodiode is a lead sulfide photodiode that detects energy in the range of between less than 1000 nm to 3500 nm. In some embodiments, the avalanche photodiode is a single-photon detector designed to detect energy in the 400 nm to 1100 nm wavelength range. Single photon detectors are commercially available (for example Perkin Elmer, Wellesley, Mass.).

In some embodiments, an analyzer system can comprise at least one detector. In other embodiments, the analyzer system can comprise at least two detectors, and each detector can be chosen and configured to detect light energy at a specific wavelength range. For example, two separate detectors can be used to detect particles tagged with different labels, which emit photons with energy in different spectra upon excitation with an EM source. In one embodiment, an analyzer system can comprise a first detector that can detect fluorescent energy in the range of 450-700 nm such as that emitted by a green dye (e.g., Alexa Fluor 546), and a second detector that can detect fluorescent energy in the range of 620-780 nm such as that emitted by a far-red dye (e.g., Alexa Fluor 647). Other embodiments use detectors for detecting fluorescent energy in the range of 400-600 nm such as that emitted by blue dyes (e.g., Hoechst 33342), and for detecting energy in the range of 560-700 nm such as that emitted by red dyes (e.g., Alexa Fluor 546 and Cy3).

A system comprising two or more detectors can be used to detect individual particles that are each tagged with two or more labels emitting light in different spectra. For example, two different detectors can detect an antibody that has been tagged with two different dye labels. Alternatively, an analyzer system comprising two detectors can be used to detect particles of different types, each type being tagged with a different dye molecule, or with a mixture of two or more dye molecules. For example, two different detectors can be used to detect two different types of antibodies that recognize two different proteins, each type being tagged with a different dye label or with a mixture of two or more dye label molecules. By varying the proportion of the two or more dye label molecules, two or more different particle types can be individually detected using two detectors. It is understood that three or more detectors can be used without departing from the scope of the invention.

It should be understood by one skilled in the art that one or more detectors can be configured at each interrogation space, whether one or more interrogation spaces are defined within a flow cell, and that each detector can be configured to detect any of the characteristics of the emitted electromagnetic radiation listed above. The use of multiple detectors, e.g., for multiple interrogation spaces, has been previously disclosed in a prior application and is incorporated by reference herein from U.S. patent application Ser. No. 11/048,660. Once a particle is labeled to render it detectable (or if the particle possesses an intrinsic characteristic rendering it detectable), any suitable detection mechanism known in the art can be used without departing from the scope of the present invention, for example a CCD camera, a video input module camera, a Streak camera, a bolometer, a photodiode, a photodiode array, avalanche photodiodes, and photomultipliers producing sequential signals, and combinations thereof. Different characteristics of the electromagnetic radiation can be detected including: emission wavelength, emission intensity, burst size, burst duration, fluorescence polarization, and any combination thereof.

III. Molecules for Single Molecule Detection

The instruments, kits and methods of the invention can be used for the sensitive detection and determination of concentration of a number of different types of single molecules. In particular, the instruments, kits, and methods are useful in the sensitive detection and determination of concentration of markers of biological states. "Detection of a single molecule," as that term is used herein, refers to both direct and indirect detection. For example, a single molecule can be labeled with a fluorescent label, and the molecule-label complex detected in the instruments described herein. Alternatively, a single molecule can be labeled with a fluorescent label, then the fluorescent label is detached from the single molecule, and the label detected in the instruments described herein. The term detection of a single molecule encompasses both forms of detection.

A. General

Examples of molecules that can be detected using the analyzer and related methods of the present invention include: biopolymers such as proteins, nucleic acids, carbohydrates, and small molecules, both organic and inorganic. In particular, the instruments, kits, and methods described herein are useful in the detection of single molecules of proteins and small molecules in biological samples, and the determination of concentration of such molecules in the sample.

The terms "protein," "polypeptide," "peptide," and "oligopeptide," are used interchangeably herein and include any composition that includes two or more amino acids joined together by a peptide bond. It will be appreciated that polypeptides can contain amino acids other than the 20 amino acids commonly referred to as the 20 naturally occurring amino acids. Also, polypeptides can include one or more amino acids, including the terminal amino acids, which are modified by any means known in the art (whether naturally or non-naturally). Examples of polypeptide modifications include e.g., by glycosylation, or other-post-translational modification. Modifications which can be present in polypeptides of the present invention, include, but are not limited to: acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The molecules detected by the present instruments, kits, and methods can be free or can be part of a complex, e.g., an antibody-antigen complex, or more generally a protein-protein complex, e.g., complexes of troponin or complexes of prostate specific antigen (PSA).

B. Markers of Biological States

In some embodiments, the invention provides compositions and methods for the sensitive detection of biological markers, and for the use of such markers in diagnosis, prognosis, and/or determination of methods of treatment.

Markers of the present invention can be, for example, any composition and/or molecule or a complex of compositions and/or molecules that is associated with a biological state of an organism (e.g., a condition such as a disease or a non-disease state). A marker can be, for example, a small molecule, a polypeptide, a nucleic acid, such as DNA and RNA, a lipid, such as a phospholipid or a micelle, a cellular component such as a mitochondrion or chloroplast, etc. Markers contemplated by the present invention can be previously known or unknown. For example, in some embodiments, the methods herein can identify novel polypeptides that can be used as markers for a biological state of interest or condition of interest, while in other embodiments, known polypeptides are identified as markers for a biological state of interest or condition. Using the systems of the invention it is possible that one can observe those markers, e.g., polypeptides with high potential use in determining the biological state of an organism, but that are only present at low concentrations, such as those "leaked" from diseased tissue. Other high potentially useful markers or polypeptides can be those that are related to the disease, for instance, those that are generated in the tumor-host environment. Any suitable marker that provides information regarding a biological state can be used in the methods and compositions of the invention. A "marker," as that term is used herein, encompasses any molecule that can be detected in a sample from an organism and whose detection or quantitation provides information about the biological state of the organism.

Biological states include but are not limited to phenotypic states; conditions affecting an organism; states of development; age; health; pathology; disease detection, process, or staging; infection; toxicity; or response to chemical, environmental, or drug factors (such as drug response phenotyping, drug toxicity phenotyping, or drug effectiveness phenotyping).

The term "organism" as used herein refers to any living being comprised of a least one cell. An organism can be as simple as a one cell organism or as complex as a mammal. An organism of the present invention is preferably a mammal. Such mammal can be, for example, a human or an animal such as a primate (e.g., a monkey, chimpanzee, etc.), a domesticated animal (e.g., a dog, cat, horse, etc.), farm animal (e.g., goat, sheep, pig, cattle, etc.), or laboratory animal (e.g., mouse, rat, etc.). Preferably, an organism is a human.

In some embodiments, the methods and compositions of the invention are directed to classes of markers, e.g., cytokines, growth factors, oncology markers, markers of inflammation, endocrine markers, autoimmune markers, thyroid markers, cardiovascular markers, markers of diabetes, markers of infectious disease, neurological markers, respiratory markers, gastrointestinal markers, musculoskeletal markers, dermatological disorders, and metabolic markers.

Table 1, below, provides examples of these classes of markers that have been measured by the methods and compositions of the invention, and provides the concentration of the markers as detected by the methods and compositions of the invention and number of particles that are counted by the single molecule analyzer system of the invention for the particular marker.

TABLE 1

CLASSES OF MARKERS AND EXEMPLARY MARKERS IN THE CLASSES

| Cytokines | Molar Conc. | Molecules |
|---|---|---|
| IL-12 p70 | $2.02 \times 10^{-14}$ | $6.09 \times 10^{+5}$ |
| IL-10 | $5.36 \times 10^{-14}$ | $1.61 \times 10^{+6}$ |
| IL-1 alpha | $5.56 \times 10^{-14}$ | $1.67 \times 10^{+6}$ |
| IL-3 | $5.85 \times 10^{-14}$ | $1.76 \times 10^{+6}$ |
| IL-12 p40 | $6.07 \times 10^{-14}$ | $1.83 \times 10^{+6}$ |
| IL-1ra | $6.12 \times 10^{-14}$ | $1.84 \times 10^{+6}$ |
| IL-12 | $8.08 \times 10^{-14}$ | $2.44 \times 10^{+6}$ |
| IL-6 | $9.53 \times 10^{-14}$ | $2.87 \times 10^{+6}$ |
| IL-4 | $1.15 \times 10^{-13}$ | $3.47 \times 10^{+6}$ |
| IL-18 | $1.80 \times 10^{-13}$ | $5.43 \times 10^{+6}$ |
| IP-10 | $1.88 \times 10^{-13}$ | $1.13 \times 10^{+7}$ |
| IL-5 | $1.99 \times 10^{-13}$ | $5.98 \times 10^{+6}$ |
| Eotaxin | $2.06 \times 10^{-13}$ | $1.24 \times 10^{+7}$ |
| IL-16 | $3.77 \times 10^{-13}$ | $1.14 \times 10^{+7}$ |
| MIG | $3.83 \times 10^{-13}$ | $1.15 \times 10^{+7}$ |
| IL-8 | $4.56 \times 10^{-13}$ | $1.37 \times 10^{+7}$ |
| IL-17 | $5.18 \times 10^{-13}$ | $1.56 \times 10^{+7}$ |
| IL-7 | $5.97 \times 10^{-13}$ | $1.80 \times 10^{+7}$ |
| IL-15 | $6.13 \times 10^{-13}$ | $1.84 \times 10^{+7}$ |
| IL-13 | $8.46 \times 10^{-13}$ | $2.55 \times 10^{+7}$ |
| IL-2R (soluble) | $8.89 \times 10^{-13}$ | $2.68 \times 10^{+7}$ |
| IL-2 | $8.94 \times 10^{-13}$ | $2.69 \times 10^{+7}$ |
| LIF/HILDA | $9.09 \times 10^{-13}$ | $5.47 \times 10^{+7}$ |
| IL-1 beta | $1.17 \times 10^{-12}$ | $3.51 \times 10^{+7}$ |
| Fas/CD95/Apo-1 | $1.53 \times 10^{-12}$ | $9.24 \times 10^{+7}$ |
| MCP-1 | $2.30 \times 10^{-12}$ | $6.92 \times 10^{+7}$ |

TABLE 1-continued

CLASSES OF MARKERS AND EXEMPLARY MARKERS IN THE CLASSES

| Oncology | Molar Conc. | Molecules |
|---|---|---|
| EGF | $4.75 \times 10^{-14}$ | $2.86 \times 10^{+6}$ |
| TNF-alpha | $6.64 \times 10^{-14}$ | $8.00 \times 10^{+6}$ |
| PSA (3rd generation) | $1.15 \times 10^{-13}$ | $6.92 \times 10^{+6}$ |
| VEGF | $2.31 \times 10^{-13}$ | $6.97 \times 10^{+6}$ |
| TGF-beta1 | $2.42 \times 10^{-13}$ | $3.65 \times 10^{+7}$ |
| FGFb | $2.81 \times 10^{-13}$ | $1.69 \times 10^{+7}$ |
| TRAIL | $5.93 \times 10^{-13}$ | $3.57 \times 10^{+7}$ |
| TNF-RI (p55) | $2.17 \times 10^{-12}$ | $2.62 \times 10^{+8}$ |

| Inflammation | Molar Conc. | Molecules |
|---|---|---|
| ICAM-1 (soluble) | $8.67 \times 10^{-15}$ | $5.22 \times 10^{+4}$ |
| RANTES | $6.16 \times 10^{-14}$ | $3.71 \times 10^{+6}$ |
| MIP-2 | $9.92 \times 10^{-14}$ | $2.99 \times 10^{+6}$ |
| MIP-1 beta | $1.98 \times 10^{-13}$ | $5.97 \times 10^{+6}$ |
| MIP-1 alpha | $2.01 \times 10^{-13}$ | $6.05 \times 10^{+6}$ |
| MMP-3 | $1.75 \times 10^{-12}$ | $5.28 \times 10^{+7}$ |

| Endocrinology | Molar Conc. | Molecules |
|---|---|---|
| 17 beta-Estradiol (E2) | $4.69 \times 10^{-14}$ | $2.82 \times 10^{+6}$ |
| DHEA | $4.44 \times 10^{-13}$ | $2.67 \times 10^{+7}$ |
| ACTH | $1.32 \times 10^{-12}$ | $7.96 \times 10^{+7}$ |
| Gastrin | $2.19 \times 10^{-12}$ | $1.32 \times 10^{+8}$ |
| Growth Hormone (hGH) | $2.74 \times 10^{-12}$ | $1.65 \times 10^{+8}$ |

| Autoimmune | Molar Conc. | Molecules |
|---|---|---|
| GM-CSF | $1.35 \times 10^{-13}$ | $8.15 \times 10^{+6}$ |
| C-Reactive Protein (CRP) | $3.98 \times 10^{-13}$ | $2.40 \times 10^{+7}$ |
| G-CSF | $1.76 \times 10^{-12}$ | $1.06 \times 10^{+8}$ |

| Thyroid | Molar Conc. | Molecules |
|---|---|---|
| Cyclic AMP | $9.02 \times 10^{-15}$ | $5.43 \times 10^{+5}$ |
| Calcitonin | $3.25 \times 10^{-14}$ | $1.95 \times 10^{+6}$ |
| Parathyroid Hormone (PTH) | $1.56 \times 10^{-13}$ | $9.37 \times 10^{+6}$ |

| Cardiovascular | Molar Conc. | Molecules |
|---|---|---|
| B-Natriuretic Peptide | $2.86 \times 10^{-13}$ | $1.72 \times 10^{+7}$ |
| NT-proBNP | $2.86 \times 10^{-12}$ | $8.60 \times 10^{+7}$ |
| C-Reactive Protein, HS | $3.98 \times 10^{-13}$ | $2.40 \times 10^{+7}$ |
| Beta-Thromboglobulin (BTG) | $5.59 \times 10^{-13}$ | $3.36 \times 10^{+7}$ |

| Diabetes | Molar Conc. | Molecules |
|---|---|---|
| C-Peptide | $2.41 \times 10^{-15}$ | $1.45 \times 10^{+5}$ |
| Leptin | $1.89 \times 10^{-13}$ | $1.14 \times 10^{+7}$ |

| Infectious Dis. | Molar Conc. | Molecules |
|---|---|---|
| IFN-gamma | $2.08 \times 10^{-13}$ | $1.25 \times 10^{+7}$ |
| IFN-alpha | $4.55 \times 10^{-13}$ | $2.74 \times 10^{+7}$ |

| Metabolism | Molar Conc. | Molecules |
|---|---|---|
| Bio-Intact PTH (1-84) | $1.59 \times 10^{-12}$ | $1.44 \times 10^{+8}$ |
| PTH | $1.05 \times 10^{-13}$ | $9.51 \times 10^{+6}$ |

Cytokines

For both research and diagnostics, cytokines are useful as markers of a number of conditions, diseases, pathologies, and the like, and the compositions and methods of the invention include labels for detection and quantitation of cytokines and methods using such labels to determine normal and abnormal levels of cytokines, as well as methods of diagnosis, prognosis, and/or determination of treatment based on such levels.

There are currently over 100 cytokines/chemokines whose coordinate or discordant regulation is of clinical interest. In order to correlate a specific disease process with changes in cytokine levels, the ideal approach requires analyzing a sample for a given cytokine, or multiple cytokines, with high sensitivity. Exemplary cytokines that are presently used in marker panels and that can be used in methods and compositions of the invention include, but are not limited to, BDNF, CREB pS133, CREB Total, DR-5, EGF, ENA-78, Eotaxin, Fatty Acid Binding Protein, FGF-basic, granulocyte colony-stimulating factor (G-CSF), GCP-2, Granulocyte-macrophage Colony-stimulating Factor GM-CSF (GM-CSF), growth-related oncogene-keratinocytes (GRO-KC), HGF, ICAM-1, IFN-alpha, IFN-gamma, the interleukins IL-10, IL-11, IL-12, IL-12 p40, IL-12 p40/p70, IL-12 p70, IL-13, IL-15, IL-16, IL-17, IL-18, IL-1alpha, IL-1beta, IL-1ra, IL-1ra/IL-1F3, IL-2, IL-3, IL-4, IL-5, IL-6, IL-7, IL-8, IL-9, interferon-inducible protein (10 IP-10), JE/MCP-1, keratinocytes (KC), KC/GROa, LIF, Lymphotactin, M-CSF, monocyte chemoattractant protein-1 (MCP-1), MCP-1(MCAF), MCP-3, MCP-5, MDC, MIG, macrophage inflammatory (MIP-1 alpha), MT-1 beta, MIP-1 gamma, MIP-2, MIP-3 beta, OSM, PDGF-BB, regulated upon activation, normal T cell expressed and secreted (RANTES), Rb (pT821), Rb (total), Rb pSpT249/ 252, Tau (pS214), Tau (pS396), Tau (total), Tissue Factor, tumor necrosis factor-alpha (TNF-alpha), TNF-beta, TNF-RI, TNF-RII, VCAM-1, and VEGF. In some embodiments, the cytokine is IL-12p70, IL-10, IL-1 alpha, IL-3, IL-12 p40, IL-1ra, IL-12, IL-6, IL-4, IL-18, IL-10, IL-5, eotaxin, IL-16, MIG, IL-8, IL-17, IL-7, IL-15, IL-13, IL-2R (soluble), IL-2, LIF/HILDA, IL-1 beta, Fas/CD95/Apo-1, and MCP-1.

Growth Factors

Growth factors that can be used in methods and compositions of the invention include EGF Ligands such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, LRIG1; EGF R/ErbB Receptor Family such as EGF R, ErbB3, ErbB2, ErbB4; FGF Family such as FGF LigandsFGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-22, FGF-10, FGF-23, FGF-11, KGF/FGF-7, FGF Receptors FGF R1-4, FGF R3, FGF R1, FGF R4, FGF R2, FGF R5, FGF Regulators FGF-BP; the Hedgehog Family Desert Hedgehog, Sonic Hedgehog, Indian Hedgehog; Hedgehog Related Molecules & Regulators BOC, GLI-3, CDO, GSK-3 alpha/beta, DISP1, GSK-3 alpha, Gas1, GSK-3 beta, GLI-1, Hip, GLI-2; the IGF FamilyIGF LigandsIGF-I, IGF-II, IGF-I Receptor (CD221) IGF-I R, and IGF Binding Protein (IGFBP) Family ALS, IGFBP-5, CTGF/CCN2, IGFBP-6, Cyr61/CCN1, IGFBP-L1, Endocan, IGFBP-rp1/IGFBP-7, IGFBP-1, IGFBP-rP10, IGFBP-2, NOV/CCN3, IGFBP-3, WISP-1/CCN4, IGFBP-4; Receptor Tyrosine Kinases Axl, FGF R4, C1q R1/CD93, FGF R5, DDR1, Flt-3, DDR2, HGF R, Dtk, IGF-I R, EGF, R IGF-II R, Eph, INSRR, EphA1, Insulin R/CD220, EphA2, M-CSF R, EphA3, Mer, EphA4, MSP R/Ron, EphA5, MuSK, EphA6, PDGF R alpha, EphA7, PDGF R beta, EphA8, Ret, BphB1, RTK-like Orphan Receptor 1/ROR1, EphB2, RTK-like Orphan Receptor 2/ROR2, EphB3, SCF R/c-kit, EphB4, Tie-1, EphB6, Tie-2, ErbB2, TrkA, ErbB3, TrkB, ErbB4, TrkC, FGF, R1-4 VEGF R, FGF R1, VEGF R1/Flt-1, FGF R2, VEGF R2/KDR/Flk-1, FGF R3, VEGF R3/Flt-4; Proteoglycans & Regulators Proteoglycans Aggrecan, Mimecan, Agrin, NG2/MCSP, Biglycan, Osteoadherin, Decorin, Podocan, DSPG3, delta-Sarcoglycan, Endocan, Syndecan-1/CD138, Endoglycan, Syndecan-2, Endorepellin/Perlecan, Syndecan-3, Glypican 2, Syndecan-4, Glypican 3, Testican 1/SPOCK1, Glypican 5, Testican 2/SPOCK2, Glypican 6, Testican 3/SPOCK3, Lumican, Versican, Proteoglycan Regulators, Arylsulfatase A/ARSA, Glucosamine (N-acetyl)-6-Sulfatase/GNS, Exostosin-like 2/EXTL2, HS6ST2, Exostosin-like 3/EXTL3, Iduronate 2-Sulfatase/IDS, GalNAc4S-6ST; SCF, Flt-3 Ligand & M-CSF Flt-3, M-CSF R, Flt-3 Ligand, SCF, M-CSF, SCF R/c-kit; TGF-beta Superfamily (same as listed for inflammatory markers); VEGF/PDGF Family Neuropilin-1, P1GF, Neuropilin-2, P1GF-2, PDGF, VEGF, PDGF R alpha, VEGF-B, PDGF R beta, VEGF-C, PDGF-A, VEGF-D, PDGF-AB, VEGF R, PDGF-B, VEGF R1/Flt-1, PDGF-C, VEGF R2/KDR/Flk-1, PDGF-D, VEGF R3/Flt-4; Wnt-related Molecules Dickkopf Proteins & Wnt InhibitorsDkk-1, Dkk-4, Dkk-2, Soggy-1, Dkk-3, WIF-1 Frizzled & Related Proteins Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP Wnt Ligands Wnt-1, Wnt-8a, Wnt-2b, Wnt-8b, Wnt-3a, Wnt-9a, Wnt-4, Wnt-9b, Wnt-5a, Wnt-10a, Wnt-5b, Wnt-10b, Wnt-7a, Wnt-11, Wnt-7b; Other Wnt-related Molecules APC, Kremen-2, Axin-1, LRP-1, beta-Catenin, LRP-6, Dishevelled-1, Norrin, Dishevelled-3, PKC beta 1, Glypican 3, Pygopus-1, Glypican 5, Pygopus-2, GSK-3 alpha/beta, R-Spondin 1, GSK-3 alpha, R-Spondin 2, GSK-3 beta, R-Spondin 3, ICAT, RTK-like Orphan Receptor 1/ROR1, Kremen-1, RTK-like Orphan Receptor 2/ROR, and Other Growth Factors CTGF/CCN2, beta-NGF, Cyr61/CCN1, Norrin, DANCE, NOV/CCN3, EG-VEGF/PK1, Osteocrin, Hepassocin, PD-ECGF, HGF, Progranulin, LECT2, Thrombopoietin, LEDGF, and WISP-1/CCN4.

Markers of Inflammation

Markers of inflammation that can be used in methods and compositions of the invention include ICAM-1, RANTES, MIP-2, MIP-1-beta, MT-1-alpha, and MMP-3. Further markers of inflammation include adhesion molecules such as the integrins α1β1, α2β1, α3β1, α4β1, α5β1, α6β1, α7β1, α8β1, α9β1, αVβ1, α4β7, α6β4, αDβ2, αLβ2, αMβ2, αVβ3, αVβ5, αVβ6, αVβ8, αXβ2, αIIbβ3, αIELbβ7, beta-2 integrin, beta-3 integrin, beta-2 integrin, beta-4 integrin, beta-5 integrin, beta-6 integrin, beta-7 integrin, beta-8 integrin, alpha-1 integrin, alpha-2 integrin, alpha-3 integrin, alpha-4 integrin, alpha-5 integrin, alpha-6 integrin, alpha-7 integrin, alpha-8 integrin, alpha-9 integrin, alpha-D integrin, alpha-L integrin, alpha-M integrin, alpha-V integrin, alpha-X integrin, alpha-IIb integrin, alphaIELb integrin; Integrin-associated Molecules such as Beta IG-H3, Melusin, CD47, MEPE, CD151, Osteopontin, IBSP/Sialoprotein II, RAGE, IGSF8; Selectins such as E-Selectin, P-Selectin, L-Selectin; and Ligands such as CD34, GlyCAM-1, MadCAM-1, PSGL-1, vitronectic, vitronectin receptor, fibronectin, vitronectin, collagen, laminin, ICAM-1, ICAM-3, BL-CAM, LFA-2, VCAM-1, NCAM, and PECAM. Further markers of inflammation include cytokines such as IFN-α, IFN-β, IFN-ε, -κ, -τ, and -ζ, IFN-ω, IFN-γ, IL29, IL28A and IL28B, IL-1, IL-1α and β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, and TCCR/WSX-1. Further markets of inflammation include cytokine receptors such as Common beta chain, IL-3 R alpha, IL-3 R beta, GM-CSF R, IL-5 R alpha, Common gamma Chain/IL-2 R gamma, IL-2 R alpha, IL-9 R, IL-2 R beta, IL-4 R, IL-21 R, IL-15 R alpha, IL-7 R alpha/CD127, IL-1ra/IL-1F3, IL-1 R8, IL-1 RI, IL-1 R9, IL-1 RII, IL-18 R alpha/IL-1 R5, IL-1 R3/IL-1 RAcP, IL-18 R beta/IL-1 R7, IL-1 R4/ST2 SIGIRR, IL-1 R6/IL-1 R rp2, IL-11 R alpha, IL-31 RA, CNTF R alpha, Leptin R, G-CSF R, LIF R alpha, IL-6 R, OSM R beta, IFN-alpha/beta R1, IFN-alpha/beta R2, IFN-gamma R1, IFN-gamma R2, IL-10 R alpha, IL-10 R beta, IL-20 R alpha, IL-20 R beta, IL-22 R, IL-17 R, IL-17 RD, IL-17 RC, IL-17B R, IL-13 R alpha 2, IL-23 R, IL-12 R beta 1, IL-12 R beta 2, TCCR/WSX-1, and IL-13 R alpha 1. Further markers of inflammation include chemokines such as CCL-1, CCL-2, CCL-3, CCL-4, CCL-5, CCL-6, CCL-7, CCL-8, CCL-9, CCL-10, CCL-11, CCL-12, CCL-13, CCL-14, CCL-15, CCL-16, CCL-17, CCL-18, CCL-19, CCL-20, CCL-21, CCL-22, CCL-23, CCL-24, CCL-25, CCL-26, CCL-27, CCL-28, MCK-2, MIP-2, CINC-1, CINC-2, KC, CINC-3, LIX, GRO, Thymus Chemokine-1, CXCL-1, CXCL-2, CXCL-3, CXCL-4, CXCL-5, CXCL-6, CXCL-7, CXCL-8, CXCL-9, CXCL-10, CXCL-11, CXCL-12, CXCL-13, CXCL-14, CXCL-15, CXCL-16, CXCL-17, XCL1, XCL2, and Chemerin. Further markers of inflammation include chemokine receptors such as CCR-1, CCR-2, CCR-3, CCR-4, CCR-5, CCR-6, CCR-7, CCR-8, CCR-9, CCR-10, CXCR3, CXCR6, CXCR4, CXCR1, CXCR5, CXCR2, Chem R23. Further markers of inflammation include Tumor necrosis factors (TNFs), such as TNF.alpha., 4-1BB Ligand/TNFSF9, LIGHT/TNFSF14, APRIL/TNFSF13, Lymphotoxin, BAFF/TNFSF13B, Lymphotoxin beta/TNFSF3, CD27 Ligand/TNFSF7, OX40 Ligand/TNFSF4, CD30 Ligand/TNFSF8, TL1A/TNFSF15, CD40 Ligand/TNFSF5, TNF-alpha/TNFSF1A, EDA, TNF-beta/TNFSF1B, EDA-A2, TRAIL/TNFSF10, Fas Ligand/TNFSF6, TRANCE/TNFSF11, GITR Ligand/TNFSF18, and TWEAK/TNFSF12. Further markers of inflammation include TNF Superfamily Receptors such as 4-1BB/TNFRSF9, NGF R/TNFRSF16, BAFF R/TNFRSF13C, Osteoprotegerin/TNFRSF11B, BCMA/TNFRSF17, OX40/TNFRSF4, CD27/TNFRSF7, RANK/TNFRSF11A, CD30/TNFRSF8, RELT/TNFRSF19L, CD40/TNFRSF5, TACI/TNFRSF13B, DcR3/TNFRSF6B, TNF RI/TNFRSF1A, DcTRAIL R1/TNFRSF23, TNF RII/TNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF10D, Fas/TNFRSF6, TROY/TNFRSF19, GITR/TNFRSF18, TWEAK R/TNFRSF12, HVEM/TNFRSF14, and XEDAR. Further markers of inflammation include TNF Superfamily Regulators such as FADD, TRAF-2, RIP1, TRAF-3, TRADD, TRAF-4, TRAP-1, and TRAF-6. Further markers of inflammation include acute-phase reactants and acute phase proteins. Further markers of inflammation include TGF-beta superfamily ligands such as Activins, Activin A, Activin B, Activin AB, Activin C, BMPs (Bone Morphogenetic Proteins), BMP-2, BMP-7, BMP-3, BMP-8, BMP-3b/GDF-10, BMP-9, BMP-4, BMP-10, BMP-5, BMP-15/GDF-9B, BMP-6, Decapentaplegic, Growth/Differentiation Factors (GDFs), GDF-1, GDF-8, GDF-3, GDF-9 GDF-5, GDF-11, GDF-6, GDF-15, GDF-7, GDNF Family Ligands, Artemin, Neurturin, GDNF, Persephin, TGF-beta, TGF-beta, TGF-beta 3, TGF-beta 1, TGF-beta 5, LAP (TGF-beta 1), Latent TGF-beta bp1, Latent TGF-beta 1, Latent TGF-beta bp2, TGF-beta 1.2, Latent TGF-beta bp4, TGF-beta 2, Lefty, MIS/AMH, Lefty-1, Nodal, Lefty-A, Activin RIA/ALK-2, GFR alpha-1/GDNF R alpha-1, Activin RIB/ALK-4, GFR alpha-2/GDNF R alpha-2, Activin RIIA, GFR alpha-3/GDNF R alpha-3, Activin RIIB, GFR alpha-4/GDNF R alpha-4, ALK-1, MIS MI, ALK-7, Ret, BMPR-IA/ALK-3, TGF-beta RI/ALK-5, BMPR-IB/ALK-6, TGF-beta RII, BMPR-II, TGF-beta RIIb, Endoglin/CD105, and TGF-beta RIII. Further markers of inflammation include TGF-beta superfamily Modulators such as Amnionless, NCAM-1/CD56, BAMBI/NMA, Noggin, BMP-1/PCP, NOMO, Caronte, PRDC, Cerberus 1, SKI, Chordin, Smad1, Chordin-Like 1, Smad2, Chordin-Like 2, Smad3, COCO, Smad4, CRIM1, Smad5, Cripto, Smad7, Crossveinless-2, Smad8, Cryptic, SOST, DAN, Latent TGF-beta bp1, Decorin, Latent TGF-beta bp2, FLRG, Latent TGF-beta bp4, Follistatin, TMEFF1/Tomoregulin-1, Follistatin-like 1, TMEFF2, GASP-1/WFIKKNRP, TSG, GASP-2/WFIKKN, TSK, Gremlin, and Vasorin. Further markers of inflammation include EGF Ligands such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, and LRIG1. Further markers of inflammation include EGF R/ErbB Receptor Family, such as EGF R, ErbB3, ErbB2, and ErbB4. Further markers of inflammation include Fibrinogen. Further markers of inflammation include SAA. Further markers of inflammation include glial markers, such as alpha.1-antitrypsin, C-reactive protein (CRP), .alpha.2-macroglobulin, glial fibrillary acidic protein (GFAP), Mac-1, and F4/80. Further markers of inflammation include myeloperoxidase. Further markers of inflammation include Complement markers such as C3d, C1q, C5, C4d, C4 bp, and C5a-C9. Further markers of inflammation include Major histocompatibility complex (MHC) glycoproteins, such as HLA-DR and HLA-A,D,C. Further markers of inflammation include Microglial markers, such as CR3 receptor, MHC I, MHC II, CD 31, CD11a, CD11b, CD11c, CD68, CD45RO, CD45RD, CD18, CD59, CR4, CD45, CD64, and CD44. Further markers of inflammation include alpha.2 macroglobulin receptor, Fibroblast growth factor, Fc gamma RI, Fc gamma RII, CD8, LCA (CD45), CD18 ( ) CD59, Apo J, clusterin, type 2 plasminogen activator inhibitor, CD44, Macrophage colony stimulating factor receptor, MRP14, 27E10, 4-hydroxynonenal-protein conjugates, I.kappa.B, NF.kappa.B, cPLA.sub.2, COX-2, Matrix metalloproteinases, Membrane lipid peroxidation, and ATPase activity. HSPC228, EMP1, CDC42, TLE3, SPRY2, p40BBP, HSPC060 and NAB2, or a down-regulation of HSPA1A, HSPA1B, MAPRE2 and OAS1 expression, TACE/ADAM17, alpha-1-Acid Glycoprotein, Angiopoietin-1, MIF, Angiopoietin-2, CD14, beta-Defensin 2, MMP-2, ECF-L/CHI3L3, MMP-7, EGF, MMP-9, EMAP-II, MSP, EN-RAGE, Nitric Oxide, Endothelin-1, Osteoactivin/GPNMB, FPR1, PDGF, FPRL1, Pentraxin 3/TSG-14, FPRL2, Gas6, PLUNC, GM-CSF, RAGE, S100A10, S100A8, S100A9, HIF-1 alpha, Substance P, TFPI, TGF-beta 1, TIMP-1, TIMP-2, TIMP-3, TIMP-4, TLR4, LBP, TREM-1, Leukotriene A4, Hydrolase TSG-6, Lipocalin-1, uPA, M-CSF, and VEGF.

Miscellaneous Markers

Oncology markers that can be used in methods and compositions of the invention include EGF, TNF-alpha, PSA, VEGF, TGF-beta1, FGFb, TRAIL, and TNF-RI (p55).

Markers of endocrine function that can be used in methods and compositions of the invention include 17 beta-estradiol (E2), DHEA, ACTH, gastrin, and growth hormone (hGH).

Markers of autoimmunity that can be used in methods and compositions of the invention include GM-CSF, C-Reactive Protein, and G-CSF.

Markers of thyroid function that can be used in methods and compositions of the invention include cyclicAMP, calcitonin, and parathyroid hormone.

Cardiovascular markers that can be used in methods and compositions of the invention include cardiac troponin I, cardiac troponin T, B-natriuretic peptide, NT-proBNP, C-ractive Protein HS, and beta-thromboglobulin.

Markers of diabetes that can be used in methods and compositions of the invention include C-peptide and leptin.

Markers of infectious disease that can be used in methods and compositions of the invention include IFN-gamma and IFN-alpha.

Markers of metabolism that can be used in methods and compositions of the invention include Bio-intact PTH (1-84) and PTH.

Markers of Biological States

Markers can indicate the presence of a particular phenotypic state of interest. Examples of phenotypic states include, phenotypes resulting from an altered environment, drug treatment, genetic manipulations or mutations, injury, change in diet, aging, or any other characteristic(s) of a single organism or a class or subclass of organisms.

In some embodiments, a phenotypic state of interest is a clinically diagnosed disease state. Such disease states include, for example, cancer, cardiovascular disease, inflammatory disease, autoimmune disease, neurological disease, infectious disease and pregnancy related disorders. Alternatively, states of health can be detected using markers.

Cancer phenotypes are included in some aspects of the invention. Examples of cancer herein include, but are not limited to: breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, non-small cell lung carcinoma gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Cardiovascular disease can be included in other applications of the invention. Examples of cardiovascular disease include, but are not limited to, congestive heart failure, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, myocardial ischemia, myocardial infarction, cardiac tamponade, myocarditis, pericarditis, arrhythmogenic right ventricular dysplasia, hypertrophic cardiomyopathy, Williams syndrome, heart valve diseases, endocarditis, bacterial disease, pulmonary atresia, aortic valve stenosis, Raynaud's disease, cholesterol embolism, Wallenberg syndrome, Hippel-Lindau disease, and telangiectasis.

Inflammatory disease and autoimmune disease can be included in other embodiments of the invention. Examples of inflammatory disease and autoimmune disease include, but are not limited to, rheumatoid arthritis, non-specific arthritis, inflammatory disease of the larynx, inflammatory bowel disorder, psoriasis, hypothyroidism (e.g., Hashimoto thyroidism), colitis, Type 1 diabetes, pelvic inflammatory disease, inflammatory disease of the central nervous system, temporal arteritis, polymyalgia rheumatica, ankylosing spondylitis, polyarteritis nodosa, Reiter's syndrome, scleroderma, systemis lupus and erythematosus.

The methods and compositions of the invention can also provide laboratory information about markers of infectious disease including markers of Adenovirus, Bordella pertussis, Chlamydia pneumoiea, Chlamydia trachomatis, Cholera Toxin, Cholera Toxin β, Campylobacter jejuni, Cytomegalovirus, Diptheria Toxin, Epstein-Barr NA, Epstein-Barr EA, Epstein-Barr VCA, Helicobacter Pylori, Hepatitis B virus (HBV) Core, Hepatitis B virus (HBV) Envelope, Hepatitis B virus (HBV) Surface (Ay), Hepatitis C virus (HCV) Core, Hepatitis C virus (HCV) NS3, Hepatitis C virus (HCV) NS4, Hepatitis C virus (HCV) NS5, Hepatitis A, Hepatitis D, Hepatitis E virus (HEV) orf2 3KD, Hepatitis E virus (HEV) orf2 6KD, Hepatitis E virus (HEV) orf3 3KD, Human immunodeficiency virus (HIV)-1 p24, Human immunodeficiency virus (HIV)-1 gp41, Human immunodeficiency virus (HIV)-1 gp120, Human papilloma virus (HPV), Herpes simplex virus HSV-1/2, Herpes simplex virus HSV-1 gD, Herpes simplex virus HSV-2 gG, Human T-cell leukemia virus (HTLV)-1/2, Influenza A, Influenza A H3N2, Influenza B, *Leishmania donovani*, Lyme disease, Mumps, *M. pneumoniae, M. tuberculosis*, Parainfluenza 1, Parainfluenza 2, Parainfluenza 3, Polio Virus, Respiratory syncytial virus (RSV), Rubella, Rubeola, Streptolysin O, Tetanus Toxin, *T. pallidum* 15kd, *T. pallidum* p47, *T. cruzi*, Toxoplasma, and Varicella Zoster.

IV. Labels

In some embodiments, the invention provides methods and compositions that include labels for the highly sensitive detection and quantitation of molecules, e.g., of markers.

One skilled in the art will recognize that many strategies can be used for labeling target molecules to enable their detection or discrimination in a mixture of particles. The labels can be attached by any known means, including methods that utilize non-specific or specific interactions of label and target. Labels can provide a detectable signal or affect the mobility of the particle in an electric field. Labeling can be accomplished directly or through binding partners.

In some embodiments, the label comprises a binding partner to the molecule of interest, where the binding partner is attached to a fluorescent moiety. The compositions and methods of the invention can use highly fluorescent moieties. Moieties suitable for the compositions and methods of the invention are described in more detail below.

In some embodiments, the invention provides a label for detecting a biological molecule comprising a binding partner for the biological molecule that is attached to a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the moiety comprises a plurality of fluorescent entities, e.g., about 2 to 4, 2 to 5, 2 to 6, 2 to 7, 2 to 8, 2 to 9, 2 to 10, or about 3 to 5, 3 to 6, 3 to 7, 3 to 8, 3 to 9, or 3 to 10 fluorescent entities. In some embodiments, the moiety comprises about 2 to 4 fluorescent entities. In some embodiments, the biological molecule is a protein or a small molecule. In some embodiments, the biological molecule is a protein. The fluorescent entities can be fluorescent dye molecules. In some embodiments, the fluorescent dye molecules comprise at least one substituted indolium ring system in which the substituent on the 3-carbon of the indolium ring contains a chemically reactive group or a conjugated substance. In some embodiments, the dye molecules are Alexa Fluor molecules selected from the group consisting of Alexa Fluor 488, Alexa Fluor 532, Alexa Fluor 647, Alexa Fluor 680 or Alexa Fluor 700. In some embodiments, the dye molecules are Alexa Fluor molecules selected from the group consisting of Alexa Fluor 488, Alexa Fluor 532, Alexa Fluor 680 or Alexa Fluor 700. In some embodiments, the dye molecules are Alexa Fluor 647 dye molecules. In some embodiments, the dye molecules comprise a first type and a second type of dye molecules, e.g., two different Alexa Fluor molecules, e.g., where the first type and second type of dye molecules have different emission spectra. The ratio of the number of first type to second type of dye molecule can be, e.g., 4 to 1, 3 to 1, 2 to 1, 1 to 1, 1 to 2, 1 to 3 or 1 to 4. The binding partner can be, e.g., an antibody.

In some embodiments, the invention provides a label for the detection of a marker, wherein the label comprises a binding partner for the marker and a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the fluorescent moiety comprises a fluorescent molecule. In some embodiments, the fluorescent moiety comprises a plurality of fluorescent molecules, e.g., about 2 to 10, 2 to 8, 2 to 6, 2 to 4, 3 to 10, 3 to 8, or 3 to 6 fluorescent molecules. In some embodiments, the label comprises about 2 to 4 fluorescent molecules. In some embodiments, the fluorescent dye molecules comprise at least one substituted indolium ring system in which the substituent on the 3-carbon of the indolium ring contains a chemically reactive group or a conjugated substance. In some embodiments, the fluorescent molecules are selected from the group consisting of Alexa Fluor 488, Alexa Fluor 532, Alexa Fluor 647, Alexa Fluor 680 or Alexa Fluor 700. In some embodiments, the fluorescent molecules are selected from the group consisting of Alexa Fluor 488, Alexa Fluor 532, Alexa Fluor 680 or Alexa Fluor 700. In some embodiments, the fluorescent molecules are Alexa Fluor 647 molecules. In some embodiments, the binding partner comprises an antibody. In some embodiments, the antibody is a monoclonal antibody. In other embodiments, the antibody is a polyclonal antibody.

The antibody can be specific to any suitable marker. In some embodiments, the antibody is specific to a marker that is selected from the group consisting of cytokines, growth factors, oncology markers, markers of inflammation, endocrine markers, autoimmune markers, thyroid markers, cardiovascular markers, markers of diabetes, markers of infectious disease, neurological markers, respiratory markers, gastrointestinal markers, musculoskeletal markers, dermatological disorders, and metabolic markers.

In some embodiments, the antibody is specific to a marker that is a cytokine. In some embodiments, the cytokine is selected from the group consisting of BDNF, CREB pS133, CREB Total, DR-5, EGF, ENA-78, Eotaxin, Fatty Acid Binding Protein, FGF-basic, granulocyte colony-stimulating factor (G-CSF), GCP-2, Granulocyte-macrophage Colony-stimulating Factor GM-CSF (GM-CSF), growth-related oncogene-keratinocytes (GRO-KC), HGF, ICAM-1, IFN-alpha, UN-gamma, the interleukins IL-10, IL-11, IL-12, IL-12 p40, IL-12 p40/p70, IL-12 p70, IL-13, IL-15, IL-16, IL-17, IL-18, IL-1alpha, IL-1beta, IL-1ra, IL-1ra/IL-1F3, IL-2, IL-3, IL-4, IL-5, IL-6, IL-7, IL-8, IL-9, interferon-inducible protein (10 IP-10), JE/MCP-1, keratinocytes (KC), KC/GROa, LIF, Lymphotacin, M-CSF, monocyte chemoattractant protein-1 (MCP-1), MCP-1(MCAF), MCP-3, MCP-5, MDC, MIG, macrophage inflammatory (MT-1 alpha), MT-1 beta, MIP-1 gamma, MIP-2, MIP-3 beta, OSM, PDGF-BB, regulated upon activation-normal T cell-expressed and secreted (RANTES), Rb (pT821), Rb (total), Rb pSpT249/ 252, Tau (pS214), Tau (pS396), Tau (total), Tissue Factor, tumor necrosis factor-alpha (TNF-alpha), TNF-beta, TNF-RI, TNF-RII, VCAM-1, and VEGF.

In some embodiments, the cytokine is selected from the group consisting of IL-12 p70, IL-10, IL-1 alpha, IL-3, IL-12 p40, IL-1ra, IL-12, IL-6, IL-4, IL-18, IL-10, IL-5, Eotaxin, IL-16, MIG, IL-8, IL-17, IL-7, IL-15, IL-13, IL-2R (soluble), IL-2, LIF/HILDA, IL-1 beta, Fas/CD95/Apo-1 and MCP-1.

In some embodiments, the antibody is specific to a marker that is a growth factor (GF). In some embodiments, the antibody is specific to a marker that is a growth factor that is TGF-beta. In some embodiments, the growth factor is a GF ligand such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, LRIG1; EGF R/ErbB Receptor Family such as EGF R, ErbB3, ErbB2, ErbB4; FGF Family such as FGF Ligands, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-22, FGF-10, FGF-23, FGF-11, KGF/ FGF-7, FGF Receptors FGF R1-4, FGF R3, FGF R1, FGF R4, FGF R2, FGF R5, FGF Regulators FGF-BP; the Hedgehog Family Desert Hedgehog, Sonic Hedgehog, Indian Hedgehog; Hedgehog Related Molecules & Regulators BOC, GLI-3, CDO, GSK-3 alpha/beta, DISP1, GSK-3 alpha, Gas1, GSK-3 beta, GLI-1, Hip, GLI-2; the IGF Family IGF ligands IGF-I, IGF-II, IGF-I Receptor (CD221) IGF-I R, and IGF Binding Protein (IGFBP) Family ALS, IGFBP-5, CTGF/ CCN2, IGFBP-6, Cyr61/CCN1, IGFBP-L1, Endocan, IGFBP-rp1/IGFBP-7, IGFBP-1, IGFBP-rP10, IGFBP-2, NOV/CCN3, IGFBP-3, WISP-1/CCN4, IGFBP-4; Receptor Tyrosine Kinases Axl, FGF R4, C1q R1/CD93, FGF R5, DDR1, Flt-3, DDR2, HGF R, Dtk; IGF-I R, EGF, R IGF-II R, Eph, INSRR, EphA1, Insulin R/CD220, EphA2, M-CSF R, EphA3, Mer, EphA4, MSP R/Ron, EphA5, MuSK, EphA6, PDGF R alpha, EphA7, PDGF R beta, EphA8, Ret, EphB1, RTK-like Orphan Receptor 1/ROR1, EphB2, RTK-like Orphan Receptor 2/ROR2, EphB3, SCF R/c-kit, EphB4, Tie-1, EphB6, Tie-2, ErbB2, TrkA, ErbB3, TrkB, ErbB4, TrkC, FGF, R1-4 VEGF R, FGF R1, VEGF R1/Flt-1, FGF R2, VEGF R2/KDR/Flk-1, FGF R3, VEGF R3/Flt-4; Proteoglycans & Regulators Proteoglycans Aggrecan, Mimecan, Agrin, NG2/MCSP, Biglycan, Osteoadherin, Decorin, Podocan, DSPG3, delta-Sarcoglycan, Endocan, Syndecan-1/ CD138, Endoglycan, Syndecan-2, Endorepellin/Perlecan, Syndecan-3, Glypican 2, Syndecan-4, Glypican 3, Testican 1/SPOCK1, Glypican 5, Testican 2/SPOCK2, Glypican 6, Testican 3/SPOCK3, Lumican, Versican, Proteoglycan. Regulators, Arylsulfatase A/ARSA, Glucosamine (N-acetyl)-6-Sulfatase/GNS, Exostosin-like 2/EXTL2, HS6ST2, Exostosin-like 3/EXTL3, Iduronate 2-Sulfatase/ IDS, GalNAc4S-6ST; SCF, Flt-3 Ligand & M-CSF Flt-3, M-CSF R, Flt-3 Ligand, SCF, M-CSF, SCF R/c-kit; TGF-beta Superfamily (same as listed for inflammatory markers); VEGF/PDGF Family Neuropilin-1, P1GF, Neuropilin-2, P1GF-2, PDGF, VEGF, PDGF R alpha, VEGF-B, PDGF R beta, VEGF-C, PDGF-A, VEGF-D, PDGF-AB, VEGF R, PDGF-B, VEGF R1/Flt-1, PDGF-C, VEGF R2/KDR/Flk-1, PDGF-D, VEGF R3/Flt-4; Wnt-related Molecules Dickkopf Proteins & Wnt Inhibitors Dick-1, Dkk-4, Dkk-2, Soggy-1, Dkk-3, WIF-1 Frizzled & Related Proteins Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP Wnt Ligands Wnt-1, Wnt-8a, Wnt-2b, Wnt-8b, Wnt-3a, Wnt-9a, Wnt-4, Wnt-9b, Wnt-5a, Wnt-10a, Wnt-5b, Wnt-10b, Wnt-7a, Wnt-11, Wnt-7b; Other Wnt-related Molecules APC, Kremen-2, Axin-1, LRP-1, beta-Catenin, LRP-6, Dishevelled-1, Norrin, Dishevelled-3, PKC beta 1, Glypican 3, Pygopus-1, Glypican 5, Pygopus-2, GSK-3 alpha/beta, R-Spondin 1, GSK-3 alpha, R-Spondin 2, GSK-3 beta, R-Spondin 3, ICAT, RTK-like Orphan Receptor 1/ROR1, Kremen-1, RTK-like Orphan Receptor 2/ROR, and Other Growth Factors CTGF/CCN2, beta-NGF, Cyr61/CCN1, Norrin, DANCE, NOV/CCN3, EG-VEGF/PK1, Osteocrin, Hepassocin, PD-ECGF, HGF, Progranulin, LECT2, Thrombopoietin, LEDGF, or WISP-1/CCN4.

In some embodiments, the antibody is specific to a marker that is a marker for cancer (oncology marker). In some embodiments, the antibody is specific to a marker that is a marker for cancer that is EGF. In some embodiments, the antibody is specific to a marker that is a marker for cancer that is TNF-alpha. In some embodiments, the antibody is specific to a marker that is a marker for cancer that is PSA. In some embodiments, the antibody is specific to a marker that is a marker for cancer that is VEGF. In some embodiments, the antibody is specific to a marker that is a marker for cancer that is TGF-beta. In some embodiments, the antibody is specific to a marker that is a marker for cancer that is FGFb. In some embodiments, the antibody is specific to a marker that is a marker for cancer that is TRAIL. In some embodiments, the antibody is specific to a marker that is a marker for cancer that is TNF-RI (p55).

In further embodiments, the antibody is specific to a marker for cancer that is alpha-Fetoprotein. In some embodiments, the antibody is specific to a marker for cancer that is ER beta/NR3A2. In some embodiments, the antibody is specific to a marker for cancer that is ErbB2. In some embodiments, the antibody is specific to a marker for cancer that is Kallikrein 3/PSA. In some embodiments, the antibody is specific to a marker for cancer that is ER alpha/NR3A1. In some embodiments, the antibody is specific to a marker for cancer that is Progesterone R/NR3C3. In some embodiments, the antibody is specific to a marker for cancer that is A33. In some embodiments, the antibody is specific to a marker for cancer that is MIA. In some embodiments, the antibody is specific to a marker for cancer that is Aurora A. In some embodiments, the antibody is specific to a marker for cancer that is MMP-2. In some embodiments, the antibody is specific to a marker for cancer that is Bcl-2. In some embodiments, the antibody is specific to a marker for cancer that is MMP-3. In some embodiments, the antibody is specific to a marker for cancer that is Cadherin-13. In some embodiments, the antibody is specific to a marker for cancer that is MMP-9. In some embodiments, the antibody is specific to a marker for cancer that is E-Cadherin. In some embodiments, the antibody is specific to a marker for cancer that is NEK2. In some embodiments, the antibody is specific to a marker for cancer that is Carbonic Anhydrase IX. In some embodiments, the antibody is specific to a marker for cancer that is Nestin. In some embodiments, the antibody is specific to a marker for cancer that is beta-Catenin. In some embodiments, the antibody is specific to a marker for cancer that is NG2/MCSP. In some embodiments, the antibody is specific to a marker for cancer that is Cathepsin D. In some embodiments, the antibody is specific to a marker for cancer that is Osteopontin. In some embodiments, the antibody is specific to a marker for cancer that is CD44. In some embodiments, the antibody is specific to a marker for cancer that is p21/CIP1/CDKN1A. In some embodiments, the antibody is specific to a marker for cancer that is CEACAM-6. In some embodiments, the antibody is specific to a marker for cancer that is p27/Kip1. In some embodiments, the antibody is specific to a marker for cancer that is Cornulin. In some embodiments, the antibody is specific to a marker for cancer that is p53. In some embodiments, the antibody is specific to a marker for cancer that is DPPA4. In some embodiments, the antibody is specific to a marker for cancer that is Prolactin. In some embodiments, the antibody is specific to a marker for cancer that is ECM-1. In some embodiments, the antibody is specific to a marker for cancer that is PSP94. In some embodiments, the antibody is specific to a marker for cancer that is EGF. In some embodiments, the antibody is specific to a marker for cancer that is S100B. In some embodiments, the antibody is specific to a marker for cancer that is EGF R. In some embodiments, the antibody is specific to a marker for cancer that is S100P. In some embodiments, the antibody is specific to a marker for cancer that is EMMPRIN/CD147. In some embodiments, the antibody is specific to a marker for cancer that is SCF R/c-kit. In some embodiments, the antibody is specific to a marker for cancer that is Fibroblast Activation Protein alpha/FAP. In some embodiments, the antibody is specific to a marker for cancer that is Serpin E1/PAI-1. In some embodiments, the antibody is specific to a marker for cancer that is FGF acidic. In some embodiments, the antibody is specific to a marker for cancer that is Serum Amyloid A4. In some embodiments, the antibody is specific to a marker for cancer that is FGF basic. In some embodiments, the antibody is specific to a marker for cancer that is Survivin. In some embodiments, the antibody is specific to a marker for cancer that is Galectin-3. In some embodiments, the antibody is specific to a marker for cancer that is TEM8. In some embodiments, the antibody is specific to a marker for cancer that is Glypican 3. In some embodiments, the antibody is specific to a marker for cancer that is TIMP-1. In some embodiments, the antibody is specific to a marker for cancer that is HIN-1/Secretoglobulin 3A1. In some embodiments, the antibody is specific to a marker for cancer that is TIMP-2. In some embodiments, the antibody is specific to a marker for cancer that is IGF-I. In some embodiments, the antibody is specific to a marker for cancer that is TIMP-3. In some embodiments, the antibody is specific to a marker for cancer that is IGFBP-3. In some embodiments, the antibody is specific to a marker for cancer that is TIMP-4. In some embodiments, the antibody is specific to a marker for cancer that is IL-6. In some embodiments, the antibody is specific to a marker for cancer that is TNF-alpha/TNFSF1A. In some embodiments, the antibody is specific to a marker for cancer that is Kallikrein 6/Neurosin. In some embodiments, the antibody is specific to a marker for cancer that is TRAF-4. In some embodiments, the antibody is specific to a marker for cancer that is M-CSF. In some embodiments, the antibody is specific to a marker for cancer that is uPA. In some embodiments, the antibody is specific to a marker for cancer that is Matriptase/ST14. In some embodiments, the antibody is specific to a marker for cancer that is uPAR. In some embodiments, the antibody is specific to a marker for cancer that is Mesothelin. In some embodiments, the antibody is specific to a marker for cancer that is VCAM-1. In some embodiments, the antibody is specific to a marker for cancer that is Methionine Aminopeptidase. In some embodiments, the antibody is specific to a marker for cancer that is VEGF. In some embodiments, the antibody is specific to a marker for cancer that is Methionine Aminopeptidase 2.

In some embodiments, the antibody is specific to a marker that is a marker for inflammation. In some embodiments, the antibody is specific to a marker that is a marker for inflammation that is ICAM-1. In some embodiments, the antibody is specific to a marker that is a marker for inflammation that is RANTES. In some embodiments, the antibody is specific to a marker that is a marker for inflammation that is MIP-2. In some embodiments, the antibody is specific to a marker that is a marker for inflammation that is MIP-1 beta. In some embodiments, the antibody is specific to a marker that is a marker for inflammation that is MIP-1 alpha. In some embodiments, the antibody is specific to a marker that is a marker for inflammation that is MMP-3.

In some embodiments, the antibody is specific to a marker that is a marker for endocrine function. In some embodiments, the antibody is specific to a marker that is a marker for endocrine function that is 17 beta-estradiol (E2). In some embodiments, the antibody is specific to a marker that is a marker for endocrine function that is DHEA. In some embodiments, the antibody is specific to a marker that is a marker for endocrine function that is ACTH. In some embodiments, the antibody is specific to a marker that is a marker for endocrine function that is gastrin. In some embodiments, the antibody is specific to a marker that is a marker for endocrine function that is growth hormone.

In some embodiments, the antibody is specific to a marker that is a marker for autoimmune disease. In some embodiments, the antibody is specific to a marker that is a marker for autoimmune disease that is GM-CSF. In some embodiments, the antibody is specific to a marker that is a marker for autoimmune disease that is C-reactive protein (CRP). In some embodiments, the antibody is specific to a marker that is a marker for autoimmune disease that is G-CSF.

In some embodiments, the antibody is specific to a marker for thyroid function. In some embodiments, the antibody is specific to a marker for thyroid function that is cyclic AMP. In some embodiments, the antibody is specific to a marker for thyroid function. In some embodiments, the antibody is specific to a marker for thyroid function that is calcitonin. In some embodiments, the antibody is specific to a marker for thyroid function. In some embodiments, the antibody is specific to a marker for thyroid function that is parathyroid hormone.

In some embodiments, the antibody is specific to a marker for cardiovascular function. In some embodiments, the antibody is specific to a marker for cardiovascular function that is B-natriuretic peptide. In some embodiments, the antibody is specific to a marker for cardiovascular function that is NT-proBNP. In some embodiments, the antibody is specific to a marker for cardiovascular function that is C-reactive protein, HS. In some embodiments, the antibody is specific to a marker for cardiovascular function that is beta-thromboglobulin. In some embodiments, the antibody is specific to a marker for cardiovascular function that is a cardiac troponin. In some embodiments, the antibody is specific to a marker for cardiovascular function that is cardiac troponin I. In some embodiments, the antibody is specific to a marker for cardiovascular function that is cardiac troponin T.

In some embodiments, the antibody is specific to a marker for diabetes. In some embodiments, the antibody is specific to a marker for diabetes that is C-peptide. In some embodiments, the antibody is specific to a marker for diabetes that is leptin.

In some embodiments, the antibody is specific to a marker for infectious disease. In some embodiments, the antibody is specific to a marker for infectious disease that is IFN gamma. In some embodiments, the antibody is specific to a marker for infectious disease that is IFN alpha. In some embodiments, the antibody is specific to a marker for infectious disease that is TREM-1.

In some embodiments, the antibody is specific to a marker for metabolism. In some embodiments, the antibody is specific to a marker for metabolism that is bio-intact PTH (1-84). In some embodiments, the antibody is specific to a marker for metabolism that is PTH.

In some embodiments, the antibody is specific to a marker that is IL-1 beta. In some embodiments, the antibody is specific to a marker that is TNF-alpha. In some embodiments, the antibody is specific to a marker that is IL-6. In some embodiments, the antibody is specific to a marker that is TnI (cardiac troponin I). In some embodiments, the antibody is specific to a marker that is IL-8.

In some embodiments, the antibody is specific to a marker that is Abeta 40. In some embodiments, the antibody is specific to a marker that is Abeta 42. In some embodiments, the antibody is specific to a marker that is cAMP. In some embodiments, the antibody is specific to a marker that is FAS Ligand. In some embodiments, the antibody is specific to a marker that is FGF-basic. In some embodiments, the antibody is specific to a marker that is GM-CSF. In some embodiments, the antibody is specific to a marker that is IFN-alpha. In some embodiments, the antibody is specific to a marker that is IFN-gamma. In some embodiments, the antibody is specific to a marker that is IL-1a. In some embodiments, the antibody is specific to a marker that is IL-2. In some embodiments, the antibody is specific to a marker that is IL-4. In some embodiments, the antibody is specific to a marker that is IL-5. In some embodiments, the antibody is specific to a marker that is IL-7. In some embodiments, the antibody is specific to a marker that is IL-12. In some embodiments, the antibody is specific to a marker that is IL-13. In some embodiments, the antibody is specific to a marker that is IL-17. In some embodiments, the antibody is specific to a marker that is MCP-1. In some embodiments, the antibody is specific to a marker that is MT-1a. In some embodiments, the antibody is specific to a marker that is RANTES. In some embodiments, the antibody is specific to a marker that is VEGF.

In some embodiments, the antibody is specific to a marker that is ACE. In some embodiments, the antibody is specific to a marker that is activin A. In some embodiments, the antibody is specific to a marker that is adiponectin. In some embodiments, the antibody is specific to a marker that is adipsin. In some embodiments, the antibody is specific to a marker that is AgRP. In some embodiments, the antibody is specific to a marker that is AKT1. In some embodiments, the antibody is specific to a marker that is albumin. In some embodiments, the antibody is specific to a marker that is betacellulin. In some embodiments, the antibody is specific to a marker that is bombesin. In some embodiments, the antibody is specific to a marker that is CD14. In some embodiments, the antibody is specific to a marker that is CD-26. In some embodiments, the antibody is specific to a marker that is CD-38. In some embodiments, the antibody is specific to a marker that is CD-40L. In some embodiments, the antibody is specific to a marker that is CD-40s. In some embodiments, the antibody is specific to a marker that is CDK5. In some embodiments, the antibody is specific to a marker that is Complement C3. In some embodiments, the antibody is specific to a marker that is Complement C4. In some embodiments, the antibody is specific to a marker that is C-peptide. In some embodiments, the antibody is specific to a marker that is CRP. In some embodiments, the antibody is specific to a marker that is EGF. In some embodiments, the antibody is specific to a marker that is E-selectin. In some embodiments, the antibody is specific to a marker that is FAS. In some embodiments, the antibody is specific to a marker that is FASLG. In some embodiments, the antibody is specific to a marker that is Fetuin A. In some embodiments, the antibody is specific to a marker that is fibrinogen. In some embodiments, the antibody is specific to a marker that is ghrelin. In some embodiments, the antibody is specific to a marker that is glucagon. In some embodiments, the antibody is specific to a marker that is growth hormone. In some embodiments, the antibody is specific to a marker that is haptoglobulin. In some embodiments, the antibody is specific to a marker that is hepatocyte growth factor. In some embodiments, the antibody is specific to a marker that is HGF. In some embodiments, the antibody is specific to a marker that is ICAM1. In some embodiments, the antibody is specific to a marker that is IFNG. In some embodiments, the antibody is specific to a marker that is IGF1. In some embodiments, the antibody is specific to a marker that is IL-1RA. In some embodiments, the antibody is specific to a marker that is Il-6sr In some embodiments, the antibody is specific to a marker that is IL-8. In some embodiments, the antibody is specific to a marker that is IL-10. In some embodiments, the antibody is specific to a marker that is IL-18. In some embodiments, the antibody is specific to a marker that is ILGFBP1. In some embodiments, the antibody is specific to a marker that is ILGFBP3. In some embodiments, the antibody is specific to a marker that is insulin-like growth factor 1. In some embodiments, the antibody is specific to a marker that is LEP. In some embodiments, the antibody is specific to a marker that is M-CSF. In some embodiments, the antibody is specific to a marker that is MMP2. In some embodiments, the antibody is specific to a marker that is MMP9. In some embodiments, the antibody is specific to a marker that is NGF. In some embodiments, the antibody is specific to a marker that is PAI-1. In some embodiments, the antibody is specific to a marker that is RAGE. In some embodiments, the antibody is specific to a marker that is RSP4. In some embodiments, the antibody is specific to a marker that is resistin. In some embodiments, the antibody is specific to a marker that is sex hormone binding globulin. In some embodiments, the antibody is specific to a marker that is SOCX3. In some embodiments, the antibody is specific to a marker that is TGF beta. In some embodiments, the antibody is specific to a marker that is thromboplastin. In some embodiments, the antibody is specific to a marker that is TNF R1. In some embodiments, the antibody is specific to a marker that is VCAM-1. In some embodiments, the antibody is specific to a marker that is VWF. In some embodiments, the antibody is specific to a marker that is TSH. In some embodiments, the antibody is specific to a marker that is EPITOME.

In some embodiments, the antibody is specific to a marker corresponding to the molecule of interest. In some embodiments, the antibody is specific to a marker that is cardiac troponin I. In some embodiments, the antibody is specific to a marker that is TREM-1. In some embodiments, the antibody is specific to a marker that is IL-6. In some embodiments, the antibody is specific to a marker that is IL-8. In some embodiments, the antibody is specific to a marker that is Leukotriene T4. In some embodiments, the antibody is specific to a marker that is Akt1. In some embodiments, the antibody is specific to a marker that is TGF-beta. In some embodiments, the antibody is specific to a marker that is Fas ligand.

A. Binding Partners

Any suitable binding partner with the requisite specificity for the form of molecule, e.g., a marker, to be detected can be used. If the molecule, e.g., a marker, has several different forms, various specificities of binding partners are possible. Suitable binding partners are known in the art and include antibodies, aptamers, lectins, and receptors. A useful and versatile type of binding partner is an antibody.

1. Antibodies

In some embodiments, the binding partner is an antibody specific for a molecule to be detected. The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. It will be appreciated that the choice of epitope or region of the molecule to which the antibody is raised will determine its specificity, e.g., for various forms of the molecule, if present, or for total (e.g., all, or substantially all, of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments that mimic antibodies can be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest, HyTest Ltd., Turku Finland; Abcam Inc., Cambridge, Mass., USA, Life Diagnostics, Inc., West Chester, Pa., USA; Fitzgerald Industries International, Inc., Concord, Mass. 01742-3049 USA; BiosPacific, Emeryville, Calif.).

In some embodiments, the antibody is a polyclonal antibody. In other embodiments, the antibody is a monoclonal antibody.

Capture binding partners and detection binding partner pairs, e.g., capture and detection antibody pairs, can be used in embodiments of the invention. Thus, in some embodiments, a heterogeneous assay protocol is used in which, typically, two binding partners, e.g., two antibodies, are used. One binding partner is a capture partner, usually immobilized on a solid support, and the other binding partner is a detection binding partner, typically with a detectable label attached. Such antibody pairs are available from the sources described above, e.g., BiosPacific, Emeryville, Calif. Antibody pairs can also be designed and prepared by methods well-known in the art. Compositions of the invention include antibody pairs wherein one member of the antibody pair is a label as described herein, and the other member is a capture antibody.

In some embodiments it is useful to use an antibody that cross-reacts with a variety of species, either as a capture antibody, a detection antibody, or both. Such embodiments include the measurement of drug toxicity by determining, e.g., release of cardiac troponin into the blood as a marker of cardiac damage. A cross-reacting antibody allows studies of toxicity to be done in one species, e.g. a non-human species, and direct transfer of the results to studies or clinical observations of another species, e.g., humans, using the same antibody or antibody pair in the reagents of the assays, thus decreasing variability between assays. Thus, in some embodiments, one or more of the antibodies for use as a binding partner to the marker of the molecule of interest, e.g., cardiac troponin, such as cardiac troponin I, can be a cross-reacting antibody. In some embodiments, the antibody cross-reacts with the marker, e.g. cardiac troponin, from at least two species selected from the group consisting of human, monkey, dog, and mouse. In some embodiments, the antibody cross-reacts with the marker, e.g., cardiac troponin, from the entire group consisting of human, monkey, dog, and mouse.

B. Fluorescent Moieties

In some embodiments of labels used in the invention, the binding partner, e.g., an antibody, is attached to a fluorescent moiety. The fluorescence of the moiety can be sufficient to allow detection in a single molecule detector, such as the single molecule detectors described herein.

A "fluorescent moiety," as that term is used herein, includes one or more fluorescent entities whose total fluorescence is such that the moiety can be detected in the single molecule detectors described herein. Thus, a fluorescent moiety can comprise a single entity (e.g., a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity can be attached to the binding partner separately or the entities can be attached together, as long as the entities as a group provide sufficient fluorescence to be detected.

Typically, the fluorescence of the moiety involves a combination of quantum efficiency and lack of photobleaching sufficient that the moiety is detectable above background levels in a single molecule detector, with the consistency necessary for the desired limit of detection, accuracy, and precision of the assay. For example, in some embodiments, the fluorescence of the fluorescent moiety is such that it allows detection and/or quantitation of a molecule, e.g., a marker, at a limit of detection of less than about 10, 5, 4, 3, 2, 1, 0.1, 0.01, 0.001, 0.00001, or 0.000001 pg/ml and with a coefficient of variation of less than about 20, 15, 14, 13, 12, 11, 10, 9, 8, 7, 6, 5, 4, 3, 2, 1% or less, e.g., about 10% or less, in the instruments described herein. In some embodiments, the fluorescence of the fluorescent moiety is such that it allows detection and/or quantitation of a molecule, e.g., a marker, at a limit of detection of less than about 5, 1, 0.5, 0.1, 0.05, 0.01, 0.005, 0.001 pg/ml and with a coefficient of variation of less than about 10%, in the instruments described herein.

"Limit of detection," as that term is used herein, includes the lowest concentration at which one can identify a sample as containing a molecule of the substance of interest, e.g., the first non-zero value. It can be defined by the variability of zeros and the slope of the standard curve. For example, the limit of detection of an assay can be determined by running a standard curve, determining the standard curve zero value, and adding two standard deviations to that value. A concentration of the substance of interest that produces a signal equal to this value is the "lower limit of detection" concentration.

Furthermore, the moiety has properties that are consistent with its use in the assay of choice. In some embodiments, the assay is an immunoassay, where the fluorescent moiety is attached to an antibody; the moiety must not aggregate with other antibodies or proteins, or must not undergo any more aggregation than is consistent with the required accuracy and precision of the assay. In some embodiments, fluorescent moieties that are preferred are fluorescent moieties, e.g., dye molecules that have a combination of: 1) high absorption coefficient; 2) high quantum yield; 3) high photostability (low photobleaching); and 4) compatibility with labeling the molecule of interest (e.g., protein) so that it can be analyzed using the analyzers and systems of the invention (e.g., does not cause precipitation of the protein of interest, or precipitation of a protein to which the moiety has been attached).

Fluorescent moieties, e.g., a single fluorescent dye molecule or a plurality of fluorescent dye molecules, which are useful in some embodiments of the invention, can be defined in terms of their photon emission characteristics when stimulated by EM radiation. For example, in some embodiments, the invention utilizes a fluorescent moiety, e.g., a moiety comprising a single fluorescent dye molecule or a plurality of fluorescent dye molecules, that is capable of emitting an average of at least about 10, 20, 30, 40, 50, 75, 100, 125, 150, 175, 200, 225, 250, 275, 300, 350, 400, 500, 600, 700, 800, 900, or 1000 photons when simulated by a laser emitting light at the excitation wavelength of the moiety, where the laser is focused on a spot of not less than about 5 microns in diameter that contains the moiety, and where the total energy directed at the spot by the laser is no more than about 3 microJoules. It will be appreciated that the total energy can be achieved by many different combinations of power output of the laser and length of time of exposure of the dye moiety. E.g., a laser of a power output of 1 mW can be used for 3 ms, 3 mW for 1 ms, 6 mW for 0.5 ms, 12 mW for 0.25 ms, and so on.

In some embodiments, the fluorescent moiety comprises an average of at least about 1, 2, 3, 4, 5, 6, 7, 8, 9, or 10 fluorescent entities, e.g., fluorescent molecules. In some embodiments, the fluorescent moiety comprises an average of no more than about 2, 3, 4, 5, 6, 7, 8, 9, 10, or 11 fluorescent entities, e.g., fluorescent molecules. In some embodiments, the fluorescent moiety comprises an average of about 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 fluorescent entities. In some embodiments, the fluorescent moiety comprises an average of about 2 to 8 fluorescent moieties are attached. In some embodiments, the fluorescent moiety comprises an average of about 2 to 6 fluorescent entities. In some embodiments, the fluorescent moiety comprises an average of about 2 to 4 fluorescent entities. In some embodiments, the fluorescent moiety comprises an average of about 3 to 10 fluorescent entities. In some embodiments, the fluorescent moiety comprises an average of about 3 to 8 fluorescent entities. In some embodiments, the fluorescent moiety comprises an average of about 3 to 6 fluorescent entities. By "average" it is meant that, in a given sample that is representative of a group of labels of the invention, where the sample contains a plurality of the binding partner-fluorescent moiety units, the molar ratio of the particular fluorescent entity to the binding partner, as determined by standard analytical methods, corresponds to the number or range of numbers specified. For example, in embodiments wherein the label comprises a binding partner that is an antibody and a fluorescent moiety that comprises a plurality of fluorescent dye molecules of a specific absorbance, a spectrophotometric assay can be used in which a solution of the label is diluted to an appropriate level and the absorbance at 280 nm is taken to determine the molarity of the protein (antibody) and an absorbance at, e.g., 650 nm (for Alexa Fluor 647), is taken to determine the molarity of the fluorescent dye molecule. The ratio of the latter molarity to the former represents the average number of fluorescent entities (dye molecules) in the fluorescent moiety attached to each antibody.

1. Dyes

In some embodiments, the invention uses fluorescent moieties that comprise fluorescent dye molecules. In some embodiments, the invention utilizes a fluorescent dye molecule that is capable of emitting an average of at least about 50 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 75 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 100 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 150 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 200 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules.

In some embodiments, the invention uses a fluorescent dye moiety, e.g., a single fluorescent dye molecule or a plurality of fluorescent dye molecules, that is capable of emitting an average of at least about 50 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 100 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 150 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 300 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 500 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules.

A non-inclusive list of useful fluorescent entities for use in the fluorescent moieties of the invention is given in Table 2, below. In some embodiments, the fluorescent dye is selected from the group consisting of Alexa Fluor 488, Alexa Fluor 532, Alexa Fluor 647, Alexa Fluor 700, Alexa Fluor 750, Fluorescein, B-phycoerythrin, allophycocyanin, PBXL-3, and Qdot 605. In some embodiments, the fluorescent dye is selected from the group consisting of Alexa Fluor 488, Alexa Fluor 532, Alexa Fluor 700, Alexa Fluor 750, Fluorescein, B-phycoerythrin, allophycocyanin, PBXL-3, and Qdot 605.

TABLE 2

FLUORESCENT ENTITIES

| Dye | E Ex (mu) | E (M)−1 | Em (nm) | MMw |
|---|---|---|---|---|
| Bimane | 380 | 5,700 | 458 | 282.31 |
| Dapoxyl | 373 | 22,000 | 551 | 362.83 |
| Dimethylamino coumarin-4-acetic acid | 375 | 22,000 | 470 | 344.32 |
| Marina blue | 365 | 19,000 | 460 | 367.26 |
| 8-Anilino naphthalene-1-sulfonic acid | 372 | | 480 | |
| Cascade blue | 376 | 23,000 | 420 | 607.42 |
| Alexa Fluor 405 | 402 | 35,000 | 421 | 1028.26 |
| Cascade blue | 400 | 29,000 | 420 | 607.42 |
| Cascade yellow | 402 | 24,000 | 545 | 563.54 |
| Pacific blue | 410 | 46,000 | 455 | 339.21 |
| PyMPO | 415 | 26,000 | 570 | 582.41 |
| Alexa Fluor 430 | 433 | 15,000 | 539 | 701.75 |
| Atto-425 | 438 | | 486 | |
| NBD | 465 | 22,000 | 535 | 391.34 |
| Alexa Fluor 488 | 495 | 73,000 | 519 | 643.41 |
| Fluorescein | 494 | 79,000 | 518 | 376.32 |
| Oregon Green 488 | 496 | 76,000 | 524 | 509.38 |
| Atto 495 | 495 | | 522 | |
| Cy2 | 489 | 150,000 | 506 | 713.78 |
| DY-480-XL | 500 | 40,000 | 630 | 514.60 |
| DY-485-XL | 485 | 20,000 | 560 | 502.59 |
| DY-490-XL | 486 | 27,000 | 532 | 536.58 |
| DY-500-XL | 505 | 90,000 | 555 | 596.68 |
| DY-520-XL | 520 | 40,000 | 664 | 514.60 |
| Alexa Fluor 532 | 531 | 81,000 | 554 | 723.77 |
| BODIPY 530/550 | 534 | 77,000 | 554 | 513.31 |
| 6-HEX | 535 | 98,000 | 556 | 680.07 |
| 6-JOE | 522 | 75,000 | 550 | 602.34 |
| Rhodamine 6G | 525 | 108,000 | 555 | 555.59 |
| Atto-520 | 520 | | 542 | |
| Cy3B | 558 | 130,000 | 572 | 658.00 |
| Alexa Fluor 610 | 612 | 138,000 | 628 | |
| Alexa Fluor 633 | 632 | 159,000 | 647 | ca. 1200 |
| Alexa Fluor 647 | 650 | 250,000 | 668 | ca. 1250 |
| BODIPY 630/650 | 625 | 101,000 | 640 | 660.50 |
| Cy5 | 649 | 250,000 | 670 | 791.99 |
| Alexa Fluor 660 | 663 | 110,000 | 690 | |
| Alexa Fluor 680 | 679 | 184,000 | 702 | |
| Alexa Fluor 700 | 702 | 192,000 | 723 | |
| Alexa Fluor 750 | 749 | 240,000 | 782 | |
| B-phycoerythrin | 546, 565 480, 546, | 2,410,000 | 575 | 240,000 |
| R-phycoerythrin | 565 | 1,960,000 | 578 | 240,000 |
| Allophycocyanin | 650 | 700,000 | 660 | 700,000 |
| PBXL-1 | 545 | | 666 | |
| PBXL-3 | 614 | | 662 | |

Atto-tec dyes

| Name | Ex (nm) | Em (nm) | QY | □ (ns) |
|---|---|---|---|---|
| Atto 425 | 436 | 486 | 0.9 | 3.5 |
| Atto 495 | 495 | 522 | 0.45 | 2.4 |
| Atto 520 | 520 | 542 | 0.9 | 3.6 |
| Atto 560 | 561 | 585 | 0.92 | 3.4 |

TABLE 2-continued

FLUORESCENT ENTITIES

| label | Ex (nm) | | Em (nm) | |
|---|---|---|---|---|
| Atto 590 | 598 | 634 | 0.8 | 3.7 |
| Atto 610 | 605 | 630 | 0.7 | 3.3 |
| Atto 655 | 665 | 690 | 0.3 | 1.9 |
| Atto 680 | 680 | 702 | 0.3 | 1.8 |

Dyomics Fluors

| label | Ex (nm) | Molar absorbance* [1·mol−1·cm−1] | Em (nm) | molecular weight# [g·mol−1] |
|---|---|---|---|---|
| DY-495/5 | 495 | 70,000 | 520 | 489.47 |
| DY-495/6 | 495 | 70,000 | 520 | 489.47 |
| DY-495X/5 | 495 | 70,000 | 520 | 525.95 |
| DY-495X/6 | 495 | 70,000 | 520 | 525.95 |
| DY-505/5 | 505 | 85,000 | 530 | 485.49 |
| DY-505/6 | 505 | 85,000 | 530 | 485.49 |
| DY-505X/5 | 505 | 85,000 | 530 | 523.97 |
| DY-505X/6 | 505 | 85,000 | 530 | 523.97 |
| DY-550 | 553 | 122.000 | 578 | 667.76 |
| DY-555 | 555 | 100.000 | 580 | 636.18 |
| DY-610 | 609 | 81.000 | 629 | 667.75 |
| DY-615 | 621 | 200.000 | 641 | 578.73 |
| DY-630 | 636 | 200.000 | 657 | 634.84 |
| DY-631 | 637 | 185.000 | 658 | 736.88 |
| DY-633 | 637 | 180.000 | 657 | 751.92 |
| DY-635 | 647 | 175.000 | 671 | 658.86 |
| DY-636 | 645 | 190.000 | 671 | 760.91 |
| DY-650 | 653 | 170.000 | 674 | 686.92 |
| DY-651 | 653 | 160.000 | 678 | 888.96 |
| DYQ-660 | 660 | 117,000 | — | 668.86 |
| DYQ-661 | 661 | 116,000 | — | 770.90 |
| DY-675 | 674 | 110.000 | 699 | 706.91 |
| DY-676 | 674 | 145.000 | 699 | 807.95 |
| DY-680 | 690 | 125.000 | 709 | 634.84 |
| DY-681 | 691 | 125.000 | 708 | 736.88 |
| DY-700 | 702 | 96.000 | 723 | 668.86 |
| DY-701 | 706 | 115.000 | 731 | 770.90 |
| DY-730 | 734 | 185.000 | 750 | 660.88 |
| DY-731 | 736 | 225.000 | 759 | 762.92 |
| DY-750 | 747 | 240.000 | 776 | 712.96 |
| DY-751 | 751 | 220.000 | 779 | 814.99 |
| DY-776 | 771 | 147.000 | 801 | 834.98 |
| DY-780-OH | 770 | 70.000 | 810 | 757.34 |
| DY-780-P | 770 | 70.000 | 810 | 957.55 |
| DY-781 | 783 | 98.000 | 800 | 762.92 |
| DY-782 | 782 | 102.000 | 800 | 660.88 |
| EVOblue-10 | 651 | 101.440 | 664 | 389.88 |
| EVOblue-30 | 652 | 102.000 | 672 | 447.51 |

Quantum Dots: Qdot 525, QD 565, QD 585, QD 605, QD 655, QD 705, QD 800

Suitable dyes for use in the invention include modified carbocyanine dyes. On such modification comprises modification of an indolium ring of the carbocyanine dye to permit a reactive group or conjugated substance at the number three position. The modification of the indolium ring provides dye conjugates that are uniformly and substantially more fluorescent on proteins, nucleic acids and other biopolymers, than conjugates labeled with structurally similar carbocyanine dyes bound through the nitrogen atom at the number one position. In addition to having more intense fluorescence emission than structurally similar dyes at virtually identical wavelengths, and decreased artifacts in their absorption spectra upon conjugation to biopolymers, the modified carbocyanine dyes have greater photostability and higher absorbance (extinction coefficients) at the wavelengths of peak absorbance than the structurally similar dyes. Thus, the modified carbocyanine dyes result in greater sensitivity in assays using the modified dyes and their conjugates. Preferred modified dyes include compounds that have at least one substituted indolium ring system in which the substituent on the 3-carbon of the indolium ring contains a chemically reactive group or a conjugated substance. Other dye compounds include compounds that incorporate an azabenzazolium ring moiety and at least one sulfonate moiety. The modified carbocyanine dyes that can be used to detect individual molecules in various embodiments of the invention are described in U.S. Pat. No. 6,977,305, which is herein incorporated by reference in its entirety. Thus, in some embodiments the labels of the invention utilize a fluorescent dye that includes a substituted indolium ring system in which the substituent on the 3-carbon of the indolium ring contains a chemically reactive group or a conjugated substance group.

In some embodiments, the label comprises a fluorescent moiety that includes one or more Alexa Fluor dyes (Molecular Probes, Eugene, Oreg.). The Alexa Fluor dyes are disclosed in U.S. Pat. Nos. 6,977,305; 6,974,874; 6,130,101; and 6,974,305 which are herein incorporated by reference in their entirety. Some embodiments of the invention utilize a dye chosen from the group consisting of Alexa Fluor 647, Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize a dye chosen from the group consisting of Alexa Fluor 488, Alexa Fluor 532, Alexa Fluor 647, Alexa Fluor 700 and Alexa Fluor 750. Some embodiments of the invention utilize a dye chosen from the group consisting of Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize the Alexa Fluor 647 molecule, which has an absorption maximum between about 650 and 660 nm and an emission maximum between about 660 and 670 nm. The Alexa Fluor 647 dye is used alone or in combination with other Alexa Fluor dyes.

Currently available organic fluors can be improved by rendering them less hydrophobic by adding hydrophilic groups such as polyethylene. Alternatively, currently sulfonated organic fluors such as the Alexa Fluor 647 dye can be rendered less acidic by making them zwitterionic. Particles such as antibodies that are labeled with the modified fluors are less likely to bind non-specifically to surfaces and proteins in immunoassays, and thus enable assays that have greater sensitivity and lower backgrounds. Methods for modifying and improving the properties of fluorescent dyes for the purpose of increasing the sensitivity of a system that detects single molecules are known in the art. Preferably, the modification improves the Stokes shift while maintaining a high quantum yield.

2. Quantum Dots

In some embodiments, the fluorescent label moiety that is used to detect a molecule in a sample using the analyzer systems of the invention is a quantum dot. Quantum dots (QDs), also known as semiconductor nanocrystals or artificial atoms, are semiconductor crystals that contain anywhere between 100 to 1,000 electrons and range from 2-10 nm. Some QDs can be between 10-20 nm in diameter. QDs have high quantum yields, which makes them particularly useful for optical applications. QDs are fluorophores that fluoresce by forming excitons, which are similar to the excited state of traditional fluorophores, but have much longer lifetimes of up to 200 nanoseconds. This property provides QDs with low photobleaching. The energy level of QDs can be controlled by changing the size and shape of the QD, and the depth of the QDs' potential. One optical features of small excitonic QDs is coloration, which is determined by the size of the dot. The larger the dot, the redder, or more towards the red end of the spectrum the fluorescence. The smaller the dot, the bluer or more towards the blue end it is. The bandgap energy that determines the energy and hence the color of the fluoresced light is inversely proportional to the square of the size of the QD. Larger QDs have more energy levels which are more closely spaced, thus allowing the QD to absorb photons containing less energy, i.e., those closer to the red end of the spectrum. Because the emission frequency of a dot is dependent on the bandgap, it is possible to control the output wavelength of a dot with extreme precision. In some embodiments the protein that is detected with the single molecule analyzer system is labeled with a QD. In some embodiments, the single molecule analyzer is used to detect a protein labeled with one QD and using a filter to allow for the detection of different proteins at different wavelengths.

QDs have broad excitation and narrow emission properties which, when used with color filtering, require only a single electromagnetic source to resolve individual signals during multiplex analysis of multiple targets in a single sample. Thus, in some embodiments, the analyzer system comprises one continuous wave laser and particles that are each labeled with one QD. Colloidally prepared QDs are free floating and can be attached to a variety of molecules via metal coordinating functional groups. These groups include but are not limited to thiol, amine, nitrile, phosphine, phosphine oxide, phosphonic acid, carboxylic acids or other ligands. By bonding appropriate molecules to the surface, the quantum dots can be dispersed or dissolved in nearly any solvent or incorporated into a variety of inorganic and organic films. Quantum dots (QDs) can be coupled to streptavidin directly through a maleimide ester coupling reaction or to antibodies through a meleimide-thiol coupling reaction. This yields a material with a biomolecule covalently attached on the surface, which produces conjugates with high specific activity. In some embodiments, the protein that is detected with the single molecule analyzer is labeled with one quantum dot. In some embodiments, the quantum dot is between 10 and 20 nm in diameter. In other embodiments, the quantum dot is between 2 and 10 nm in diameter. In other embodiments, the quantum dot is about 2 nm, 3 nm, 4 nm, 5 nm, 6 nm, 7 nm, 8 nm, 9 nm, 10 nm, 11 nm, 12 nm, 13 nm, 14 nm, 15 v, 16 nm, 17 nm, 18 nm, 19 nm or 20 nm in diameter. Useful Quantum Dots comprise QD 605, QD 610, QD 655, and QD 705. A preferred Quantum Dot is QD 605.

C. Binding Partner-Fluorescent Moiety Compositions

The labels of the invention generally contain a binding partner, e.g., an antibody, bound to a fluorescent moiety to provide the requisite fluorescence for detection and quantitation in the instruments described herein. Any suitable combination of binding partner and fluorescent moiety for detection in the single molecule detectors described herein can be used as a label in the invention. In some embodiments, the invention provides a label for a marker of a biological state, where the label includes an antibody to the marker and a fluorescent moiety. The marker can be any of the markers described above. The antibody can be any antibody as described above. A fluorescent moiety can be attached such that the label is capable of emitting an average of at least about 50, 75, 100, 125, 150, 175, 200, 225, 250, 275, 300, 350, 400, 500, 600, 700, 800, 900, or 1000 photons when simulated by a laser emitting light at the excitation wavelength of the moiety, where the laser is focused on a spot of not less than about 5 microns in diameter that contains the label, and wherein the total energy directed at the spot by the laser is no more than about 3 microJoules. In some embodiments, the fluorescent moiety can be a fluorescent moiety that is capable of emitting an average of at least about 50, 100, 150, or 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. The fluorescent moiety can comprise one or more dye molecules with a structure that includes a substituted indolium ring system wherein the substituent on the 3-carbon of the indolium ring contains a chemically reactive group or a conjugated substance group. The label composition can include a fluorescent moiety that includes one or more dye molecules selected from the group consisting of Alexa Fluor 488, Alexa Fluor 532, Alexa Fluor 647, Alexa Fluor 700, or Alexa Fluor 750. The label composition can include a fluorescent moiety that includes one or more dye molecules selected from the group consisting of Alexa Fluor 488, Alexa Fluor 532, Alexa Fluor 700, or Alexa Fluor 750. The label composition can include a fluorescent moiety that includes one or more dye molecules that are Alexa Fluor 488. The label composition can include a fluorescent moiety that includes one or more dye molecules that are Alexa Fluor 555. The label composition can include a fluorescent moiety that includes one or more dye molecules that are Alexa Fluor 610. The label composition can include a fluorescent moiety that includes one or more dye molecules that are Alexa Fluor 647. The label composition can include a fluorescent moiety that includes one or more dye molecules that are Alexa Fluor 680. The label composition can include a fluorescent moiety that includes one or more dye molecules that are Alexa Fluor 700. The label composition can include a fluorescent moiety that includes one or more dye molecules that are Alexa Fluor 750.

In some embodiments, the invention provides a composition for the detection of a marker of a biological state that includes an Alexa Fluor molecule, e.g. an Alexa Fluor molecule selected from the described groups, such as an Alexa Fluor 647 molecule attached to an antibody specific for the marker. In some embodiments the composition includes an average of about 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 Alexa Fluor 647 molecules attached to an antibody that can detect the marker. In some embodiments the invention provides a composition for the detection a marker of a biological state that includes an average of about 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 Alexa Fluor 647 molecules attached to an antibody specific to the marker. In some embodiments the invention provides a composition for the detection of a marker of a biological state that includes an average of about 2 to 10 Alexa Fluor 647 molecules molecule attached to an antibody specific to the marker. In some embodiments the invention provides a composition for the detection of a marker of a biological state that includes an average of about 2 to 8 Alexa Fluor 647 molecules molecule attached to an antibody specific to the marker. In some embodiments the invention provides a composition for the detection of a marker of a biological state that includes an average of about 2 to 6 Alexa Fluor 647 molecules molecule attached to an antibody specific to the marker. In some embodiments the invention provides a composition for the detection of a marker of a biological state that includes an average of about 2 to 4 Alexa Fluor 647 molecules molecule attached to an antibody specific to the marker. In some embodiments the invention provides a composition for the detection of a marker of a biological state that includes an average of about 3 to 8 Alexa Fluor 647 molecules molecule attached to an antibody specific to the marker. In some embodiments the invention provides a composition for the detection of a marker of a biological state that includes an average of about 3 to 6 Alexa Fluor 647 molecules molecule attached to an antibody specific to the marker. In some embodiments the invention provides a composition for the detection of a marker of a biological state that includes an average of about 4 to 8 Alexa Fluor 647 molecules molecule attached to an antibody specific to the marker.

Attachment of the fluorescent moiety, or fluorescent entities that make up the fluorescent moiety, to the binding partner, e.g., an antibody, can be by any suitable means; such methods are well-known in the art and exemplary methods are given in the Examples. In some embodiments, after attachment of the fluorescent moiety to the binding partner to form a label for use in the methods of the invention, and prior to the use of the label for labeling the marker of interest, it is useful to perform a filtration step. E.g., an antibody-dye label can be filtered prior to use, e.g., through a 0.2 micron filter, or any suitable filter for removing aggregates. Other reagents for use in the assays of the invention can also be filtered, e.g., through a 0.2 micron filter, or any suitable filter. Without being bound by theory, it is thought that such filtration removes a portion of the aggregates of the, e.g., antibody-dye labels. Such aggregates can bind as a unit to the protein of interest, but, upon release in elution buffer, the aggregates are likely to disaggregate. Therefore false positives can result when several labels are detected from an aggregate that has bound to only a single protein molecule of interest. Regardless of theory, filtration has been found to reduce false positives in the subsequent assay and to improve accuracy and precision.

It will be appreciated that immunoassays often employ a sandwich format in which binding partner pairs, e.g. antibodies, to the same molecule, e.g., a marker, are used. The invention also encompasses binding partner pairs, e.g., antibodies, wherein both antibodies are specific to the same molecule, e.g., the same marker, and wherein at least one member of the pair is a label as described herein. Thus, for any label that includes a binding-partner and a fluorescent moiety, the invention also encompasses a pair of binding partners wherein the first binding partner, e.g., an antibody, is part of the label, and the second binding partner, e.g., an antibody, is, typically, unlabeled and serves as a capture binding partner. In addition, binding partner pairs are frequently used in FRET assays. FRET assays useful in the invention are disclosed in U.S. patent application Ser. No. 11/048,660, incorporated by reference herein in its entirety, and the present invention also encompasses binding partner pairs, each of which includes a FRET label.

V. Highly Sensitive Analysis of Molecules

In one aspect, the invention provides a method for determining the presence or absence of a single molecule, e.g., a molecule of a marker, in a sample, by: i) labeling the molecule if present, with a label; and ii) detecting the presence or absence of the label, wherein the detection of the presence of the label indicates the presence of the single molecule in the sample. In some embodiments, the method is capable of detecting the molecule at a limit of detection of less than about 100, 80, 60, 50, 40, 30, 20, 15, 12, 10, 9, 8, 7, 6, 5, 4, 3, 2, 1, 0.9, 0.8, 0.7, 0.6, 0.5, 0.4, 0.3, 0.2, 0.1, 0.05, 0.01, 0.005, or 0.001 femtomolar. In some embodiments, the method is capable of detecting the molecule at a limit of detection of less than about 100 femtomolar. In some embodiments, the method is capable of detecting the molecule at a limit of detection of less than about 10 femtomolar. In some embodiments, the method is capable of detecting the molecule at a limit of detection of less than about 1 femtomolar. In some embodiments, the method is capable of detecting the molecule at a limit of detection of less than about 0.1 femtomolar. In some embodiments, the method is capable of detecting the molecule at a limit of detection of less than about 0.01 femtomolar. In some embodiments, the method is capable of detecting the molecule at a limit of detection of less than about 0.001 femtomolar. Detection limits can be determined by use of an appropriate standard, e.g., National Institute of Standards and Technology reference standard material.

The methods also provide methods of determining a concentration of a molecule, e.g., a marker indicative of a biological state, in a sample by detecting single molecules of the molecule in the sample. The "detecting" of a single molecule includes detecting the molecule directly or indirectly. In the case of indirect detection, labels that correspond to single molecules, e.g., labels attached to the single molecules, can be detected.

In some embodiments, the invention provides a method for determining the presence or absence of a single molecule of a protein in a biological sample, comprising labeling the molecule with a label and detecting the presence or absence of the label in a single molecule detector, wherein the label comprises a fluorescent moiety that is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. The single molecule detector may, in some embodiments, comprise not more than one interrogation space. The limit of detection of the single molecule in the sample can be less than about 10, 1, 0.1, 0.01, or 0.001 femtomolar. In some embodiments, the limit of detection is less than about 1 femtomolar. The detecting can comprise detecting electromagnetic radiation emitted by the fluorescent moiety. The method can further comprise exposing the fluorescent moiety to electromagnetic radiation, e.g., electromagnetic radiation provided by a laser, such as a laser with a power output of about 2, 3, 4, 5, 6, 7, 8, 9, 10, 11, 12, 13, 14, 15, 16, 17, 18, 19, or 20 mW. In some embodiments, the laser stimulus provides light to the interrogation space for between about 10 to 1000 microseconds, or about 1000, 250, 100, 50, 25 or 10 microseconds. In some embodiments, the label further comprises a binding partner specific for binding the molecule, such as an antibody. In some embodiments, the fluorescent moiety comprises a fluorescent dye molecule, such as a dye molecule that comprises at least one substituted indolium ring system in which the substituent on the 3-carbon of the indolium ring contains a chemically reactive group or a conjugated substance. In some embodiments, the dye molecule is an Alexa Fluor molecule selected from the group consisting of Alexa Fluor 488, Alexa Fluor 532, Alexa Fluor 647, Alexa Fluor 680 or Alexa Fluor 700. In some embodiments, the dye molecule is an Alexa Fluor 647 dye molecule. In some embodiments, the fluorescent moiety comprises a plurality of Alexa Fluor 647 molecules. In some embodiments, the plurality of Alexa Fluor 647 molecules comprises about 2 to 4 Alexa Fluor 647 molecules, or about 3 to 6 Alexa Fluor 647 molecules. In some embodiments, the fluorescent moiety is a quantum dot. The method can further comprise measuring the concentration of the protein in the sample.

In some embodiments, detecting the presence or absence of the label comprises: (i) directing electromagnetic radiation from an electromagnetic radiation source to an interrogation space; (ii) providing electromagnetic radiation that is sufficient to stimulate the label, such as a fluorescent moiety, to emit photons if the label is present in the interrogation space;

(iii) translating the interrogation space through the sample thereby moving the interrogation space to detect the presence or absence of other single molecules; and (iv) detecting photons emitted during the exposure of step (ii). The method can further comprise determining a background photon level in the interrogation space, wherein the background level represents the average photon emission of the interrogation space when it is subjected to electromagnetic radiation in the same manner as in step (ii), but without label in the interrogation space. The method can further comprise comparing the amount of photons detected in step (iv) to a threshold photon level, wherein the threshold photon level is a function of the background photon level, wherein an amount of photons detected in step (iv) greater that the threshold level indicates the presence of the label, and an amount of photons detected in step (iv) equal to or less than the threshold level indicates the absence of the label.

A. Sample

The sample can be any suitable sample. Typically, the sample is a biological sample, e.g., a biological fluid. Such fluids include, without limitation, bronchoalveolar lavage fluid (BAL), blood, serum, plasma, urine, nasal swab, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which can contain the target particle of interest. Other similar specimens such as cell or tissue culture or culture broth are also of interest.

In some embodiments, the sample is a blood sample. In some embodiments the sample is a plasma sample. In some embodiments the sample is a serum sample. In some embodiments, the sample is a urine sample. In some embodiments, the sample is a nasal swab.

B. Sample Preparation

In general, any method of sample preparation can be used that produces a label corresponding to a molecule of interest, e.g., a marker of a biological state to be measured, where the label is detectable in the instruments described herein. As is known in the art, sample preparation in which a label is added to one or more molecules can be performed in a homogeneous or heterogeneous format. In some embodiments, the sample preparation is formed in a homogenous format. In analyzer systems employing a homogenous format, unbound label is not removed from the sample. See, e.g., U.S. patent application Ser. No. 11/048,660. In some embodiments, the particle or particles of interest are labeled by addition of labeled antibody or antibodies that bind to the particle or particles of interest.

In some embodiments, a heterogeneous assay format is used, wherein, typically, a step is employed for removing unbound label. Such assay formats are well-known in the art. One particularly useful assay format is a sandwich assay, e.g., a sandwich immunoassay. In this format, the molecule of interest, e.g., a marker of a biological state, is captured, e.g., on a solid support, using a capture binding partner. Unwanted molecules and other substances can then optionally be washed away, followed by binding of a label comprising a detection binding partner and a detectable label, e.g., a fluorescent moiety. Further washes remove unbound label, then the detectable label is released, usually though not necessarily still attached to the detection binding partner. In alternative embodiments, sample and label are added to the capture binding partner without a wash in between, e.g., at the same time. Other variations will be apparent to one of skill in the art.

In some embodiments, the method for detecting the molecule of interest, e.g., a marker of a biological state, uses a sandwich assay with antibodies, e.g., monoclonal antibodies, as capture binding partners. The method comprises binding molecules in a sample to a capture antibody that is immobilized on a binding surface, and binding the label comprising a detection antibody to the molecule to form a "sandwich" complex. The label comprises the detection antibody and a fluorescent moiety, as described herein, which is detected, e.g., using the single molecule analyzers of the invention. Both the capture and detection antibodies specifically bind the molecule. Many examples of sandwich immunoassays are known, and some are described in U.S. Pat. No. 4,168,146 to Grubb et al. and U.S. Pat. No. 4,366,241 to Tom et al., both of which are incorporated herein by reference. Further examples specific to specific markers are described in the Examples.

The capture binding partner can be attached to a solid, support, e.g., a microtiter plate or paramagnetic beads. In some embodiments, the invention provides a binding partner for a molecule of interest, e.g., a marker of a biological state, attached to a paramagnetic bead. Any suitable binding partner that is specific for the molecule that it is wished to capture can be used. The binding partner can be an antibody, e.g., a monoclonal antibody. Production and sources of antibodies are described elsewhere herein. It will be appreciated that antibodies identified herein as useful as a capture antibody can also be useful as detection antibodies, and vice versa.

The attachment of the binding partner, e.g., an antibody, to the solid support can be covalent or noncovalent. In some embodiments, the attachment is noncovalent. An example of a noncovalent attachment well-known in the art is that between biotin-avidin and streptavidin. Thus, in some embodiments, a solid support, e.g., a microtiter plate or a paramagnetic bead, is attached to the capture binding partner, e.g., an antibody, through noncovalent attachment, e.g., biotin-avidin/streptavidin interactions. In some embodiments, the attachment is covalent. Thus, in some embodiments, a solid support, e.g., a microtiter plate or a paramagnetic bead, is attached to the capture binding partner, e.g., an antibody, through covalent attachment.

The capture antibody can be covalently attached in an orientation that optimizes the capture of the molecule of interest. For example, in some embodiments, a binding partner, e.g., an antibody, is attached in a orientated manner to a solid support, e.g., a microtiter plate or a paramagnetic microparticle.

An exemplary protocol for oriented attachment of an antibody to a solid support is as follows. IgG is dissolved in 0.1 M sodium acetate buffer, pH 5.5 to a final concentration of 1 mg/ml. An equal volume of ice cold 20 mM sodium periodate in 0.1 M sodium acetate, pH 5.5 is added. The IgG is allowed to oxidize for ½ hour on ice. Excess periodate reagent is quenched by the addition of 0.15 volume of 1 M glycerol. Low molecular weight byproducts of the oxidation reaction are removed by ultrafiltration. The oxidized IgG fraction is diluted to a suitable concentration (typically 0.5 mg/ml IgG) and reacted with hydrazide-activated multiwell plates for at least two hours at room temperature. Unbound IgG is removed by washing the multiwell plate with borate buffered saline or another suitable buffer. The plate can be dried for storage if desired. A similar protocol can be followed to attach antibodies to microbeads if the material of the microbead is suitable for such attachment.

In some embodiments, the solid support is a microtiter plate. In some embodiments, the solid support is a paramagnetic bead. An exemplary paramagnetic bead is Streptavidin C1(Dynal, 650.01-03). Other suitable beads will be apparent to those of skill in the art. Methods for attachment of antibodies to paramagnetic beads are well-known in the art. One example is given in Example 2.

The molecule of interest is contacted with the capture binding partner, e.g., capture antibody immobilized on a solid support. Some sample preparation can be used, e.g., preparation of serum from blood samples or concentration procedures before the sample is contacted with the capture antibody. Protocols for binding of proteins in immunoassays are well-known in the art and are included in the Examples.

The time allowed for binding will vary depending on the conditions; it will be apparent that shorter binding times are desirable in some settings, especially in a clinical setting. The use of, e.g., paramagnetic beads can reduce the time required for binding. In some embodiments, the time allowed for binding of the molecule of interest to the capture binding partner, e.g., an antibody, is less that about 12, 10, 8, 6, 4, 3, 2, or 1 hours, or less than about 60, 50, 40, 30, 25, 20, 15, 10, or 5 minutes. In some embodiments, the time allowed for binding of the molecule of interest to the capture binding partner, e.g., an antibody, is less than about 60 minutes. In some embodiments, the time allowed for binding of the molecule of interest to the capture binding partner, e.g., an antibody, is less than about 40 minutes. In some embodiments, the time allowed for binding of the molecule of interest to the capture binding partner, e.g., an antibody, is less than about 30 minutes. In some embodiments, the time allowed for binding of the molecule of interest to the capture binding partner, e.g., an antibody, is less than about 20 minutes. In some embodiments, the time allowed for binding of the molecule of interest to the capture binding partner, e.g., an antibody, is less than about 15 minutes. In some embodiments, the time allowed for binding of the molecule of interest to the capture binding partner, e.g., an antibody, is less than about 10 minutes. In some embodiments, the time allowed for binding of the molecule of interest to the capture binding partner, e.g., an antibody, is less than about 5 minutes.

In some embodiments, following the binding of particles of the molecule of interest to the capture binding partner, e.g., a capture antibody, particles that bound nonspecifically, as well as other unwanted substances in the sample, are washed away leaving substantially only specifically bound particles of the molecule of interest. In other embodiments, no wash is used between additions of sample and label, which can reduce sample preparation time. Thus, in some embodiments, the time allowed for both binding of the molecule of interest to the capture binding partner, e.g., an antibody, and binding of the label to the molecule of interest, is less that about 12, 10, 8, 6, 4, 3, 2, or 1 hours, or less than about 60, 50, 40, 30, 25, 20, 15, 10, or 5 minutes. In some embodiments, the time allowed for both binding of the molecule of interest to the capture binding partner, e.g., an antibody, and binding of the label to the molecule of interest, is less that about 60 minutes. In some embodiments, the time allowed for both binding of the molecule of interest to the capture binding partner, e.g., an antibody, and binding of the label to the molecule of interest, is less than about 40 minutes. In some embodiments, the time allowed for both binding of the molecule of interest to the capture binding partner, e.g., an antibody, and binding of the label to the molecule of interest, is less than about 30 minutes. In some embodiments, the time allowed for both binding of the molecule of interest to the capture binding partner, e.g., an antibody, and binding of the label to the molecule of interest, is less than about 20 minutes. In some embodiments, the time allowed for both binding of the molecule of interest to the capture binding partner, e.g., an antibody, and binding of the label to the molecule of interest, is less than about 15 minutes. In some embodiments, the time allowed for both binding of the molecule of interest to the capture binding partner, e.g., an antibody, and binding of the label to the molecule of interest, is less than about 10 minutes. In some embodiments, the time allowed for both binding of the molecule of interest to the capture binding partner, e.g., an antibody, and binding of the label to the molecule of interest, is less than about 5 minutes.

Some immunoassay diagnostic reagents, including the capture and signal antibodies used to measure the molecule of interest, can be derived from animal sera. Endogenous human heterophilic antibodies, or human anti-animal antibodies, which have the ability to bind to immunoglobulins of other species, are present in the serum or plasma of more than 10% of patients. These circulating heterophilic antibodies can interfere with immunoassay measurements. In sandwich immunoassays, these heterophilic antibodies can either bridge the capture and detection (diagnostic) antibodies, thereby producing a false-positive signal, or they can block the binding of the diagnostic antibodies, thereby producing a false-negative signal. In competitive immunoassays, the heterophilic antibodies can bind to the analytic antibody and inhibit its binding to the molecule of interest. They can also either block or augment the separation of the antibody-molecule of interest complex from free molecule of interest, especially when antispecies antibodies are used in the separation systems. Therefore, the impact of these heterophilic antibody interferences is difficult to predict and it can be advantageous to block the binding of heterophilic antibodies. In some embodiments of the invention, the immunoassay includes the step of depleting the sample of heterophilic antibodies using one or more heterophilic antibody blockers. Methods for removing heterophilic antibodies from samples to be tested in immunoassays are known and include: heating the specimen in a sodium acetate buffer, pH 5.0, for 15 minutes at 90° C. and centrifuging at 1200 g for 10 minutes; precipitating the heterophilic immunoglobulins using polyethylene glycol (PEG); immunoextracting the interfering heterophilic immunoglobulins from the specimen using protein A or protein G; or adding nonimmune mouse IgG. Embodiments of the methods of the invention contemplate preparing the sample prior to analysis with the single molecule detector. The appropriateness of the method of pretreatment can be determined. Biochemicals to minimize immunoassay interference caused by heterophilic antibodies are commercially available. For example, a product called MAK33, which is an IgG1 monoclonal antibody to h-CK-MM, can be obtained from Boehringer Mannheim. The MAK33 plus product contains a combination of IgG1 and IgG1-Fab. polyMAK33 contains IgG1-Fab polymerized with IgG1, and the poly-MAC 2b/2a contains IgG2a-Fab polymerized with IgG2b. Bioreclamation Inc., East Meadow, N.Y., markets a second commercial source of biochemicals to neutralize heterophilic antibodies known as Immunoglobulin Inhibiting Reagent. This product is a preparation of immunoglobulins (IgG and IgM) from multiple species, mainly murine IgG2a, IgG2b, and IgG3 from Balb/c mice. In some embodiments the heterophilic antibody can be immunoextracted from the sample using methods known in the art, e.g., depleting the sample of the heterophilic antibody by binding the interfering antibody to protein A or protein G. In some embodiments, the heterophilic antibody can be neutralized using one or more heterophilic antibody blockers. Heterophilic blockers can be selected from the group consisting of anti-isotype heterophilic antibody blockers, anti-idiotype heterophilic antibody blockers, and anti-anti-idiotype heterophilic antibody blockers. In some embodiments, a combination of heterophilic antibody blockers can be used.

Label is added either with or following the addition of sample and washing. Protocols for binding antibodies and other immunolabels to proteins and other molecules are well-known in the art. If the label binding step is separate from that of capture binding, the time allowed for label binding can be important, e.g., in clinical applications or other time sensitive settings. In some embodiments, the time allowed for binding of the molecule of interest to the label, e.g., an antibody-dye, is less than about 12, 10, 8, 6, 4, 3, 2, or 1 hours, or less than about 60, 50, 40, 30, 25, 20, 15, 10, or 5 minutes. In some embodiments, the time allowed for binding of the molecule of interest to the label, e.g., an antibody-dye, is less than about 60 minutes. In some embodiments, the time allowed for binding of the molecule of interest to the label, e.g., an antibody-dye, is less than about 50 minutes. In some embodiments, the time allowed for binding of the molecule of interest to the label, e.g., an antibody-dye, is less than about 40 minutes. In some embodiments, the time allowed for binding of the molecule of interest to the label, e.g., an antibody-dye, is less than about 30 minutes. In some embodiments, the time allowed for binding of the molecule of interest to the label, e.g., an antibody-dye, is less than about 20 minutes. In some embodiments, the time allowed for binding of the molecule of interest to the label, e.g., an antibody-dye, is less than about 15 minutes. In some embodiments, the time allowed for binding of the molecule of interest to the label, e.g., an antibody-dye, is less than about 10 minutes. In some embodiments, the time allowed for binding of the molecule of interest to the label, e.g., an antibody-dye, is less than about 5 minutes. Excess label is removed by washing.

In some embodiments, the label is not eluted from the protein of interest. In other embodiments, the label is eluted from the protein of interest. Preferred elution buffers are effective in releasing the label without generating significant background. It is useful if the elution buffer is bacteriostatic. Elution buffers used in the invention can comprise a chaotrope, a buffer, an albumin to coat the surface of the microtiter plate, and a surfactant selected so as to produce a relatively low background. The chaotrope can comprise urea, a guanidinium compound, or other useful chaotropes. The buffer can comprise borate buffered saline, or other useful buffers. The protein carrier can comprise, e.g., an albumin, such as human, bovine, or fish albumin, an IgG, or other useful carriers. The surfactant can comprise an ionic or nonionic detergent including Tween 20, Triton X-100, sodium dodecyl sulfate (SDS), and others.

In another embodiment, the solid phase binding assay can be a competitive binding assay. One such method is as follows. First, a capture antibody immobilized on a binding surface is competitively bound by i) a molecule of interest, e.g., marker of a biological state, in a sample, and ii) a labeled analog of the molecule comprising a detectable label (the detection reagent). Second, the amount of the label using a single molecule analyzer is measured. Another such method is as follows. First, an antibody having a detectable label (the detection reagent) is competitively bound to i) a molecule of interest, e.g., marker of a biological state in a sample, and ii) an analog of the molecule that is immobilized on a binding surface (the capture reagent). Second, the amount of the label using a single molecule analyzer is measured. An "analog of a molecule" refers, herein, to a species that competes with a molecule for binding to a capture antibody. Examples of competitive immunoassays are disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

C. Detection of Molecule of Interest and Determination of Concentration

Following elution, the presence or absence of the label in the sample is detected using a single molecule detector. A sample can contain no label, a single label, or a plurality of labels. The number of labels corresponds to or is proportional to (if dilutions or fractions of samples are used) the number of molecules of the molecule of interest, e.g., a marker of a biological state captured during the capture step.

Any suitable single molecule detector capable of detecting the label used with the molecule of interest can be used. Suitable single molecule detectors are described herein. Typically the detector is part of a system that includes an automatic sampler for sampling prepared samples, and, optionally, a recovery system to recover samples.

In some embodiments, the sample is analyzed in a single molecule analyzer that uses a laser to illuminate an interrogation space containing a sample, a detector to detect radiation emitted from the interrogation space, and a scan motor and mirror attached to the motor to translate the interrogation space through the sample. In some embodiments, the single molecule analyzer further comprises a microscope objective lens that collects light emitted from the sample as the interrogation space is translated through the sample, e.g., a high numerical aperture microscope objective. In some embodiments, the laser and detector are configured in a confocal arrangement. In some embodiments, the laser is a continuous wave laser. In some embodiments, the detector is an avalanche photodiode detector. In some embodiments, the interrogation space is translated through the sample using a mirror attached to the scan motor. In some embodiments, the interrogation space is translated through the sample using multiple mirrors or a prism attached to the scan motor. In some embodiments, the invention provides an analyzer system that includes a sampling system capable of automatically sampling a plurality of samples with zero carryover between subsequently measured samples. In some embodiments, the interrogation space has a volume of more than about 1 $\mu m^3$, more than about 2 $\mu m^3$, more than about 3 $\mu m^3$, more than about 4 $\mu m^3$, more than about 5 $\mu m^3$, more than about 10 $\mu m^3$, more than about 15 $\mu m^3$, more than about 30 $\mu m^3$, more than about 50 $\mu m^3$, more than about 75 $\mu m^3$, more than about 100 $\mu m^3$, more than about 150 $\mu m^3$, more than about 200 $\mu m^3$, more than about 250 $\mu m^3$, more than about 300 $\mu m^3$, more than about 400 $\mu m^3$, more than about 500 $\mu m^3$, more than about 550 $\mu m^3$, more than about 600 $\mu m^3$, more than about 750 $\mu m^3$, more than about 1000 $\mu m^3$, more than about 2000 $\mu m^3$, more than about 4000 $\mu m^3$, more than about 6000 $\mu m^3$, more than about 8000 $\mu m^3$, more than about 10000 $\mu m^3$, more than about 12000 $\mu m^3$, more than about 13000 $\mu m^3$, more than about 14000 $\mu m^3$, more than about 15000 $\mu m^3$, more than about 20000 $\mu m^3$, more than about 30000 $\mu m^3$, more than about 40000 $\mu m^3$, or more than about 50000 $\mu m^3$. In some embodiments, the interrogation space is of a volume less than about 50000 $\mu m^3$, less than about 40000 $\mu m^3$, less than about 30000 $\mu m^3$, less than about 20000 $\mu m^3$, less than about 15000 $\mu m^3$, less than about 14000 $\mu m^3$, less than about 13000 $\mu m^3$, less than about 12000 $\mu m^3$, less than about 11000 $\mu m^3$, less than about 9500 $\mu m^3$, less than about 8000 $\mu m^3$, less than about 6500 $\mu m^3$, less than about 6000 $\mu m^3$, less than about 5000 $\mu m^3$, less than about 4000 $\mu m^3$, less than about 3000 $\mu m^3$, less than about 2500 $\mu m^3$, less than about 2000 $\mu m^3$, less than about 1500 $\mu m^3$, less than about 1000 $\mu m^3$, less than about 800 $\mu m^3$, less than about 600 $\mu m^3$, less than about 400 μm$^3$, less than about 200 μm$^3$, less than about 100 μm$^3$, less than about 75 μm$^3$, less than about 50 μm$^3$, less than about 25 μm$^3$, less than about 20 μm$^3$, less than about 15 μm$^3$, less than about 14 μm$^3$, less than about 13 μm$^3$, less than about 12 μm$^3$, less than about 11 μm$^3$, less than about 10 μm$^3$, less than about 5 μm$^3$, less than about 4 μm$^3$, less than about 3 μm$^3$, less than about 2 μm$^3$, or less than about 1 μm$^3$. In some embodiments, the volume of the interrogation space is between about 1 μm$^3$ and about 10000 μm$^3$. In some embodiments, the interrogation space is between about 1 μm$^3$ and about 1000 μm$^3$. In some embodiments, the interrogation space is between about 1 μm$^3$ and about 100 μm$^3$. In some embodiments, the interrogation space is between about 1 μm$^3$ and about 50 μm$^3$. In some embodiments, the interrogation space is between about 1 μm$^3$ and about 10 μm$^3$. In some embodiments, the interrogation space is between about 2 μm$^3$ and about 10 μm$^3$. In some embodiments, the interrogation space is between about 3 μm$^3$ and about 7 μm$^3$.

In some embodiments, the single molecule detector used in the methods of the invention uses a sample plate, a continuous wave laser directed toward a sample plate in which the sample is contained, a high numerical aperture microscope objective lens that collects light emitted from the sample as interrogation space is translated through the sample, wherein the lens has a numerical aperture of at least about 0.8, an avalanche photodiode detector to detect radiation emitted from the interrogation space, and a scan motor with a moveable mirror to translate the interrogation space through the sample wherein the interrogation space is between about 1 μm$^3$ and about 10000 μm$^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 1 μm$^3$ and about 1000 μm$^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 1 μm$^3$ and about 100 μm$^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 1 μm$^3$ and about 10 μm$^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 2 μm$^3$ and about 10 μm$^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 2 μm$^3$ and about 8 μm$^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 3 μm$^3$ and about 7 μm$^3$. In any of these embodiments, the analyzer can contain only one interrogation space.

In other embodiments, the single molecule detector used in the methods of the invention uses a sample plate, a continuous wave laser directed toward a sample plate in which the sample is contained, a high numerical aperture microscope objective lens that collects light emitted from the sample as interrogation space is translated through the sample, an avalanche photodiode detector to detect radiation emitted from the interrogation space, and a scan motor with a moveable mirror to translate the interrogation space through the sample wherein the interrogation space is between about 1 μm$^3$ and about 10000 μm$^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 1 μm$^3$ and about 1000 μm$^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 1 μm$^3$ and about 100 μm$^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 1 $\mu m^3$ and about 10 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 2 $\mu m^3$ and about 10 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 2 $\mu m^3$ and about 8 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 3 $\mu m^3$ and about 7 $\mu m^3$. In any of these embodiments, the analyzer can contain only one interrogation space.

In some embodiments, the single molecule detector is capable of determining a concentration for a molecule of interest in a sample wherein the sample can range in concentration over a range of at least about 100-fold, 1000-fold, 10,000-fold, 100,000-fold, 300,000-fold, 1,000,000-fold, 10,000,000-fold, or 30,000,000-fold.

In some embodiments, the methods of the invention use a single molecule detector capable detecting a difference of less than about 50%, 40%, 30%, 20%, 15%, or 10% in concentration of an analyte between a first sample and a second sample contained in a sample plate, wherein the volume of the first sample and the second sample introduced into the analyzer is less than about 100, 90, 80, 70, 60, 50, 40, 30, 20, 15, 10, 5, 4, 3, 2, or 1 $\mu l$, and wherein the analyte is present at a concentration of less than about 100, 90, 80, 70, 60, 50, 40, 30, 20, 15, 10, 5, 4, 3, 2, or 1 femtomolar. In some embodiments, the methods of the invention use a single molecule detector capable of detecting a difference of less than about 50% in concentration of an analyte between a first sample and a second sample introduced into the detector, wherein the volume of the first sample and the second sample introduced into the analyzer is less than about 100 $\mu l$, and wherein the analyte is present at a concentration of less than about 100 femtomolar. In some embodiments, the methods of the invention use a single molecule detector capable detecting a difference of less than about 40% in concentration of an analyte between a first sample and a second sample that are introduced into the detector, wherein the volume of the first sample and the second sample introduced into the analyzer is less than about 50 $\mu l$, and wherein the analyte is present at a concentration of less than about 50 femtomolar. In some embodiments, the methods of the invention use a single molecule detector capable detecting a difference of less than about 20% in concentration of an analyte between a first sample and a second sample that are introduced into the detector, wherein the volume of the first sample and the second sample introduced into the analyzer is less than about 20 $\mu l$, and wherein the analyte is present at a concentration of less than about 20 femtomolar. In some embodiments, the methods of the invention use a single molecule detector capable detecting a difference of less than about 20% in concentration of an analyte between a first sample and a second sample that are introduced into the detector, where the volume of the first sample and the second sample introduced into the analyzer is less than about 10 $\mu l$, and wherein the analyte is present at a concentration of less than about 10 femtomolar. In some embodiments, the methods of the invention use a single molecule detector capable detecting a difference of less than about 20% in concentration of an analyte between a first sample and a second sample that are introduced into the detector, wherein the volume of the first sample and the second sample introduced into the analyzer is less than about 5 $\mu l$, and wherein the analyte is present at a concentration of less than about 5 femtomolar.

A feature that contributes to the extremely high sensitivity of the instruments and methods of the invention is the method of detecting and counting labels, which, in some embodiments, are attached to single molecules to be detected or, more typically, correspond to a single molecule to be detected. Briefly, the sample contained in the sample plate is effectively divided into a series of detection events, by translating an interrogation space through the sample plate wherein EM radiation from a laser of an appropriate excitation wavelength for the fluorescent moiety used in the label for a predetermined period of time is directed to the wavelength, and photons emitted during that time are detected. Each predetermined period of time is a "bin." If the total number of photons detected in a given bin exceeds a predetermined threshold level, a detection event is registered for that bin, i.e., a label has been detected. If the total number of photons is not at the predetermined threshold level, no detection event is registered. In some embodiments, the processing sample concentration is dilute enough that, for a large percentage of detection events, the detection event represents only one label passing through the window, which corresponds to a single molecule of interest in the original sample. Accordingly, few detection events represent more than one label in a single bin. In some embodiments, further refinements are applied to allow greater concentrations of label in the processing sample to be detected accurately, i.e., concentrations at which the probability of two or more labels being detected as a single detection event is no longer insignificant.

Although other bin times can be used without departing from the scope of the present invention, in some embodiments the bin times are selected in the range of about 1 microsecond to about 5 ms. In some embodiments, the bin time is more than about 1, 2, 3, 4, 5, 6, 7, 8, 9, 10, 15, 20, 30, 40, 50, 60, 70, 80, 90, 100, 200, 250, 300, 400, 500, 600, 700, 750, 800, 900, 1000, 2000, 3000, 4000, or 5000 microseconds. In some embodiments, the bin time is less than about 2, 3, 4, 5, 6, 7, 8, 9, 10, 15, 20, 30, 40, 50, 60, 70, 80, 90, 100, 200, 250, 300, 400, 500, 600, 700, 750, 800, 900, 1000, 2000, 3000, 4000, or 5000 microseconds. In some embodiments, the bin time is about 1 to 1000 microseconds. In some embodiments, the bin time is about 1 to 750 microseconds. In some embodiments, the bin time is about 1 to 500 microseconds. In some embodiments, the bin time is about 1 to 250 microseconds. In some embodiments, the bin time is about 1 to 100 microseconds. In some embodiments, the bin time is about 1 to 50 microseconds. In some embodiments, the bin time is about 1 to 40 microseconds. In some embodiments, the bin time is about 1 to 30 microseconds. In some embodiments, the bin time is about 1 to 25 microseconds. In some embodiments, the bin time is about 1 to 20 microseconds. In some embodiments, the bin time is about 1 to 10 microseconds. In some embodiments, the bin time is about 1 to 7.5 microseconds. In some embodiments, the bin time is about 1 to 5 microseconds. In some embodiments, the bin time is about 5 to 500 microseconds. In some embodiments, the bin time is about 5 to 250 microseconds. In some embodiments, the bin time is about 5 to 100 microseconds. In some embodiments, the bin time is about 5 to 50 microseconds. In some embodiments, the bin time is about 5 to 20 microseconds. In some embodiments, the bin time is about 5 to 10 microseconds. In some embodiments, the bin time is about 10 to 500 microseconds. In some embodiments, the bin time is about 10 to 250 microseconds. In some embodiments, the bin time is about 10 to 100 microseconds. In some embodiments, the bin time is about 10 to 50 microseconds. In some embodiments, the bin time is about 10 to 30 microseconds. In some embodiments, the bin time is about 10 to 20 microseconds. In some embodiments, the bin time is about 1 microsecond. In some embodiments, the bin time is about 2 microseconds. In some embodiments, the bin time is about 3 microseconds. In some embodiments, the bin time is about 4 microseconds. In some embodiments, the bin time is about 5 microseconds. In some embodiments, the bin time is about 6 microseconds. In some embodiments, the bin time is about 7 microseconds. In some embodiments, the bin time is about 8 microseconds. In some embodiments, the bin time is about 9 microseconds. In some embodiments, the bin time is about 10 microseconds. In some embodiments, the bin time is about 11 microseconds. In some embodiments, the bin time is about 12 microseconds. In some embodiments, the bin time is about 13 microseconds. In some embodiments, the bin time is about 14 microseconds. In some embodiments, the bin time is about 5 microseconds. In some embodiments, the bin time is about 15 microseconds. In some embodiments, the bin time is about 16 microseconds. In some embodiments, the bin time is about 17 microseconds. In some embodiments, the bin time is about 18 microseconds. In some embodiments, the bin time is about 19 microseconds. In some embodiments, the bin time is about 20 microseconds. In some embodiments, the bin time is about 25 microseconds. In some embodiments, the bin time is about 30 microseconds. In some embodiments, the bin time is about 40 microseconds. In some embodiments, the bin time is about 50 microseconds. In some embodiments, the bin time is about 100 microseconds. In some embodiments, the bin time is about 250 microseconds. In some embodiments, the bin time is about 500 microseconds. In some embodiments, the bin time is about 750 microseconds. In some embodiments, the bin time is about 1000 microseconds.

In some embodiments, determining the concentration of a particle-label complex in a sample comprises determining the background noise level. In some embodiments, the background noise level is determined from the mean noise level, or the root-mean-square noise. In other embodiments, a typical noise value or a statistical value is chosen. Often, the noise is expected to follow a Poisson distribution.

As the interrogation space is translated through the sample, the laser beam directed to the interrogation space generates a burst of photons when a label is encountered. The photons emitted by the label are discriminated from background light or background noise emission by considering only the bursts of photons with energy above a predetermined threshold energy level, thereby accounting for the amount of background noise present in the sample. Background noise typically comprises low frequency emission produced, e.g., by the intrinsic fluorescence of non-labeled particles that are present in the sample, the buffer or diluent used in preparing the sample for analysis, Raman scattering and electronic noise. In some embodiments, the value assigned to the background noise is calculated as the average background signal noise detected in a plurality of bins, which are measurements of photon signals that are detected in an interrogation space during a predetermined length of time. In some embodiments, background noise is calculated for each sample as a number specific to that sample.

Given the value for the background noise, a threshold energy level can be assigned. As discussed above, the threshold value is determined to discriminate true signals resulting from the fluorescence of a label from the background noise. A threshold value can be chosen such that the number of false positive signals from random noise is minimized while the number of true signals which are rejected is also minimized. Methods for choosing a threshold value include determining a fixed value above the noise level and calculating a threshold value based on the distribution of the noise signal. In one embodiment, the threshold is set at a fixed number of standard deviations above the background level. Assuming a Poisson distribution of the noise, using this method one can estimate the number of false positive signals over the time course of the experiment. In some embodiments, the threshold level is calculated as a value of four standard deviations ($\sigma$) above the background noise. For example, given an average background noise level of 200 photons, the analyzer system establishes a threshold level of $4\sqrt{200}$ above the average background/noise level of 200 photons to be 256 photons. Thus, in some embodiments, determining the concentration of a label in a sample includes establishing the threshold level above which photon signals represent the presence of a label. Conversely, the absence of photon signals with an energy level greater than the threshold level indicate the absence of a label.

Many bin measurements are taken to determine the concentration of a sample, and the absence or presence of a label is ascertained for each bin measurement. Typically, 60,000 measurements or more can be made in 1 min. 60,000 measurements are made in 1 min when the bin size is 1 ms. For smaller bin sizes the number of measurements is correspondingly larger, e.g., 6,000,000 measurements per minute equates to a bin size of 10 microseconds. Because so many measurements are taken, no single measurement is crucial, thus providing for a high margin of error. Bins that are determined not to contain a label ("no" bins) are discounted and only the measurements made in the bins that are determined to contain label ("yes" bins) are accounted in determining the concentration of the label in the processing sample. Discounting measurements made in the "no" bins or bins that are devoid of label increases the signal to noise ratio and the accuracy of the measurements. Thus, in some embodiments, determining the concentration of a label in a sample comprises detecting the bin measurements that reflect the presence of a label.

The signal to noise ratio or the sensitivity of the analyzer system can be increased by minimizing the time that background noise is detected during a bin measurement in which a particle-label complex is detected. For example, consider a bin measurement lasting 1 millisecond during which one particle-label complex is detected as it passes across an interrogation space in 250 microseconds. Under these conditions, 750 microseconds of the 1 millisecond are spent detecting background noise emission. The signal to noise ratio can be improved by decreasing the bin time. In some embodiments, the bin time is 1 millisecond. In other embodiments, the bin time is 750 microseconds, 500 microseconds, 250 microseconds, 100 microseconds, 50 microseconds, 25 microseconds or 10 microseconds. Other bin times are as described herein.

Other factors that affect measurements are the brightness or dimness of the fluorescent moiety, size of the aperture image or lateral extent of the laser beam, the rate at which the interrogation space is translated through the sample, and the power of the laser. Various combinations of the relevant factors that allow for detection of label will be apparent to those of skill in the art. In some embodiments, the bin time is adjusted without changing the scan speed. It will be appreciated by those of skill in the art that as bin time decreases, laser power output directed at the interrogation space must increase to maintain a constant total energy applied to the interrogation space during the bin time. For example, if bin time is decreased from 1000 microseconds to 250 microseconds, as a first approximation, laser power output must be increased approximately four-fold. These settings allow for the detection of the same number of photons in a 250 microseconds as the number of photons counted during the 1000 microseconds given the previous settings, and allow for faster analysis of sample with lower backgrounds and greater sensitivity. In addition, the speed at which the interrogation space is translated through the sample can be adjusted in order to speed processing of sample. These numbers are merely exemplary, and the skilled practitioner can adjust the parameters as necessary to achieve the desired result.

In some embodiments, the interrogation space is smaller than the volume of sample when, for example, the interrogation space is defined by the size of the spot illuminated by the laser beam. In some embodiments, the interrogation space can be defined by adjusting the apertures 182 (FIGS. 1A & 1B) of the analyzer and reducing the illuminated volume that is imaged by the objective lens to the detector. In embodiments wherein the interrogation space is defined to be smaller than the cross-sectional area of the sample, the concentration of the label can be determined by interpolation of the signal emitted by the complex from a standard curve that is generated using one or more samples of known standard concentrations. In other embodiments, the concentration of the label can be determined by comparing the measured particles to an internal label standard. In embodiments wherein a diluted sample is analyzed, the dilution factor is accounted for when calculating the concentration of the molecule of interest in the starting sample.

To determine the concentration of labels in the processing sample, the total number of labels contained in the "yes" bins is determined relative to the sample volume represented by the total number of bins. Thus, in one embodiment, determining the concentration of a label in a processing sample comprises determining the total number of labels detected "yes" and relating the total number of detected labels to the total sample volume that was analyzed. The total sample volume that is analyzed is the sample volume through which the interrogation space is translated in a specified time interval. Alternatively, the concentration of the label complex in a sample is determined by interpolation of the signal emitted by the label in a number of bins from a standard curve that is generated by determining the signal emitted by labels in the same number of bins by standard samples containing known concentrations of the label.

In some embodiments, the number of individual labels detected in a bin is related to the relative concentration of the particle in the processing sample. At relatively low concentrations, e.g., at concentrations below about $10^{-16}$ M, the number of labels is proportional to the photon signal detected in a bin. Thus, at low concentrations of label the photon signal is provided as a digital signal. At relatively higher concentrations, for example at concentrations greater than about $10^{-16}$ M, the proportionality of photon signal to a label is lost as the likelihood of two or more labels crossing the interrogation space at about the same time and being counted as one becomes significant. Thus, in some embodiments, individual particles in a sample of a concentration greater than about $10^{-16}$ M are resolved by decreasing the length of time of the bin measurement.

In other embodiments, the total photon signal that is emitted by a plurality of particles that are present in any one bin is detected. These embodiments allow for single molecule detectors of the invention wherein the dynamic range is at least 3, 3.5, 4, 4.5, 5.5, 6, 6.5, 7, 7.5, 8, or more than 8 logs.

"Dynamic range," as that term is used herein, refers to the range of sample concentrations that can be quantitated by the instrument without need for dilution or other treatment to alter the concentration of successive samples of differing concentrations, where concentrations are determined with accuracy appropriate for the intended use. For example, if a microtiter plate contains a sample of 1 femtomolar concentration for an analyte of interest in one well, a sample of 10,000 femtomolar concentration for an analyte of interest in another well, and a sample of 100 femtomolar concentration for the analyte in a third well, an instrument with a dynamic range of at least 4 logs and a lower limit of quantitation of 1 femtomolar can accurately quantitate the concentration of all the samples without further treatment to adjust concentration, e.g., dilution. Accuracy can be determined by standard methods, e.g., measuring a series of standards with concentrations spanning the dynamic range and constructing a standard curve. Standard measures of fit of the resulting standard curve can be used as a measure of accuracy, e.g., an $r^2$ greater than about 0.7, 0.75, 0.8, 0.85, 0.9, 0.91, 0.92, 0.93, 0.94, 0.95, 0.96, 0.97, 0.98, or 0.99.

Dynamic range can be increased by altering how data from the detector is analyzed, and perhaps using an attenuator between the detector and the interrogation space. At the low end of the range, the processing sample is sufficiently dilute that each detection event, i.e., each burst of photons above a threshold level in a bin (the "event photons"), likely represents only one label. Under these conditions, the data is analyzed to count detection events as single molecules so that each bin is analyzed as a simple "yes" or "no" for the presence of label, as described above. For a more concentrated processing sample, where the likelihood of two or more labels occupying a single bin becomes significant, the number of event photons in a significant number of bins is substantially greater than the number expected for a single label. For example, the number of event photons in a significant number of bins corresponds to two-fold, three-fold, or more than the number of event photons expected for a single label. For these samples, the instrument changes its method of data analysis to integrate the total number of event photons for the bins of the processing sample. This total is proportional to the total number of labels in all the bins. For an even more concentrated processing sample, where many labels are present in most bins, background noise becomes an insignificant portion of the total signal from each bin, and the instrument changes its method of data analysis to count total photons per bin (including background). An even further increase in dynamic range can be achieved by the use of an attenuator between the sample plate and the detector, when concentrations are such that the intensity of light reaching the detector would otherwise exceed the capacity of the detector for accurately counting photons, i.e., saturate the detector.

The instrument can include a data analysis system that receives input from the detector and determines the appropriate analysis method for the sample being run, and outputs values based on such analysis. The data analysis system can further output instructions to use or not use an attenuator, if an attenuator is included in the instrument.

By utilizing such methods, the dynamic range of the instrument can be dramatically increased. In some embodiments, the instrument is capable of measuring concentrations of samples over a dynamic range of more than about 1000 (3 log), 10,000 (4 log), 100,000 (5 log), 350,000 (5.5 log), 1,000,000 (6 log), 3,500,000 (6.5 log), 10,000,000 (7 log), 35,000,000 (7.5 log), or 100,000,000 (8 log). In some embodiments, the instrument is capable of measuring concentrations of samples over a dynamic range of more than about 100,000 (5 log). In some embodiments, the instrument is capable of measuring concentrations of samples over a dynamic range of more than about 1,000,000 (6 log). In some embodiments, the instrument is capable of measuring concentrations of samples over a dynamic range of more than about 10,000,000 (7 log). In some embodiments, the instrument is capable of measuring the concentrations of samples over a dynamic range of from about 1 to 10 femtomolar to at least about 1000, 10,000, 100,000, 350,000, 1,000,000, 3,500,000, 10,000,000, or 35,000,000 femtomolar. In some embodiments, the instrument is capable of measuring the concentrations of samples over a dynamic range of from about 1 to 10 femtomolar to at least about 10,000 femtomolar. In some embodiments, the instrument is capable of measuring the concentrations of samples over a dynamic range of from about 1 to 10 femtomolar to at least about 100,000 femtomolar. In some embodiments, the instrument is capable of measuring the concentrations of samples over a dynamic range of from about 1 to 10 femtomolar to at least about 1,000,000 femtomolar. In some embodiments, the instrument is capable of measuring the concentrations of samples over a dynamic range of from about 1 to 10 femtomolar to at least about 10,000,000.

In some embodiments, an analyzer or analyzer system of the invention is capable of detecting an analyte, e.g., a biomarker, at a limit of detection of less than about 1 nanomolar, or 1 picomolar, or 1 femtomolar, or 1 attomolar, or 1 zeptomolar. In some embodiments, the analyzer or analyzer system is capable of detecting a change in concentration of the analyte, or of multiple analytes, e.g., a biomarker or biomarkers, from one sample to another sample of less than about 0.1%, 1%, 2%, 5%, 10%, 20%, 30%, 40%, 50%, 60%, or 80% when the biomarker is present at a concentration of less than about 1 nanomolar, or 1 picomolar, or 1 femtomolar, or 1 attomolar, or 1 zeptomolar, in the samples, and when the size of each of the sample is less than about 100, 50, 40, 30, 20, 10, 5, 2, 1, 0.1, 0.01, 0.001, or 0.0001 µl. In some embodiments, the analyzer or analyzer system is capable of detecting a change in concentration of the analyte from a first sample to a second sample of less than about 20%, when the analyte is present at a concentration of less than about 1 picomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 100 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 50 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 5 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 5 femtomolar, and when the size of each of the samples is less than about 5 µl. In some embodiments, the analyzer or analyzer system is capable of detecting a change in concentration of the analyte from a first sample to a second sample of less than about 20%, when the analyte is present at a concentration of less than about 1 femtomolar, and when the size of each of the samples is less than about 5 µl.

VI. Sample Carryover

Carryover is undesirable in diagnostics. The detection of a molecule of interest in one sample cannot compromise the accuracy of the detection of a molecule of interest in a subsequent sample being tested. The single molecule analyzer described herein is capable of detecting the presence or absence of a single molecule in one sample followed by the detection of the presence or absence of a single molecule in a subsequent sample with zero carryover between samples. The invention described herein provides for an instrument capable of sequentially detecting the presence or absence of a single molecule of a particular type in a first sample, and detecting the presence or absence of a single molecule of the type in a second sample, wherein the instrument is adapted and configured so that there is no carryover between the first and the second sample. Further provided herein is a method of sequentially detecting the presence or absence of a single molecule of a particular type in a first sample, and detecting the presence or absence of a single molecule of the type in a second sample, wherein there is no carryover between the first and the second sample.

In some embodiments, multiple samples are run on the same sample plate. In some embodiments, the samples are tested for the same type of single molecule of interest. In some embodiments, the type of single molecule tested for in the first sample is not the same type of molecule tested for in the second sample. This would be the case when running, e.g., a panel where the original sample is divided into multiple samples, each of which is tested for a different type of single molecule of interest.

In some embodiments, the sample plate contains one sample to be tested. In some embodiments, the sample plate contains two samples to be tested. In some embodiments, multiple samples can be tested on the same sample plate. In theory, tens, to hundreds, to thousands, or more than thousands of samples can be run sequentially with zero carryover between any two samples tested sequentially. The system is limited to the number of samples only by the constraints of the sample plate.

Creating a system with zero carryover is simple for systems in which the container or containers for containing the samples being tested are disposable. In such systems, as long as the detecting means does not come in contact with the sample, there is no chance of carryover with a disposable container. Disposable containers include items such as cuvettes and capillary tubes. The invention provided herein permits the testing of sequential samples that are contained within disposable and non-disposable containers. The invention discloses an instrumentation configuration wherein carryover between samples is not possible.

VII. Methods of Use of Single Molecule Analyzer

Further provided herein is a method for detecting the presence or absence of a single molecule in a sample comprising: (a) directing electromagnetic radiation from an electromagnetic radiation source to an interrogation space in the sample; (b) detecting the presence or absence of a first single molecule in the interrogation space located at a first position in the sample; (c) translating the interrogation space through the sample to a subsequent position in the sample; (d) detecting the presence or absence of a subsequent single molecule in the subsequent position in the sample; and (e) repeating steps (c) and (d) as required to detect the presence or absence of a single molecule in more than one position of the sample. In some embodiments, the interrogation space has a volume of more than about 1 $\mu m^3$, more than about 2 $\mu m^3$, more than about 3 $\mu m^3$, more than about 4 $\mu m^3$, more than about 5 $\mu m^3$, more than about 10 $\mu m^3$, more than about 15 $\mu m^3$, more than about 30 $\mu m^3$, more than about 50 $\mu m^3$, more than about 75 $\mu m^3$, more than about 100 $\mu m^3$, more than about 150 $\mu m^3$, more than about 200 $\mu m^3$, more than about 250 $\mu m^3$, more than about 300 $\mu m^3$, more than about 400 $\mu m^3$, more than about 500 $\mu m^3$, more than about 550 $\mu m^3$, more than about 600 $\mu m^3$, more than about 750 $\mu m^3$, more than about 1000 $\mu m^3$, more than about 2000 $\mu m^3$, more than about 4000 $\mu m^3$, more than about 6000 $\mu m^3$, more than about 8000 $\mu m^3$, more than about 10000 $\mu m^3$, more than about 12000 $\mu m^3$, more than about 13000 $\mu m^3$, more than about 14000 $\mu m^3$, more than about 15000 $\mu m^3$, more than about 20000 $\mu m^3$, more than about 30000 $\mu m^3$, more than about 40000 $\mu m^3$, or more than about 50000 $\mu m^3$. In some embodiments, the interrogation space is of a volume less than about 50000 $\mu m^3$, less than about 40000 $\mu m^3$, less than about 30000 $\mu m^3$, less than about 20000 $\mu m^3$, less than about 15000 $\mu m^3$, less than about 14000 $\mu m^3$, less than about 13000 $\mu m^3$, less than about 12000 $\mu m^3$, less than about 11000 $\mu m^3$, less than about 9500 $\mu m^3$, less than about 8000 $\mu m^3$, less than about 6500 $\mu m^3$, less than about 6000 $\mu m^3$, less than about 5000 $\mu m^3$, less than about 4000 $\mu m^3$, less than about 3000 $\mu m^3$, less than about 2500 $\mu m^3$, less than about 2000 $\mu m^3$, less than about 1500 $\mu m^3$, less than about 1000 $\mu m^3$, less than about 800 $\mu m^3$, less than about 600 $\mu m^3$, less than about 400 $\mu m^3$, less than about 200 $\mu m^3$, less than about 100 $\mu m^3$, less than about 75 $\mu m^3$, less than about 50 $\mu m^3$, less than about 25 $\mu m^3$, less than about 20 $\mu m^3$, less than about 15 $\mu m^3$, less than about 14 $\mu m^3$, less than about 13 $\mu m^3$, less than about 12 $\mu m^3$, less than about 11 $\mu m^3$, less than about 10 $\mu m^3$, less than about 5 $\mu m^3$, less than about 4 $\mu m^3$, less than about 3 $\mu m^3$, less than about 2 $\mu m^3$, or less than about 1 $\mu m^3$. In some embodiments, the volume of the interrogation space is between about 1 $\mu m^3$ and about 10000 $\mu m^3$. In some embodiments the interrogation space is between about 1 $\mu m^3$ and about 1000 $\mu m^3$. In some embodiments the interrogation space is between about 1 $\mu m^3$ and about 100 $\mu m^3$. In some embodiments the interrogation space is between about 1 $\mu m^3$ and about 50 $\mu m^3$. In some embodiments the interrogation space is between about 1 $\mu m^3$ and about 10 $\mu m^3$. In some embodiments, the interrogation space is between about 2 $\mu m^3$ and about 10 $\mu m^3$. In some embodiments, the interrogation space is between about 3 $\mu m^3$ and about 7 $\mu m^3$.

Further provided herein is a method for detecting the presence or absence of a single molecule wherein the interrogation space is translated in a non-linear path. In a further embodiment, the non-linear path comprises a substantially circular path. In another embodiment, the non-linear path comprises a helical pattern. The invention provides for a method of detecting the presence or absence of a single molecule in an interrogation space wherein the interrogation space is translated through the sample. In some embodiments, the method provides for the sample to remain substantially stationary relative to the instrumentation. In some embodiments, the method provides that the sample is translated with respect to the instrumentation. In some embodiments, both the sample and the electromagnetic radiation are translated with respect to one another. In an embodiment where the sample is translated with respect to the instrumentation, the sample can remain stationary within its container, e.g., a microwell. While single molecules can diffuse in and out of an interrogation space or a series of interrogations spaces, the medium in which the single molecules are present remains stationary. Therefore, this system allows for single molecule detection without the need for flowing fluid.

EXAMPLES

Example 1

Molecule Detection and Standard Curve Generation

Figure 3:
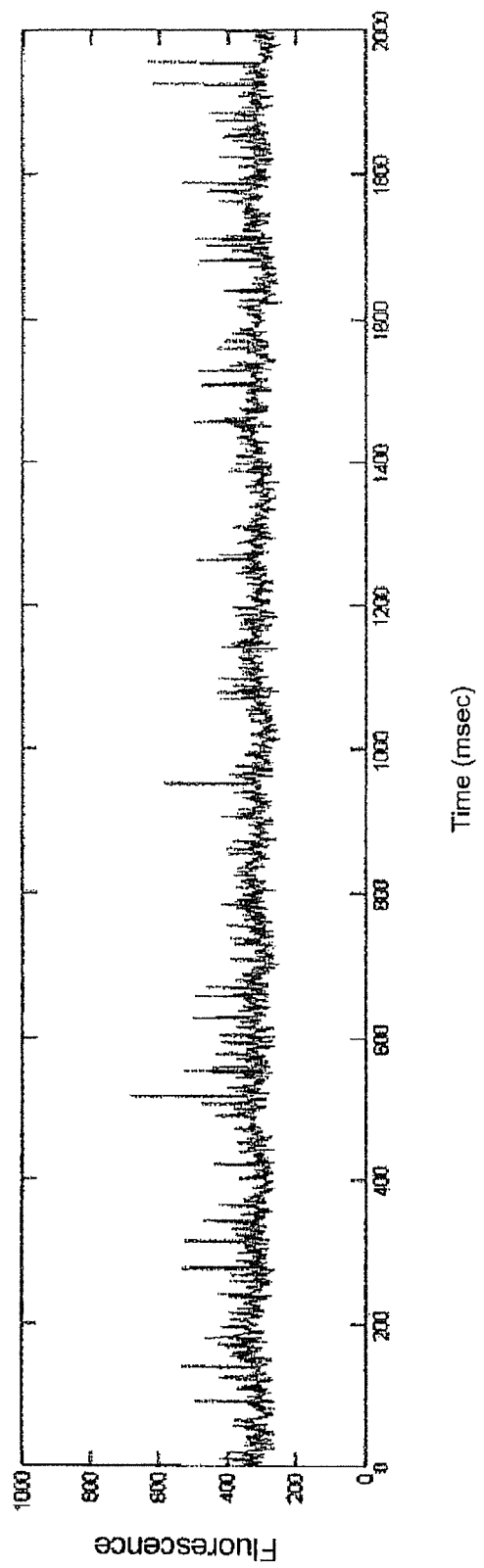
FIG. 3 shows detection event data generated using a scanning single molecule analyzer.

FIG. 3 illustrates the detection of single molecules using a device of the present invention. The plot shows representative data for fluorescence detected on the vertical axis versus time (msec) on the horizontal axis. The spikes shown in the graph were generated when the scanning single molecule analyzer encountered one or more labeled molecules within the interrogation space. The total fluorescent signal comprises the sum of individual detection events (DE), wherein an event comprises fluorescence detected above the background noise. The count of all the events during the recording can be referred to as the "DE value." At low concentrations, the DE value corresponds to the number of detected molecules. At higher concentrations wherein two or more molecules can pass through the detection spot at once, the number of molecules detected can be higher than the DE count.

Figure 4:
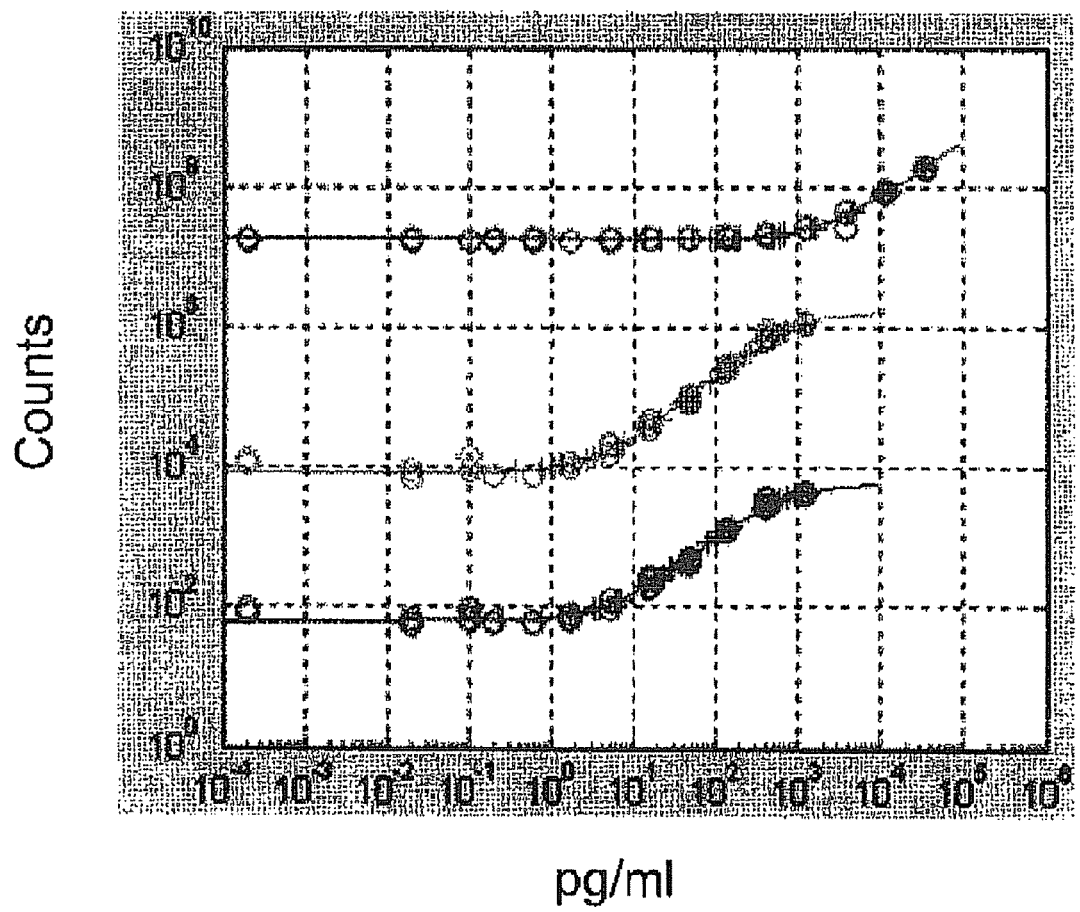
FIG. 4 shows a standard curve generated with a scanning single molecule analyzer by detecting a sample over a range of known concentrations.

FIG. 4 illustrates a standard curve generated with a scanning single molecule analyzer. To generate the curve, samples were prepared with known concentrations and measured using a device of the present invention. Three curves are shown in the plot. The upper curve corresponds to the total photons (TP) detected. The middle curve corresponds to the event photons (EP) detected. The lower curve corresponds to detected events (DE). The plot shows the values for each of these measures ("Counts") on the vertical axis versus the known sample concentration (pg/ml) on the horizontal axis. The plotted circles are the counts plotted at their known concentrations. The solid curve is a least squares fit of the data to a four parameter logistics curve. The "+" symbols are the counts plotted at their interpolated concentrations instead of their known concentrations. The "+" symbols indicate how well the fitted curve passes through the actual data. This data demonstrates that as the concentration of the sample is varied, there is a clear change in the number of molecules detected.

Example 2

Sandwich Assays for Biomarkers: Cardiac Troponin I (ctnI)

The Assay: The purpose of this assay is to detect the presence of cardiac Troponin I (cTNI) in human serum. The assay format comprises a two-step sandwich immunoassay using a mouse monoclonal capture antibody and a goat polyclonal detection antibody. Ten microliters of sample are required. The working range of the assay is 0-900 pg/ml with a typical analytical limit of detection of 1 to 3 pg/ml. The assay requires about 4 h of bench time to complete.

Materials: The following materials are used in the procedure described below. The assay plate comprises a clear 384 well NUNC™ Maxisorp, product 464718. The plate is passively coated overnight at room temperature with a monoclonal antibody comprising BiosPacific A34440228P Lot #A0316 (5 µg/ml in 0.05 M sodium carbonate pH 9.6) and blocked with 5% sucrose, 1% BSA in phosphate buffered saline (PBS), and stored at 4° C. For the standard curve, Human cardiac Troponin I (BiosPacific Cat #334000352) is used. The diluent for the standard concentrations is human serum immuno-depleted of endogenous cTNI, aliquoted and stored at −20° C. Standards are diluted in a 96 well, conical, polypropylene plate (NUNC™ product #249944). The following buffers and solutions are used: (a) assay buffer (borate buffer saline (BBS) with 1% BSA and 0.1% Triton X-100); (b) passive blocking solution (assay buffer containing 2 mg/ml mouse IgG (Equitech Bio), 2 mg/ml goat IgG (Equitech Bio), and 2 mg/ml MAK33 IgG1 Poly (Roche #11 939 661)); (c) detection antibody (goat polyclonal antibody affinity purified to Peptide 3 (BiosPacific G-129-C), labeled with fluorescent dye Alexa Fluor 647, and stored at 4° C.); (d) detection antibody diluent (50% assay buffer, 50% passive blocking solution); (e) wash buffer (borate buffer saline Triton buffer (BBST) (1.0 M borate, 15.0 M sodium chloride, 10% Triton X-100, pH 8.3)); (f) elution buffer (BBS with 4M urea, 0.02% Triton X-100 and 0.001% BSA); and (g) coupling buffer (0.1 M $NaHCO_3$).

Preparation of Alexa Fluor 647 Labeled Antibodies: The detection antibody G-129-C is prepared by conjugation to Alexa Fluor 647. 100 µg of G-129-C is dissolved in 400 µl of the coupling buffer. The antibody solution is concentrated to 50 µl by transferring the solution into YM-30 filter and subjecting the solution and filter to centrifugation. The YM-30 filter and antibody are washed three times by adding 400 µl of the coupling buffer. The antibody is recovered by adding 50 µl of coupling buffer to the filter, inverting the filter, and centrifuging for 1 min at 5,000×g. The resulting antibody solution has a concentration of about 1-2 µg/µl. Alexa Fluor 647 NHS ester stock solution is made by reconstituted one vial of Alexa Fluor 647 in 20 µl DMSO. This solution can be stored at −20° C. for up to 1 month. 3 µl of Alexa Fluor 647 stock solution is mixed with the antibody solution in the dark for 1 h. Thereafter, 7.5 µl 1 M tris is added to the antibody Alexa Fluor 647 solution and mixed. The solution is ultrafiltered with YM-30 to remove low molecular weight components. The volume of the retentate, which contains the antibody conjugated to Alexa Fluor 647, is adjusted to 200-400 µl by adding PBS. 3 µl 10% $NaN_3$ is added to the solution. The resulting solution is transferred to an Ultrafree 0.22 centrifugal unit and centrifuged for 2 min at 12,000×g. The filtrate containing the conjugated antibody is collected and used in the assays.

Procedure: Standards are prepared (0-900 pg/ml) by serial dilutions of the stock of cTnI standard into standard diluent to achieve a range of cTnI concentrations of between 1.2 pg/ml-4.3 µg/ml. 10 µl passive blocking solution and 10 µl of either the standard or a sample are added to each well of the appropriate plate. Standards are run in quadruplicate. The plate is sealed, preferably with a low-fluorescence sealing film, centrifuged for 1 min at 3000 RPM, and incubated for 2 h at 25° C. with shaking. The plate is washed five times, and centrifuged until the rotor reaches 3000 RPM in an inverted position over a paper towel. A 1 nM working dilution of detection antibody is prepared, and 20 µl detection antibody are added to each well. The plate is sealed and centrifuged, and the assay is incubated for 1 h at 25° C. with shaking. 30 µl elution buffer are added per well, the plate is sealed and the assay is incubated for ½ h at 25° C. The plate can be analyzed immediately or can be stored for up to 48 h at 4° C. prior to analysis.

For analysis, 20 µl per well are acquired at 40 µl/minute, and 5 µl are analyzed at a 16.7 mm/sec scan rate. The data is analyzed based on a threshold of 4 standard deviations ($\sigma$). The raw signal is plotted versus concentration of the standards. A linear fit is performed for the low concentration range, and a non-linear fit is performed for the full standard curve. The limit of detection (LOD) is calculated as LOD=(3×$\sigma$ of zero samples)/slope of linear fit. The concentrations of the samples are determined from the linear or non-linear equation appropriate for the sample signal.

The sample plate is then loaded into the scanning single molecule analyzer. Individually-labeled antibodies are measured by translating the interrogation space through the sample at a speed such that the emission from only one fluorescent label is detected in a defined space following laser excitation. The total fluorescent signal is a sum of the individual detection events as described above.

Example 3

Sandwich Bead-Based Assays for TnI

The assays described above uses a microtiter plate format where the plastic surface is used to immobilize target molecules. The single particle analyzer system is also compatible with assays performed in solution using microparticles or beads to separate bound and unbound entities.

Materials: MyOne Streptavidin C1 microparticles (MPs) are obtained from Dynal (650.01-03, 10 mg/ml stock). Buffers used include: (a) 10× borate buffer saline Triton Buffer (BBST) (1.0 M borate, 15.0 M sodium chloride, 10% Triton X-100, pH 8.3); (b) assay buffer (2 mg/ml normal goat IgG, 2 mg/ml normal mouse IgG, and 0.2 mg/ml MAB-33-IgG-Polymer in 0.1 M Tris (pH 8.1), 0.025 M EDTA, 0.15 M NaCl, 0.1% BSA, 0.1% Triton X-100, and 0.1% $NaN_3$, stored at 4° C.); and (c) elution buffer (BBS with 4 M urea, 0.02% Triton X-100, and 0.001% BSA, stored at 2-8° C.). Antibodies used in the sandwich bead-based assay include: (a) Bio-Ab (A34650228P (BiosPacific) with 1-2 biotins per IgG); and (b) Det-Ab (G-129-C (BiosPacific) conjugated to Alexa Fluor 647, 2-4 fluors per IgG). The standard is recombinant human cardiac troponin I (BiosPacific, cat #J34120352). The calibrator diluent is 30 mg/ml BSA in tris buffered saline (TBS) with EDTA.

Microparticles Coating: 100 µl of the MPs stock solution is placed in an Eppendorf tube. The MPs are washed three times with 100 µl BBST wash buffer by applying a magnet, removing the supernatant, removing the magnet, and resuspending in wash buffer. After washing, the MPs are resuspended in 100 µl of assay buffer and 15 µg of Bio-Ab are added. The mixture is incubated for 1 h at room temperature with constant mixing. The MPs are washed five times with 1 ml wash buffer as described above. After the washes the MPs are resuspended in 15 ml of assay buffer (or 100 µl to store at 4° C.).

Preparation of Standard and Samples: The standard is diluted with calibrator diluent to prepare a proper standard curve, typically ranging from 200 pg/ml to 0.1 pg/ml. Frozen serum and plasma samples are centrifuged 10 min at room temperature at 13,000 rpm. Clarified serum or plasma is removed carefully to avoid pellets or floaters and transferred to fresh tubes. 50 µl of each standard or sample is pipetted into appropriate wells.

Capture Target: After resuspension to 15 ml in assay buffer comprising 400 mM NaCl, 150 µl of the MPs are added to each well. The mixture is incubated on a Boekel Jitterbug Microplate Incubator Shaker at room temperature for 1 h.

Washes and Detection: The plate is placed on a magnet and the supernatant is removed after allowing the magnets to capture the MPs. After removing the plate from the magnet, 250 µl of wash buffer are added. Again, the plate is placed on a magnet and the supernatant is removed after allowing the magnets to capture the MPs. 20 µl Det-Ab are added per well. If necessary, Det-Ab to 500 ng/ml is first diluted in assay buffer comprising 400 mM NaCl. The mixture is incubated on a Boekel Jitterbug Microplate Incubator Shaker at room temperature for 30 min. The plate is washed as described three times with wash buffer. After washing, 250 µl of wash buffer are added and the samples are transferred into a new 96-well plate. The wash step is repeated twice. 20 µl of elution buffer are then added and the mixture is incubated on Boekel Jitterbug Microplate Incubator Shaker at room temperature for 30 min.

Filter MPs and Transfer to 384-well Plate: The standard and samples are transferred into a 384-well filter plate placed on top of a 384-well assay plate. The plate is centrifuged at room temperature at 3000 rpm. The filter plate is removed and the appropriate calibrators are added. The plate is covered and is ready for scanning single molecule detector.

Scanning Single Molecule Detector: A sample in a sample well is scanned using an electromagnetic radiation source. The interrogation space is translated through the sample. The sample is scanned at a speed that is sufficiently slow so that individually-labeled antibodies are measured during the sample scan. This is achieved by setting the interrogation space such that the emission of only one fluorescent molecule, if present, is detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of detected events/sample. The limit of detection the cTnI assay of the invention is determined by the mean plus 3σ method (see above).

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. An apparatus for detecting an analyte in a sample, comprising:
   (a) an electromagnetic radiation source;
   (b) a system that directs electromagnetic radiation from the electromagnetic radiation source to an interrogation space in the sample;
   (c) a translating system for translating the interrogation space through at least a portion of the sample, thereby forming a moveable interrogation space; and
   (d) a detector for detecting electromagnetic radiation emitted from a single molecule corresponding to a single molecule of the analyte in the interrogation space if the analyte is present in the sample.

2. The apparatus of claim 1, wherein the detector determines a background photon level in the interrogation space in the absence of the single molecule and the apparatus compares the background photon level to amount of photons detected from the single molecule.

3. The apparatus of claim 1, wherein the electromagnetic radiation source is a continuous wave laser.

4. The apparatus of claim 1, wherein the translation system comprise a scan motor with a movable mirror.

5. The apparatus of claim 1, wherein the electromagnetic radiation source directs a laser beam at the sample.

6. The apparatus of claim 1, wherein the apparatus discriminates signal and background noise.

7. The apparatus of claim 1, wherein the background noise comprises intrinsic fluorescence of non-labelled particles present in the sample, Raman scattering or electronic noise.

8. The apparatus of claim 1, wherein the detector detects electromagnetic radiation emitted by a fluorescent moiety.

9. The apparatus of claim 1, wherein the single molecule comprises a binding partner for the analyte.

10. The apparatus of claim 9, wherein the single molecule further comprises a fluorescent moiety associated with the binding partner.

11. The apparatus of claim 1, wherein the interrogation space is of a volume between about 15 $\mu m^3$ and about 11000 $\mu m^3$.

12. The apparatus of claim 1, wherein the interrogation space is of a volume between about 200 $\mu m^3$ and about 3000 $\mu m^3$.

13. The apparatus of claim 1, wherein the interrogation space is of a volume between about 500 $\mu m^3$ and about 600 $\mu m^3$.

14. The apparatus of claim 1, further comprising a microscope objective wherein a depth of field of the microscope objective and a diameter of an aperture imaged to the microscope objective together define the interrogation space.

15. The apparatus of claim 1, further comprising a microscope objective wherein a depth of field of the microscope objective and a lateral extent of an electromagnetic radiation beam together define the interrogation space.

16. A method for detecting an analyte in a sample, the method comprising:
   (a) contacting the sample with a first binding partner for the analyte comprising a label to form a complex of the analyte, the first binding partner and label;
   (b) removing unbound first binding partner from the sample;
   (c) directing electromagnetic radiation from an electromagnetic radiation source to an interrogation space in the sample;
   (d) detecting the presence or absence of a single molecule of the label in the interrogation space located at a first position in the sample;
   (e) translating the interrogation space through the sample to a subsequent position in the sample;
   (f) detecting the presence or absence of a subsequent single molecule of the label in the subsequent position in the sample; and
   (g) repeating steps (e) and (f) as required to detect the presence or absence of a single molecule of the label in more than one position of the sample, thereby determining the presence of the analyte in the sample.

17. The method of claim 16, wherein the interrogation space is of a volume between about 15 $\mu m^3$ and about 11000 $\mu m^3$.

18. The method of claim 16, wherein the interrogation space is of a volume between about 200 µm³ and about 3000 µm³.

19. The method of claim 16, wherein the interrogation space is of a volume between about 500 µm³ and about 600 µm³.

20. The method of claim 16, wherein the label is a fluorescent moiety.

21. The method of claim 16, further comprising a second binding partner for the analyte bound to a solid phase.

22. The method of claim 16, further comprising eluting the binding partner from the complex following step (c).

23. The method of claim 16, wherein the detecting comprises determining a background photon level in the interrogation space in the absence of the single molecule and the apparatus compares the background photon level to amount of photons detected in step (d).

24. The method of claim 16, wherein a source of the electromagnetic radiation source is a continuous wave laser.

25. The method of claim 16, further comprising discriminating signal and background noise.

26. The method of claim 25, wherein the background noise comprises intrinsic fluorescence of non-labelled particles present in the sample, Raman scattering or electronic noise.

27. The method of claim 16, wherein the analyte is cardiac troponin I (cTnI).

* * * * *